(12) United States Patent
Abbott et al.

(10) Patent No.: US 7,795,007 B2
(45) Date of Patent: Sep. 14, 2010

(54) DETECTION OF POST-TRANSLATIONALLY MODIFIED PEPTIDES WITH LIQUID CRYSTALS

(75) Inventors: Nicholas L. Abbott, Madison, WI (US); Brian H. Clare, Madison, WI (US); Paul J. Bertics, Oregon, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 470 days.

(21) Appl. No.: 11/156,911

(22) Filed: Jun. 20, 2005

(65) Prior Publication Data

US 2006/0003389 A1     Jan. 5, 2006

Related U.S. Application Data

(63) Continuation-in-part of application No. 10/711,517, filed on Sep. 23, 2004.

(60) Provisional application No. 60/581,198, filed on Jun. 18, 2004, provisional application No. 60/505,114, filed on Sep. 23, 2003.

(51) Int. Cl.
*C12M 1/34* (2006.01)
*G01N 33/553* (2006.01)
*G01N 33/547* (2006.01)
*C07K 1/10* (2006.01)
*G01N 33/53* (2006.01)

(52) U.S. Cl. .................... 435/287.2; 436/525; 436/532; 530/402; 435/7.92

(58) Field of Classification Search .............. 435/287.2, 435/7.1, 7.4, 7.72, 7.92, 17; 436/525, 544, 436/73; 530/402
See application file for complete search history.

(56) References Cited

U.S. PATENT DOCUMENTS

| | | | |
|---|---|---|---|
| 4,513,034 A | 4/1985 | Sparer et al. | |
| 4,597,942 A | 7/1986 | Meathrel | |
| 4,902,106 A | 2/1990 | Dijon et al. | |
| 5,352,461 A | 10/1994 | Feldstein et al. | |
| 5,658,491 A | 8/1997 | Kistner et al. | |
| 5,677,195 A | 10/1997 | Winkler et al. | |
| 5,854,864 A | 12/1998 | Knoesen et al. | |
| 5,886,195 A | 3/1999 | Tang et al. | |
| 6,047,095 A | 4/2000 | Knoesen et al. | |
| 6,096,386 A | 8/2000 | Biebuyck et al. | |
| 6,171,802 B1 | 1/2001 | Woolverton et al. | |
| 6,284,197 B1 | 9/2001 | Abbott et al. | |
| 6,284,392 B1 | 9/2001 | Seth et al. | |
| 6,288,392 B1 | 9/2001 | Abbott et al. | |
| 6,292,296 B1 | 9/2001 | Choi et al. | |
| 6,364,459 B1 | 4/2002 | Sharma et al. | |
| 6,537,499 B1 | 3/2003 | Bernard et al. | |
| 6,596,346 B2 | 7/2003 | Bernard et al. | |
| 6,600,076 B1 | 7/2003 | Abbott et al. | |
| 6,623,107 B2 | 9/2003 | Sharma et al. | |
| 6,652,885 B2 | 11/2003 | Steiner et al. | |
| 6,692,699 B2 | 2/2004 | Abbott et al. | |
| 6,797,463 B2 | 9/2004 | Abbott et al. | |
| 6,803,205 B2 * | 10/2004 | Duffy et al. ................... 435/15 |
| 6,849,321 B2 | 2/2005 | Abbott et al. | |
| 6,852,285 B2 | 2/2005 | Abbott et al. | |
| 6,858,423 B1 | 2/2005 | Abbott et al. | |
| 2001/0004526 A1 | 6/2001 | Everhart et al. | |
| 2001/0013294 A1 | 8/2001 | Bruno et al. | |
| 2002/0004216 A1 | 1/2002 | Abbott et al. | |
| 2002/0028451 A1 | 3/2002 | Abbott et al. | |
| 2002/0054188 A1 | 5/2002 | Sharma et al. | |
| 2002/0055093 A1 | 5/2002 | Abbott et al. | |
| 2002/0098364 A1 | 7/2002 | Bernard et al. | |
| 2002/0142453 A1 | 10/2002 | Abbott et al. | |
| 2002/0164604 A1 | 11/2002 | Abbott et al. | |
| 2003/0099993 A1 | 5/2003 | Abbott et al. | |
| 2004/0091620 A1 | 5/2004 | Abbott et al. | |
| 2004/0161800 A1 | 8/2004 | Abbott et al. | |
| 2005/0079486 A1 | 4/2005 | Abbott et al. | |
| 2005/0079487 A1 | 4/2005 | Murphy et al. | |
| 2005/0106562 A1 | 5/2005 | Abbott et al. | |

FOREIGN PATENT DOCUMENTS

| | | |
|---|---|---|
| WO | 94/03496 | 2/1994 |
| WO | 97/32202 | 9/1997 |
| WO | 97/33737 | 9/1997 |
| WO | 97/35198 | 9/1997 |
| WO | 98/04652 | 2/1998 |
| WO | 99/63329 | 12/1999 |

OTHER PUBLICATIONS

Hidaka, H. et al., Biochemistry 23:5036-5041 (1984).
Cohen, P., Nature Reviews Drug Discovery, 1:309-315 (2002).
Yan, J.X. et al., Journal of Chromatography A, 808:23-41 (1998).
Crul, M., et al., Anticancer Drugs. 12(3):163-184 (2001).
Prime, K.L., and Whitesides, G.M., J. Am. Chem. Soc. 115:10714-10721 (1993).
Xiao, S-J., et al., Langmuir 14:5507-5516 (1998).
Langmuir 19:1586-1591 (2003).
Houseman, B.T. et al., Nature Biotechnology, 20:270-274 (2002).
Houseman, B.T. et al., Langmuir, 19:1522-1531 (2003).
Pale-Grosdemanage et al., J. Am. Chem. Soc. 113, 12-20 (1991).
Mahoney, C.W. et al., Analytical Biochemistry 268:371-376 (1999).
Liedberg, B., et al., Langmuir, 13:5329-5334 (1997).
Jeon, N.L., et al., Langmuir, 16:8311-8316 (2000).

(Continued)

*Primary Examiner*—Shafiqul Haq
(74) *Attorney, Agent, or Firm*—Quarles & Brady LLP

(57) ABSTRACT

A method for differentiating between a post-translationally modified peptide and a peptide contained in a sample, comprising: (a) contacting the sample with a peptide attachment surface to create a peptidized surface, wherein the sample includes at least one functional group; (b) contacting the peptidized surface with a recognition reagent that selectively binds or forms a complex with the post-translationally modified peptide in the sample to provide an incubated surface; and (c) contacting a liquid crystal with the incubated surface and detecting presence of post-translationally modified peptide in the sample with the liquid crystal.

8 Claims, 20 Drawing Sheets

OTHER PUBLICATIONS

Terrill, R.H., et al., J. Am. Chem. Soc. 122:988-989 (2000).
Wang, Q., et al., Anal. Chem. 76: 1-8 (2004).
Martin, K. et al., Proteomics, 3:1244-1255 (2003).
Nuzzo, R.G.; Dubois, L.H.; Allara, D.L. J. Am. Chem. Soc 1990, 112, 558.
Petoral, R.M.; Herland, A; Broo, K.; Uvdal, K. Langmuir 2003, 19, 10304.
Skaife, J.J.; Abbott, N.L. Langmuir 2000, 16, 3529.
Definitions of the term "peptide" from the Britannica Concise Encyclopedia, the Macmillan Dictionary of Toxicology, and the Columbia Encyclopedia, downloaded from http://www.xreferplus.com/entry/5853278, http://www.xreferplus.com/entry/975638 and http://www.xreferplus.com/entry/4292792, respectively on Mar. 21, 2007.
Supporting Information for the article by Renault et al. (Agnew. Chem. Int. Ed. 2002, 41, No. 13, 2320-2323) obtained from http://www.agnewandte.org on Mar. 21, 2007.
Bernard et al., Langmuir 1998, 14(9), 2225-2229.
Bernard et al., Adv. Mater. 2000, 12:1067-1070.
Bernard et al., Nat. Biotechnol. 2001, 19:866-869.
Brake et al., Langmuir 2002, 18:6101-6109.
Charych et al., Science 1993, 261(5121):585-588. Erratum in: Science 1993, 261(5127):1375.
Chung et al., Japanese Journal of Applied Physics 2000, 39: Part 2, No. 3, A/B, L185-L187.
Cocchi et al., Journal of Immunological Methods 1993, 160:1-9.
Cornell et al., Nature 1997, 387(6633):580-583.
Dancil et al., J. Am. Chem. Soc. 1999, 121:7925-7930.
Dulcey et al., Science 1991, 252(5005):551-554.
Everitt et al., Physical Rev. 2000, 62:R4833-4836.
Geary et al., J. Appl. Phys. 1987, 62:4100-4108.
Geissler et al., J. Am. Chem. Soc. 2000, 122:6303-6304.
Gu et al., Chemphyschem. 2002, 3(5):448-451.
Gupta et al., Chemistry of Materials 1996, 8(7):1366-1369.
Gupta et al., Langmuir 1996, 12:2587-2593.
Gupta et al., Science 1998, 279(5359):2077-2080.
Harlow et al., Cold Spring Harbor Laboratory 1988, p. iii-ix.
Harnett et al., Appl. Phys. Lett. 2000, 76:2466-2468.
Haussling et al., Langmuir 1991, 7:1837-1840.
Hidber et al., Langmuir 1996, 12:1375-1380.
Kim et al., Advanced Materials 2001, 13(19):1445-1449.
Kim et al., Anal. Chem. 2000, 72(19):4646-4653.
Kim et al., Langmuir 2002, 18:5269-5276.
Kuby, Immunology 1992, Chapter 7, 147-151.
Kumar et al., Appl. Phys. Lett. 1993, 63:2002-2004.
Kumar et al., Langmuir 1994, 10:1498-1511.
Lahiri et al., Langmuir 1999, 15:2055-2060.
Lin et al., Science 1997, 278(5339):840-843.
Luk et al., Science 2004.
Martin et al., Langmuir 2000, 16:9944-9946.
Mikami et al., Kobunshi Ronbunshu 1999, 56(6):396-400.
Miller et al., Appl. Phys. Lett. 1996, 69(13):1852-1854.
Ouskova et al., Phys. Rev. 2001, 64(5 pt 1):051709.
Pan et al., Langmuir 1997, 13:1365-1367.
Renault et al., J. Phys. Chem. 2003, 107:703-711.
Renault et al., Angew. Chem. Int. Ed. Engl. 2002, 41(13):2320-2323.
Rogers et al., Advanced Materials 1999, 11(9):741-745.
Schmitt et al., Thin Solid Films 1992, 210/211(1-2):815-817.
Shah et al., J. Phys. Chem. 2001, 105:4936-4950.
Shah et al., Science 2001, 293:1296-1299.
Shah et al., J. Am. Chem. Soc. 1999, 121:11300-11310.
Skaife et al., Langmuir 2001, 17:5448-5457.
Starkey et al., Clin. Microbiol. 1990, 28(4):819-822.
Tan et al., Langmuir 2002, 18:519-523.
Tercero et al., Langmuir 2004. 20(6):2375-2385.
Tingey et al., Langmuir 2004. 3;20(16):6818-6826.
Tingey et al., Adv. Mater 2004, 16(15):1331-1336.
Tizard, Veterinary Immunology 1996, p. xv-xxiv.
Tsukruk et al., Langmuir 1997, 13:2171-2176.
Van Oss et al., Immunochemistry 1994, p. v-vii.
Wanless et al., J.Chem. Phys. 1994, 101:4260-4267.
Xia et al., Advanced Materials 1996, 8(12):1015-1017.
Yan et al., J. Am. Chem. Soc. 1998, 120:6179-6180.
Yan et al., Langmuir 1999, 15:1208-1214.
Yang et al., Microchemistry—Spectroscopy and Chemistry in Small Domains 1994, p. 441-454.
Yang et al., Advanced Materials 2003, 15(21):1819-1823.
Yaroshchuk et al., Phys. Rev. E. 2004, 69(1 Pt 1):011702.
Non-Final Office Action mailed Apr. 10, 2007, in U.S. Appl. No. 10/711,517.
Final Office Action mailed Jul. 12, 2006, in U.S. Appl. No. 10/711,517.
Non-Final Office Action mailed Nov. 21, 2005, in U.S. Appl. No. 10/711,517.

\* cited by examiner

5% Areal Density
SSMCC
And (p)-kemptide
SSMCC
And kemptide
SSMCC
Only (control)
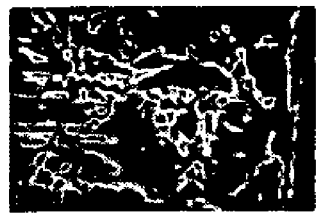
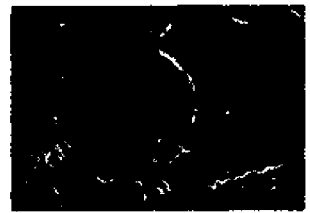
FIG. 9A     FIG. 9B     FIG. 9C FIG. 13A
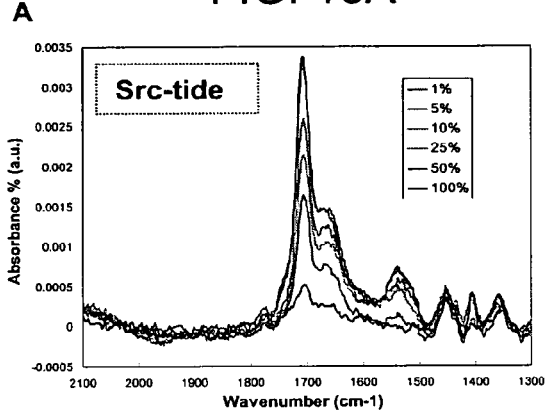
FIG. 13B
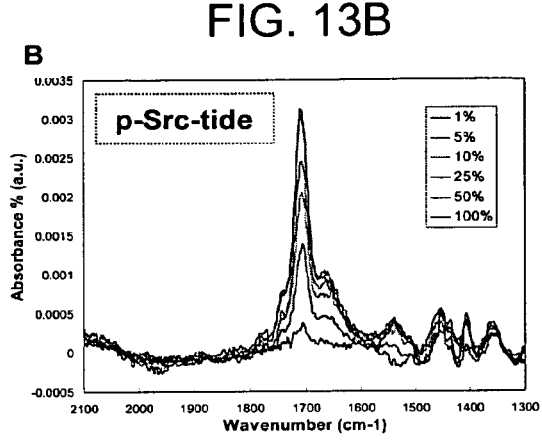
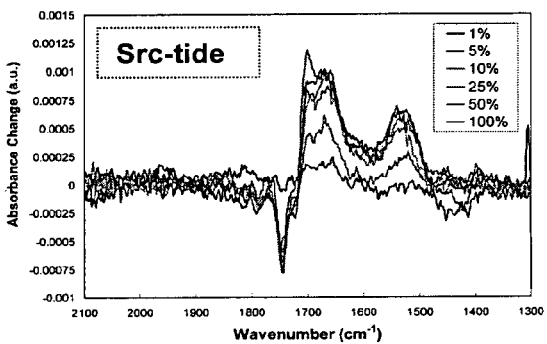
FIG. 13C
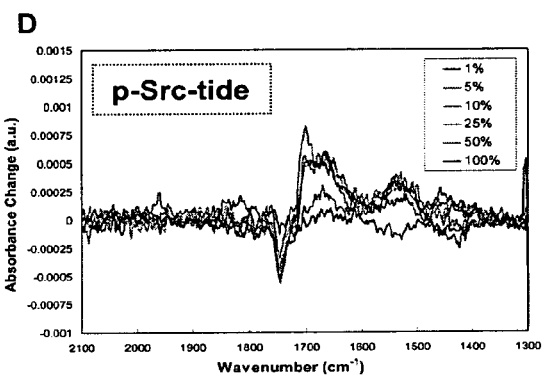
FIG. 13D

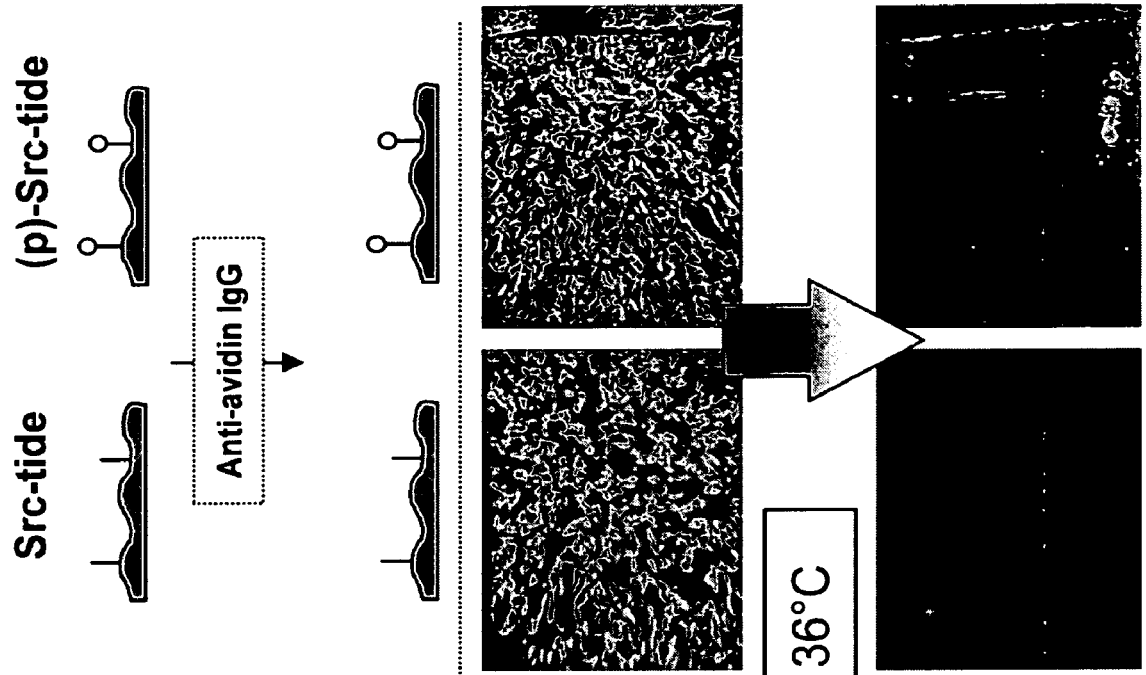
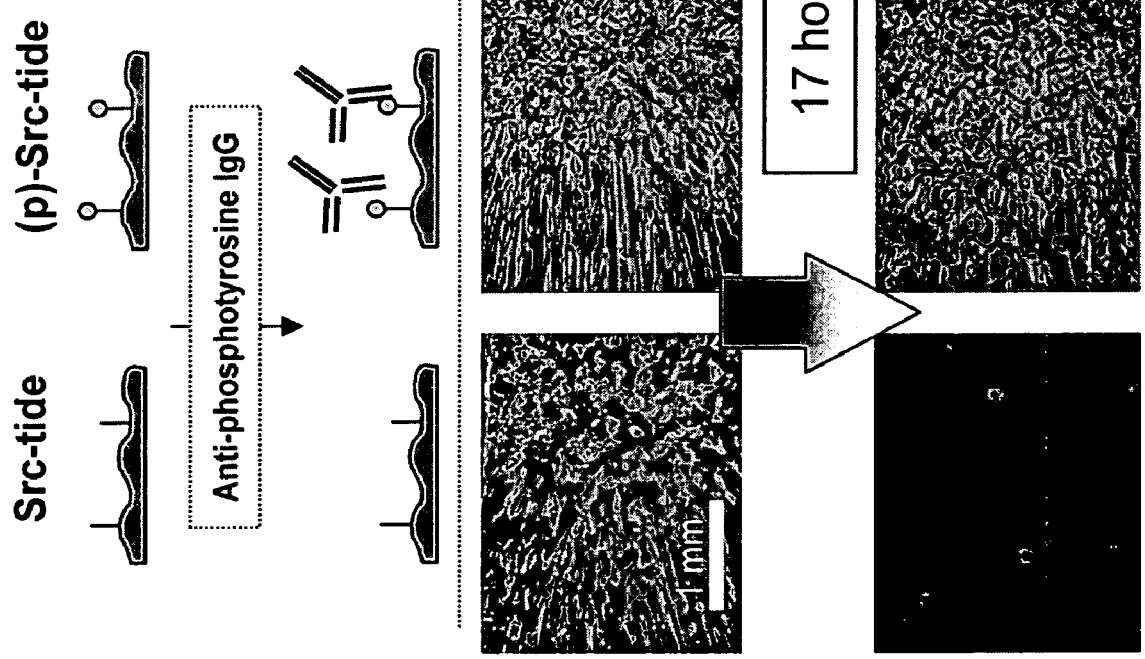
FIG. 18A
FIG. 18B
FIG. 18C

FIG. 19A
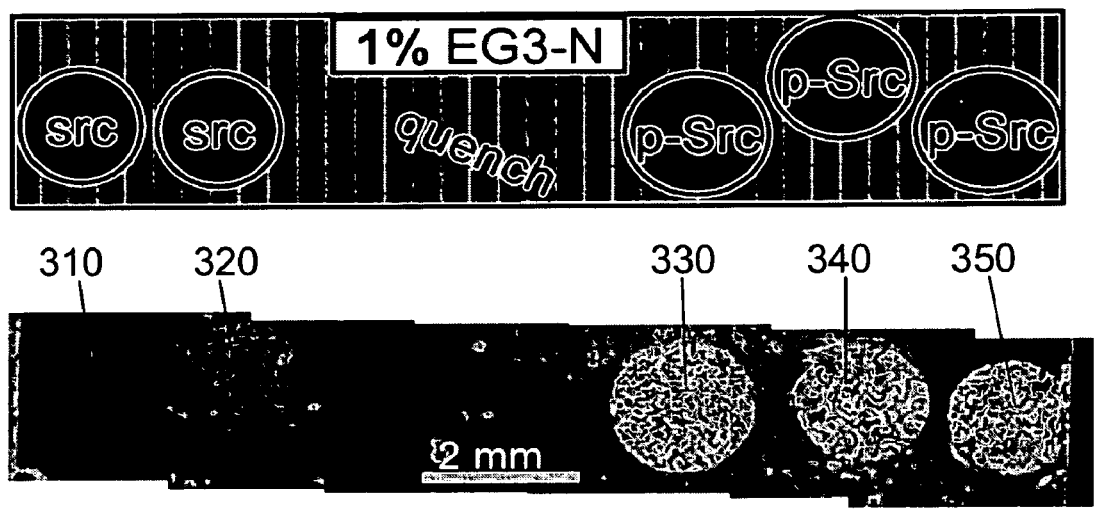
FIG. 19B
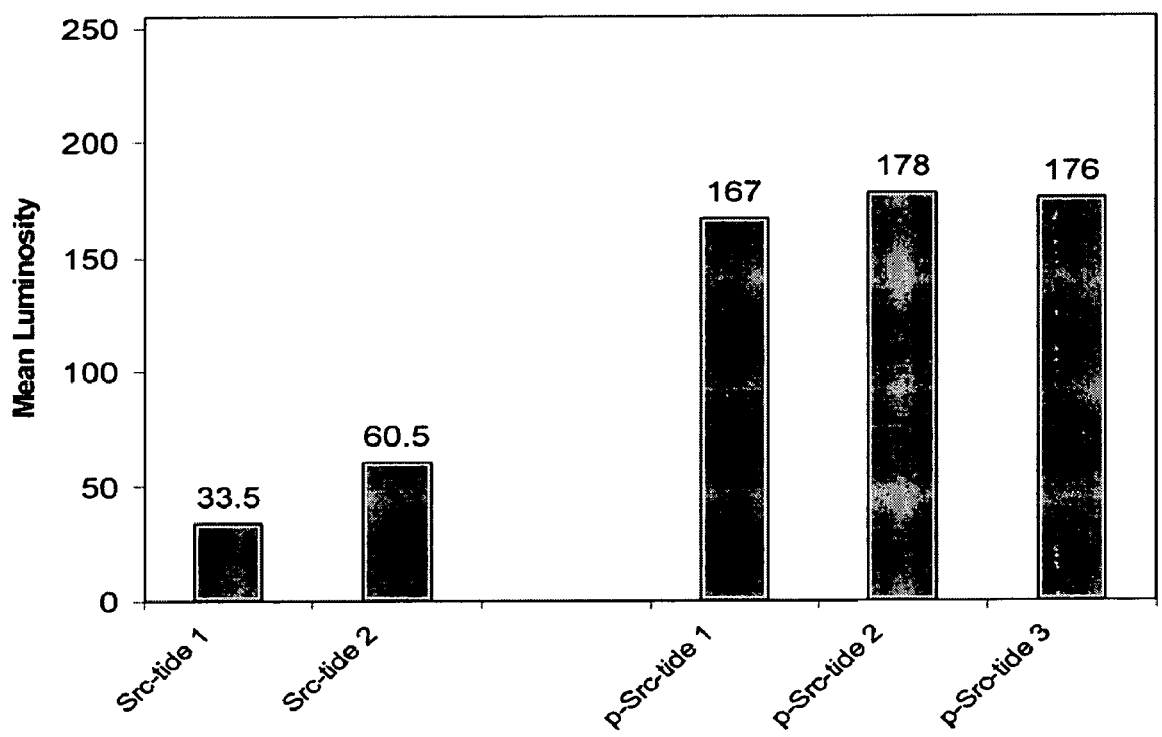
FIG. 19C

FIG. 20A
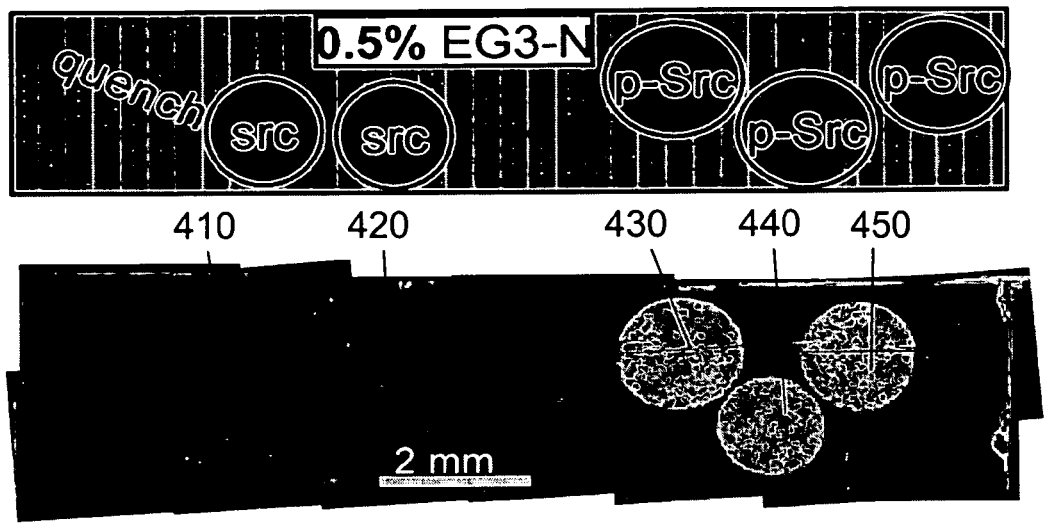
FIG. 20B
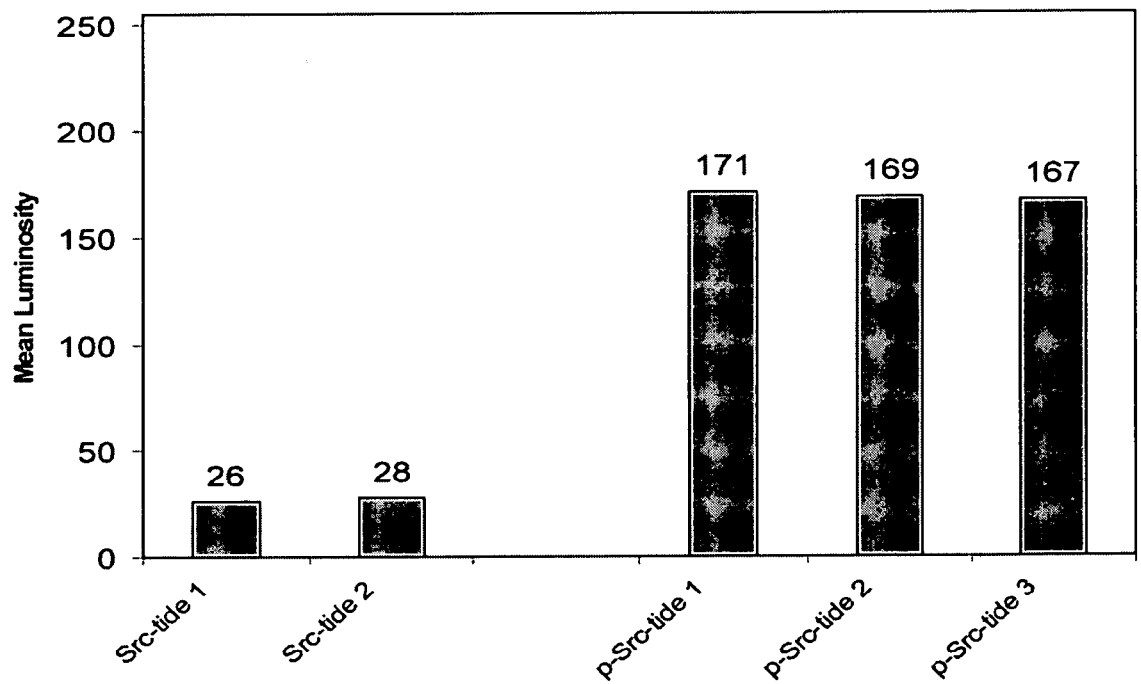
FIG. 20C

Array in contact with LC within 5 minutes of sample preparation

DETECTION OF POST-TRANSLATIONALLY MODIFIED PEPTIDES WITH LIQUID CRYSTALS

RELATED APPLICATIONS

The present continuation-in-part application claims the benefit of U.S. Provisional Patent Application Ser. No. 60/581,198, filed on Jun. 18, 2004 and U.S. Non-Provisional Patent Application 10/711,517, filed Sep. 23, 2004, which in turn claims the benefit of U.S. Provisional Patent Application 60/505,114, filed on Sep. 23, 2003, all of which applications are incorporated herein by reference for all purposes.

GOVERNMENT RIGHTS

This invention was made with United States government support awarded by the following agency: NSF DMR-0079983. The United States has certain rights in this invention.

FIELD OF THE INVENTION

The invention relates generally to methods and devices for differentiating between modified peptides and peptides. More particularly, the invention relates to methods and devices for differentiating between phosphorylated peptides and peptides using liquid crystals.

BACKGROUND OF THE INVENTION

Methods for detecting phosphorylation of peptides and proteins is an area in the fields of analytical chemistry, medicinal chemistry, and biochemistry where considerable effort has been expended. Considerable efforts have also been made with respect to methods for detecting other post-translational modifications of peptides and proteins such as acylation, glycosylation, alkylation, and adenylation.

Post-translational modification of proteins has been recognized for decades as a significant mode of regulation. In particular, phosphorylation, and the reverse process, dephosphorylation, are key factors in numerous aspects of cell signaling, cell cycle regulation, and response to stress (reviewed in Yan, J. X. et al., *Journal of Chromatography A*, 808:23-41 (1998)). Phosphorylation of proteins is catalyzed by a class of enzymes called protein kinases, which transfer the terminal phosphate from adenosine triphosphate (ATP) to a given amino acid residue, typically serine, threonine, or tyrosine. In general, phosphorylation is a reversible process. Dephosphorylation is carried out by protein phosphatases. Moreover, kinases and phosphatases may be inhibited by various factors (Hidaka, H. et al., *Biochemistry* 23:5036-5041 (1984)). Because of their importance in cell signaling and cell cycle regulation, proteins in the phosphorylation cycle, both enzymes and their substrates, have become major targets for the development of pharmaceutical compounds. Protein kinases, in particular, because of their role in cell division and cancer progression, have emerged as the principal targets of drugs aimed at treating cancer, immunosuppression, retinopathy, rheumatoid arthritis, and neurodegeneration (Cohen, P., *Nature Reviews Drug Discovery*, 1:309-315 (2002)).

A variety of methods exists for monitoring and detecting the phosphorylation state of proteins, which is important, among other purposes, for assessing the efficacy of candidate pharmaceutical agents. Antibody-based detection is among the most widely used of these methods. In addition to monoclonal antibodies specific for individual proteins, more recent endeavors have resulted in the production of phospho-motif antibodies, which recognize a phosphoserine or phosphothreonine residue in a conserved amino acid motif (reviewed in Berwick, D. C. and Tavare, J. M., *Trends in Biochemical Science*, 29:227-232 (2004)). Generation of such antibodies requires extensive characterization of the substrate specificity of the kinases being examined. Alternative methods for monitoring kinase activity make use of $^{32}P$_radiolabeled phosphate groups and mass spectrometry to identify modification in protein composition before and after treatment with a kinase (Yan, J. X. et al., *Journal of Chromatography A*, 808: 23-41 (1998)).

In addition to phosphorylation, other co- and post-translational modifications are known to exert regulatory effects on proteins. Acylation, particularly by either fatty acyl or prenyl residues being covalently linked to an —SH group of a cysteine residue, is one such modification (Kendrew, J. editor, THE ENCYCLOPEDIA OF MOLECULAR BIOLOGY, Blackwell Science, Inc. Cambridge, Mass., 1994, p. 15). Ras proteins undergo several post-translational modifications, including farnesylation. Inhibition of the enzyme that carries out this modification, farnesyl transferase, is a promising approach to controlling this oncogenic protein (Crul, M., et al., *Anticancer Drugs*. 12(3):163-84 (2001)). Other commonly encountered post-translational modifications, such as glycosylation and proteolytic cleavage, are important in protein secretion and translocation.

Although various methods have been used to detect phosphorylation and other co- and post-translational modifications of peptides and proteins, a need exists for simple devices and methods that may be used to rapidly detect such modifications, particularly the phosphorylation of peptides and proteins without the need for radioactive labeling and other manipulation, such as hybridization and washing, and without the need for complex instrumentation. A need also remains for methods of manufacturing devices for use in differentiating between post-translationally modified peptides and peptides. Also needed are rapid, high throughput methods for directly detecting phosphorylation state irrespective of the identity of the modified amino acid or its location within a particular protein sequence or known kinase motif.

SUMMARY OF THE INVENTION

The present invention provides devices and methods for differentiation between post-translationally modified peptides and peptides using liquid crystals. The invention also provides a method for preparing devices and kits for differentiating between post-translationally modified peptides and peptides.

In one aspect, the invention provides a method for differentiating between a post-translationally modified peptide and a peptide contained in a sample. The method generally comprises: (a) contacting the sample with a peptide attachment surface to create a peptidized surface, where the sample includes at least one functional group; (b) contacting the peptidized surface with a recognition reagent that selectively binds or forms a complex with the post-translationally modified peptide in the sample to provide an incubated surface; and (c) contacting a liquid crystal with the incubated surface and detecting presence of post-translationally modified peptide in the sample with the liquid crystal.

In a preferred embodiment, the method includes: (a) contacting the sample containing a post-translationally modified peptide, a peptide, or a mixture thereof with a peptide attachment surface to create a peptidized surface; (b) contacting the peptidized surface with a recognition reagent that selectively binds or forms a complex with the post-translationally modified peptide if present to provide an incubated surface; and (c) contacting a liquid crystal with the incubated surface. The post-translationally modified peptide, the peptide, or the mixture thereof contained in the sample comprises a functional group selected to react with exposed functional groups on the surface. In preferred embodiments, the peptide attachment surface includes: (i) a support; (ii) a metal deposited on the support providing a metallized surface; and (iii) a functionalized thiol compound bound to the metallized surface, the functionalized thiol compound includes a first thiol compound and a functional group that reacts with the functional group on the post-translationally modified peptide, the peptide, or the mixture thereof when the post-translationally modified peptide, the peptide, or the mixture thereof is contacted with the peptide attachment surface. In preferred embodiments, the functional group of the thiol is a maleimide group and the peptide has a terminal cysyeine residue. As before, the orientation of the liquid crystal is different when the liquid crystal is contacted with the incubated surface when the incubated surface includes the post-translationally modified peptide than the orientation of the liquid crystal is when the liquid crystal is contacted with the incubated surface when the incubated surface does not include the post-translationally modified peptide. In some embodiments of the method for differentiating between a post-translationally modified peptide and a peptide, the peptide attachment surface further includes a second thiol compound that is bound to the metallized surface.

In some embodiments of the method for differentiating between a post-translationally modified peptide and a peptide, the method includes post-translationally modifying the peptide after the peptide has been contacted with the peptide attachment surface.

In some embodiments of the method for differentiating between a post-translationally modified peptide and a peptide, the functional group on the functionalized thiol compound is a maleimide group.

In some embodiments of the method for differentiating between a post-translationally modified peptide and a peptide, the method includes reacting the first thiol compound with a heterobifunctional linker to provide the functionalized thiol compound. In some such embodiments, the first thiol compound has an amine or ammonium group and the heterobifunctional linker is sulfosuccinimidyl-4-(N-maleimidomethyl)cyclohexane-1-carboxylate, and the amine or ammonium group of the first thiol compound reacts with the heterobifunctional linker to provide the functionalized thiol.

In some embodiments of the method for differentiating between a post-translationally modified peptide and a peptide, the first thiol compound is a compound of formula HS—$(CH_2)_a$—$(OCH_2CH_2)_b$—$NH_2$ or an ammonium salt thereof, wherein a is an integer ranging from 1 to 30, or in some embodiments ranging from 4 to 22, and b is an integer ranging from 0 to 10, or in some embodiments ranging from 1 to 5. In some such embodiments, the first thiol compound is HS—$(CH_2)_{11}(OCH_2CH_2)_3NH_2$ or an ammonium salt thereof. In some embodiments, the compound is the ammonium chloride salt such as a compound of formula HS—$(CH_2)_a$—$(OCH_2CH_2)_b$—$NH_3^+Cl^-$.

In some embodiments of the method for differentiating between a post-translationally modified peptide and a peptide, the second thiol compound is a compound of formula HS—$(CH_2)_c$—$(OCH_2CH_2)_d$—X, wherein c is an integer ranging from 1 to 30, or in some embodiments ranging from 4 to 22, and d is an integer ranging from 0 to 10, or in some embodiments ranging from 1 to 5, and X is selected from an —OH, an alkoxy group, a $CH_3$, a sugar, a zwitterionic group, or a polar non-ionic group. In some such embodiments of the method for differentiating between a post-translationally modified peptide and a peptide, the second thiol compound is a compound of formula HS—$(CH_2)_c$—$(OCH_2CH_2)_d$—OH, wherein c is an integer ranging from 1 to 30, or in some embodiments ranging from 4 to 22, and d is an integer ranging from 0 to 10, or in some embodiments ranging from 1 to 5. In some such embodiments, the second thiol compound is HS—$(CH_2)_{11}(OCH_2CH_2)_3OH$.

In some embodiments of the method for differentiating between a post-translationally modified peptide and a peptide, the molar ratio of the first thiol compound to the second thiol compound on the metallized surfaces of the peptide attachment surface ranges from 0.1:99.9 to 100%. In other embodiments, the molar ratio of the first thiol compound to the second thiol compound on the metallized surfaces of the peptide attachment surface ranges from 0.2:99.8 to 20:80. In still other embodiments, the molar ratio of the first thiol compound to the second thiol compound on the metallized surfaces of the peptide attachment surface ranges from 0.2:99.8 to 5:95, from 0.2:99.8 to 10:90, from 0.5:99.5 to 10:90, or from 0.5:99.5 to 5:95.

In some embodiments of the method for differentiating between a post-translationally modified peptide and a peptide, the liquid crystal is a nematic liquid crystal. In some such embodiments, the liquid crystal is 4-pentyl-4'-cynaobiphenyl (5CB). In other embodiments, the liquid crystal is N-(4-methoxybenzylidene)-4-butylaniline (MBBA). In further embodiments, the liquid crystal TL205 (E. Merck, Darmstadt, Germany).

In some embodiments of the method for differentiating between a post-translationally modified peptide and a peptide, the metallized surface of the peptide attachment surface has a top layer of gold. In some such embodiments, the top layer of gold has a thickness ranging from 5 nm to 30 nm. In some embodiments, the top layer of gold overlies a layer of a material that promotes adhesion of the gold to the support, which in some embodiments may be titanium. In some such embodiments, the layer of the material that promotes adhesion of the gold is a layer of titanium with a thickness ranging from 0.5 nm to 10 nm.

In some embodiments of the method for differentiating between a post-translationally modified peptide and a peptide, the post-translationally modified peptide is a phosphorylated peptide. In some such embodiments, the recognition reagent is an antibody or antibody fragment that selectively binds or forms a complex with the phosphorylated peptide. In other such embodiments, the recognition reagent is a cationic compound. In other embodiments, the recognition reagent is a cationic surfactant, a polyelectrolyte, a cationic iron compound, or a phosphosensor dye that selectively binds or forms a complex with a phosphate group on the phosphorylated peptide. In other embodiments, the phosphorylated peptide has at least one phosphorylated serine and/or phosphorylated threonine residue. In other embodiments, the phosphorylated peptide has at least one phosphorylated tyrosine residue.

In other embodiments of the method for differentiating between a post-translationally modified peptide and a peptide, the post-translationally modified peptide is an acylated, glycosylated, adenylated, farnesylated, or alkylated peptide or is a peptide that has been proteolytically cleaved.

In some embodiments of the method for differentiating between a post-translationally modified peptide and a peptide, the method includes viewing the incubated surface using polarized light after the incubated surface has been contacted with the liquid crystal. In some such embodiments, the incubated surface is viewed through a polarizing microscope after the incubated surface has been contacted with the liquid crystal.

In some embodiments of the method for differentiating between a post-translationally modified peptide and a peptide, the method includes measuring a dielectric property of the incubated surface, using an evanescent optical method on the incubated surface, or measuring the optical absorbance of the incubated surface to determine whether a post-translationally modified peptide is present on the incubated surface.

In some embodiments of the method for differentiating between a post-translationally modified peptide and a peptide, the method further includes pairing the incubated surface with a second surface to form an optical cell, wherein the second surface uniformly anchors the liquid crystal, and further wherein the liquid crystal is located on the surface of the incubated surface between the incubated surface and the second surface of the optical cell.

In another aspect, the invention provides a device for differentiating between a post-translationally modified peptide and a peptide. The device includes (a) a support having a top surface; (b) a metal overlying the top surface of the support providing a metallized surface; (c) a first thiol compound, a functionalized thiol compound, or the reaction product of the functionalized thiol compound with a post-translationally modified peptide, a peptide, or a mixture thereof, wherein the first thiol compound or the functionalized thiol compound comprise an —SH group, wherein the —SH group of the first thiol compound or the functionalized thiol compound is attached to a first portion of a top surface of the metallized surface, wherein the first thiol compound further comprises an amine or ammonium group, and further wherein the functionalized thiol comprises the reaction product of the first thiol compound and a functional group that will react with a —SH a group on the post-translationally modified peptide or the peptide; and (d) a second thiol compound comprising an —SH group, wherein the —SH group of the second thiol compound is attached to the first portion of the top surface of the metallized surface. The molar ratio of the first thiol compound to the second thiol compound attached to the top surface of the support ranges from 0.1:99.9 to 50:50. In some embodiments the molar ratio of the first thiol compound to the second thiol attached to the top surface of the support ranges from compound ranges from 0.2:99.8 to 20:80, from 0.2:99.8 to 10:90, from 0.5:99.5 to 20:80, from 0.5:99.5 to 10:90, from 0.5:99.5 to 5:95, or from 0.5:99.5 to 2.5:97.5.

In some embodiments of the device for differentiating between a post-translationally modified peptide and a peptide, the first thiol compound is a compound of formula HS—$(CH_2)_a$—$(OCH_2CH_2)_b$—$NH_2$ or an ammonium salt thereof, wherein a is an integer ranging from 1 to 30, or in some embodiments ranging from 4 to 22, and b is an integer ranging from 0 to 10, or in some embodiments ranging from 1 to 5. In some such embodiments, the first thiol compound comprises HS—$(CH_2)_{11}(OCH_2CH_2)_3NH_2$ or an ammonium salt thereof.

In some embodiments of the device for differentiating between a post-translationally modified peptide and a peptide, the second thiol compound is a compound of formula HS—$(CH_2)_c$—$(OCH_2CH_2)_d$—X, wherein c is an integer ranging from 1 to 30, or in some embodiments ranging from 4 to 22, and d is an integer ranging from 0 to 10, or in some embodiments ranging from 1 to 5, and X is selected from an —OH, an alkoxy group, a $CH_3$, a sugar, a zwitterionic group, or a polar non-ionic group. In some such embodiments of the device for differentiating between a post-translationally modified peptide and a peptide, the second thiol compound comprises a compound of formula HS—$(CH_2)_c$—$(OCH_2CH_2)_d$—OH, wherein c is an integer ranging from 1 to 30, or in some embodiments ranging from 4 to 22, and d is an integer ranging from 0 to 10, or in some embodiments ranging from 1 to 5. In some such embodiments, the second thiol compound comprises HS—$(CH_2)_{11}(OCH_2CH_2)_3OH$. In some embodiments, the second thiol comprises an oligoethylene glycol group, or an alkyl-terminated oligoethylene glycol group (Prime, K. L., and Whitesides, G. M., *J. Am. Chem. Soc.* 115:10714-10721 (1993), incorporated herein by reference in its entirety and for all purposes as if fully set forth herein) and an —SH group, wherein the —SH group of the second thiol compound is attached to the first portion of the top surface of the metallized surface. In still other embodiments, the second thiol has the formula HS$(CH_2)_{10}R$ where R is $CH_3$, $CH_2OH$ or oligo(ethylene oxide), described in Prime and Whitesides, supra.

In some embodiments of the device for differentiating between a post-translationally modified peptide and a peptide, the metallized surface comprises a top layer of gold. In some such embodiments, the top layer of gold has a thickness ranging from 5 nm to 30 nm. In some embodiments, a metal such as gold is obliquely deposited at an angle ranging from 30° to about 60° to a planar surface of the support. In other embodiments, the top layer of the metal such as gold has a thickness ranging from 50 Å to 300 Å (from 5 nm to 30 nm). In some embodiments, the top layer of gold overlies a layer of a material that promotes adhesion of the gold to the support. In some such embodiments, the material that promotes adhesion of the gold is titanium, and in some such embodiments, the titanium has a thickness ranging from 5 Å to 100 Å (from 0.5 nm to 10 nm), from 5 Å to 20 Å (from 0.5 nm to 2 nm), or from 5 Å to 10 Å (from 0.5 nm to 1 nm).

In some embodiments of the device for differentiating between a post-translationally modified peptide and a peptide, the device comprises the first thiol compound and does not comprise the functionalized thiol compound.

In some embodiments of the device for differentiating between a post-translationally modified peptide and a peptide, the device comprises the functionalized thiol compound. In some such embodiments, the functionalized thiol compound comprises a maleimide functional group. In some such embodiments, the functionalized thiol compound is a compound having the following formula

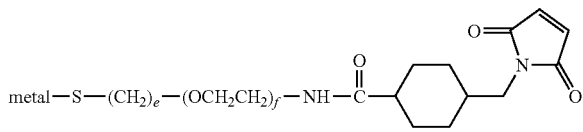

wherein e is an integer ranging from 1 to 30, or in some embodiments ranging from 4 to 22, and f is an integer ranging from 0 to 10, or in some embodiments ranging from 1 to 5. In some such embodiments, the functionalized thiol compound is a compound having the following formula

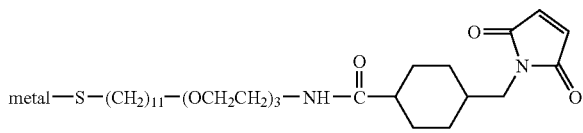

In some embodiments of the device for differentiating between a post-translationally modified peptide and a peptide, the device includes the reaction product of the functionalized thiol with the post-translationally modified peptide, the peptide, or the mixture thereof. In some such embodiments, the device comprises the reaction product of the functionalized thiol with the post-translationally modified peptide or the mixture of the post-translationally modified peptide and the peptide.

In some embodiments of the device for differentiating between a post-translationally modified peptide and a peptide, the molar ratio of the first thiol compound to the second thiol compound or the ratio of the functionalized thiol compound to the second thiol compound varies across the top surface of the metallized surface.

In another aspect, the invention provides a kit. The kit includes a device according to any of the above embodiments and a recognition reagent. In some embodiments, the recognition reagent is an antibody, an antibody fragment, or a cationic compound. In other embodiments, the recognition reagent is an antibody, an antibody fragment, a cationic surfactant, a polyelectrolyte, a cationic iron compound, or a phosphosensor dye. In some such embodiments, the recognition reagent is an antibody or an antibody fragment that selectively binds or forms a complex with a phosphorylated peptide.

In some embodiments of the device for differentiating between a post-translationally modified peptide and a peptide, the molar ratio of the first thiol compound to the second thiol compound or the ratio of the functionalized thiol compound to the second thiol compound varies across the top surface of the metallized surface.

In some embodiments of the device for differentiating between a post-translationally modified peptide and a peptide, the top surface of the metallized surfaces comprises a second portion, further wherein the first thiol compound or the functionalized thiol compound are attached to the second portion, still further wherein the second thiol compound is attached to the second portion. In some such embodiments, the top surface comprises a plurality of separate portions such that the device provides an array.

In another aspect, the invention provides a method for preparing a peptide attachment surface. The method includes (a) contacting a metallized surface that overlies a support with a first thiol compound and a second thiol compound providing a surface that comprises a self-assembled monolayer comprising the first and second thiol compounds attached to the metallized surface; (b) contacting the surface that comprises the self-assembled monolayer with a heterobifunctional linker to provide the peptide attachment surface, wherein the heterobifunctional linker comprises a functional group that reacts with an —SH group of a post-translationally modified peptide, a peptide, or a mixture thereof, wherein the first thiol compound reacts with the heterobifunctional linker to provide a functionalized thiol attached to the metallized surface. The first thiol has a —SH group or disulfide linkage and an amine or ammonium group that reacts with the heterobifunctional linker and the second thiol has an —OH group and a —SH group or disulfide linkage. The molar ratio of the first thiol to the second thiol compound on the surface that has the self-assembled monolayer having the first and second thiol compounds ranges from 0.1:99.9 to 100:0.

In some embodiments of the method for preparing a peptide attachment surface, the first thiol compound comprises a compound of formula HS—(CH$_2$)$_a$—(OCH$_2$CH$_2$)$_b$—NH$_2$, an ammonium salt thereof, or a disulfide equivalent thereof wherein a is an integer ranging from 1 to 30, or in some embodiments ranging from 4 to 22, and b is an integer ranging from 0 to 10, or in some embodiments ranging from 1 to 5. In some such embodiments, the first thiol compound comprises HS—(CH$_2$)$_{11}$(OCH$_2$CH$_2$)$_3$NH$_2$, an ammonium salt thereof, or a disulfide equivalent thereof.

In some embodiments of the method for preparing a peptide attachment surface, the second thiol compound is a compound of formula HS—(CH$_2$)$_c$—(OCH$_2$CH$_2$)$_d$—X, wherein c is an integer ranging from 1 to 30, or in some embodiments ranging from 4 to 22, and d is an integer ranging from 0 to 10, or in some embodiments ranging from 1 to 5, and X is selected from an —OH, an alkoxy group, a CH$_3$, a sugar, a zwitterionic group, or a polar non-ionic group. In some embodiments of the method for preparing a peptide attachment surface, the second thiol compound comprises a compound of formula HS—(CH$_2$)$_c$—(OCH$_2$CH$_2$)$_d$—OH or a disulfide equivalent thereof, wherein c is an integer ranging from 1 to 30, or in some embodiments ranging from 4 to 22, and d is an integer ranging from 0 to 10, or in some embodiments ranging from 1 to 5. In some such embodiments, the second thiol compound comprises HS—(CH$_2$)$_{11}$(OCH$_2$CH$_2$)$_3$OH or a disulfide equivalent thereof.

In some embodiments of the method for preparing a peptide attachment surface, the molar ratio of the first thiol compound to the second thiol compound on the surface that comprises the self-assembled monolayer comprising the first and thiol compounds ranges from 0.2:99.8 to 20:80, from 0.2:99.8 to 10:90, from 0.5:99.5 to 20:80, from 0.5:99.5 to 10:90, from 0.5:99.5 to 5:95, or from 0.5:99.5 to 2.5:97.5.

In some embodiments of the method for preparing a peptide attachment surface, the metallized surface comprises a top layer of gold. In some such embodiments, the top layer of gold has a thickness ranging from 5 nm to 30 nm. In some embodiments, a metal such as gold is obliquely deposited at an angle ranging from 30° to about 60° to a planar surface of the support. In other embodiments, the top layer of the metal such as gold has a thickness ranging from 50 Å to 300 Å (from 5 nm to 30 nm). In some embodiments, the top layer of gold overlies a layer of a material that promotes adhesion of the gold to the support. In some such embodiments, the material that promotes adhesion of the gold is titanium, and in some such embodiments, the titanium has a thickness ranging from 5 Å to 100 Å (from 0.5 nm to 10 nm), from 5 Å to 20 Å (from 0.5 nm to 2 nm), or from 5 Å to 10 Å (from 0.5 nm to 1 nm).

In some embodiments of the method for preparing a peptide attachment surface, the heterobifunctional linker has a maleimide group. In some such embodiments, the functionalized thiol attached to the metallized surface is a compound having the following formula

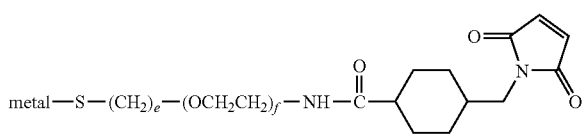

wherein e is an integer ranging from 1 to 30, or in some embodiments ranging from 4 to 22, and f is an integer ranging from 0 to 10, or in some embodiments ranging from 1 to 5. In some such embodiments, the functionalized thiol attached to the metallized surface is a compound having the following formula

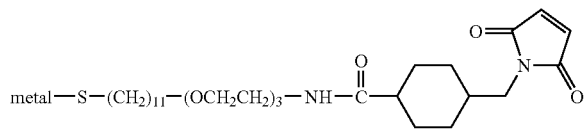

In one aspect, the invention provides a method for preparing a peptidized surface. The method includes: (a) preparing the peptide attachment surface according to the any of the methods of the invention; and, (b) contacting the peptide attachment surface with a post-translationally modified peptide, a peptide, or a mixture thereof to provide the peptidized surface. In some embodiments of the method for preparing a peptidized surface, the post-translationally modified peptide is a phosphorylated peptide. In some embodiments, the post-translationally modified peptide is an acylated, glycosylated, adenylated, farnesylated, or alkylated peptide or is a peptide that has been proteolytically cleaved. In some embodiments, the method for preparing a peptidized surface includes contacting the peptide attachment surface with the peptide to provide the peptidized surface, and post-translationally modifying the peptide after it has been contacted with the peptide attachment surface.

In one aspect the invention provides a method of forming an incubated surface. The method includes: (a) preparing a peptidized surface according to the methods of the invention; and (b) contacting the peptidized surface with a recognition reagent that selectively binds or forms a complex with the post-translationally modified peptide. In some embodiments, the recognition reagent is an antibody, an antibody fragment, or a cationic compound. In some embodiments, the recognition reagent is an antibody, an antibody fragment, a cationic surfactant, a polyelectrolyte, a cationic iron compound, or a phosphosensor dye. In some embodiments, the post-translationally modified peptide is a phosphorylated peptide and the recognition reagent is an antibody or an antibody fragment that selectively binds or forms a complex with the phosphorylated peptide. In some embodiments, the post-translationally modified peptide is an acylated, glycosylated, adenylated, farnesylated, or alkylated peptide or is a peptide that has been proteolytically cleaved.

In another aspect the invention provides a method of differentiating between a post-translationally modified peptide and a peptide. The method includes: (a) preparing an incubated surface using the methods of the invention; (b) contacting the incubated surface with a liquid crystal; and (c) determining whether the anchoring of the liquid crystal on the incubated surface is disrupted. For example, the anchoring of a liquid crystal on an incubated surface that includes a post-translationally modified peptide that has been contacted with a recognition agent is different from the anchoring of a liquid crystal on an incubated surface that does not include the post-translationally modified peptide.

In another aspect the invention provides a method of differentiating between a post-translationally modified peptide and a peptide. The method includes: (a) preparing a peptidized surface using the methods of the invention; (b) contacting the peptidized surface with a liquid crystal; and (c) determining whether the anchoring of the liquid crystal on the peptidized surface is disrupted. For example, the anchoring of a liquid crystal on a peptidized surface that includes a post-translationally modified peptide is different from the anchoring of a liquid crystal on a peptidized surface that does not include the post-translationally modified peptide.

In another aspect the invention provides a method of preparing a peptide attachment surface that includes: (a) contacting a surface that has hydroxyl groups with a surface modifying agent to provide a modified surface that possesses amine groups, the surface modifying agent having a functional group that reacts with the hydroxyl groups on the surface and an amine group; and (b) contacting the modified surface with a heterobifunctional linker to provide the peptide attachment surface. The heterobifunctional linker has a functional group that reacts with an —SH group of a post-translationally modified peptide, a peptide, or a mixture thereof. The amine groups on the modified surface react with the heterobifunctional linker to provide the peptide attachment surface. In some embodiments, the surface modifying agent is an aminoalkyltrialkoxysilane, N-(2-aminoethyl)-3-aminopropyltrimethoxysilane, or m,p-(aminoethyl-aminomethyl) phenethyltrimethoxysilane. In some such embodiments, the aminoalkyltrialkoxysilane is 3-aminopropyltriethoxysilane.

Kits and optical cells for differentiating between post-translationally modified peptides and peptides are also provided. Such kits and optical cells may have any of the features described herein.

Further objects, features and advantages of the invention will be apparent from the following detailed description when taken in conjunction with the accompanying drawings.

BRIEF DESCRIPTION OF THE DRAWINGS

FIG. 5A is a schematic representation of a control experiment using anti-avidin antibodies and Src-tide peptide. FIG. 5B is a schematic representation of a control experiment using anti-avidin antibodies and (p)-Src-tide peptide. FIG. 8C is a schematic representation using anti-phosphotyrosine antibodies and Src-tide peptide. FIG. 5D is a schematic representation using anti-phosphotyrosine antibodies and (p)-Src-tide peptide.

FIG. 6A is a schematic representation using anti-phosphotyrosine antibodies and Src-tide peptide. FIG. 6B is a schematic representation using anti-phosphotyrosine antibodies and (p)-Src-tide peptide. FIG. 6C is a schematic representation of a control experiment using anti-avidin antibodies and Src-tide peptide. FIG. 6D is a schematic representation of a control experiment using anti-avidin antibodies and (p)-Src-tide peptide.

FIG. 8A-FIG. 8D are graphical representations of the results of studies showing detection of a phosphorylated peptide at peptide areal density of 1% using liquid crystal N-(4-methoxybenzylidene)-4-butylaniline (MBBA) using an anti-phosphotyrosine antibody as recognition reagent, and images were recorded at T=0 and T=15 hours, where FIG. 8A and FIG. 8B illustrate the results of controls, and FIG. 8C and FIG. 8D illustrate the results of addition of anti-phosphotyrosine antibody.

FIG. 9A-FIG. 9C are graphical representations of the results of studies showing direct detection of a phosphorylated peptide (kemptide, SEQ ID NO: 4). The SAM was 5% EG3-N, the angle of gold deposition was 40°, the liquid crystal was 5CB and the spots of peptide, phosphopeptide and SSMCC linker were images in an asymmetrical cell having an inert top surface, where FIG. 9A shows the results with SSMCC and (p)-kemptide (SEQ ID NO: 4), FIG. 9B shows the results with SSMCC and kemptide (SEQ ID NO: 3) and FIG. 9C shows the results with SSMCC without peptide.

FIG. 11A is a view of the array oriented so that the direction from which the gold was obliquely deposited is parallel to the source polarizer of the microscope. FIG. 11B is a view of the array oriented so that the direction from which the gold was obliquely deposited is 45° with respect to the source polarizer of the microscope.

FIG. 13A is a graphical representation of baseline corrected PM-IRRAS spectra of Src-tide peptides covalently bound to SAMs of an embodiment of the present invention, for SAMs formed of a mixture of EG3-N and EG3 thiols containing 1, 5, 10, 25, 50 or 100 percent EG3-N.

FIG. 13B is a graphical representation of baseline corrected PM-IRRAS spectra of (p)-Src-tide peptides covalently bound to SAMs of an embodiment of the present invention, for SAMs formed of a mixture of EG3-N and EG3 thiols containing 1, 5, 10, 25, 50 or 100 percent EG3-N.

FIG. 13C is a graphical representation of difference spectra highlighting the contribution of Src-tide peptides covalently bound to SAMs formed of a mixture of EG3-N and EG3 thiols containing 1, 5, 10, 25, 50 or 100 percent EG3-N.

FIG. 13D is a graphical representation of difference spectra highlighting the contribution of (p)-Src-tide peptides covalently bound to SAMs formed of a mixture of EG3-N and EG3 thiols containing 1, 5, 10, 25, 50 or 100 percent EG3-N.

FIG. 18A are schematic representations demonstrating the detection of a post-translationally modified peptide ((p)-Src-tide) using antibodies as the recognition reagent in conjunction with the nematic liquid crystal 5CB in an embodiment of the present invention. FIG. 18B shows optical polarization microscopy images of the nematic liquid crystal 5CB in contact with surfaces presenting peptide-modified SAMs having Src-tide and p-Src-tide peptides immediately after preparation. FIG. 18C shows optical polarization microscopy images of the same samples after annealing for 17 hours at 36° Celsius.

FIG. 19A illustrates diagrammatically a two dimensional array constucted using a 1% ED3–N SAM. FIG. 19B shows optical images of 5CB in contact with this peptide array, upon reaching equilibrium (17 hour annealing period) showing spots 310, 320, 330, 340 and 350. FIG. 19C is a histogram of the quantified mean luminosity of the spots.

FIG. 20A illustrates diagrammatically a two dimensional array constucted using a 0.5% ED3–N SAM. FIG. 20B shows optical images of 5CB in contact with this peptide array, upon reaching equilibrium (17 hour annealing period) showing spots 410, 420, 430, 440 and 450. FIG. 20C is a histogram of the quantified mean luminosity of the spots.

DETAILED DESCRIPTION OF THE INVENTION

Nematic liquid crystals are materials with mobilities characteristic of liquids yet are capable of organizing over distances of hundreds of micrometers. Past theoretical and experimental studies have established that the orientations of liquid crystals near an interface to a confining medium are dictated by the chemical and topographical structure of that interface. Methods to control the orientations of liquid crystals include using surfaces of solids with anisotropic topography prepared by oblique deposition of metals or lithographic processes. In addition, the orientations of liquid crystals can be affected by the chemical functional groups presented at interfaces via, for example, hydrogen bonding, presence of an electrical double layer and metal-ligand interactions. The macroscopic orientation of the terminal groups in a SAM formed on gold films prepared by oblique deposition can influence the directionality of these interactions and lead to preferred azimuthal orientations of liquid crystals near the interface. This so-called anchoring of liquid crystals by surfaces has found widespread use in the display industry and underlies the principles that are being developed for the detection of molecular and biomolecular events at interfaces: a change in the chemical or topographical structure of an interface brought about by a chemical or biological species at a surface can give rise to new orientations of liquid crystals in contact with that surface. As liquid crystals are birefringent, these new orientations can be visualized under simple polarized microscopy.

Figure 1:
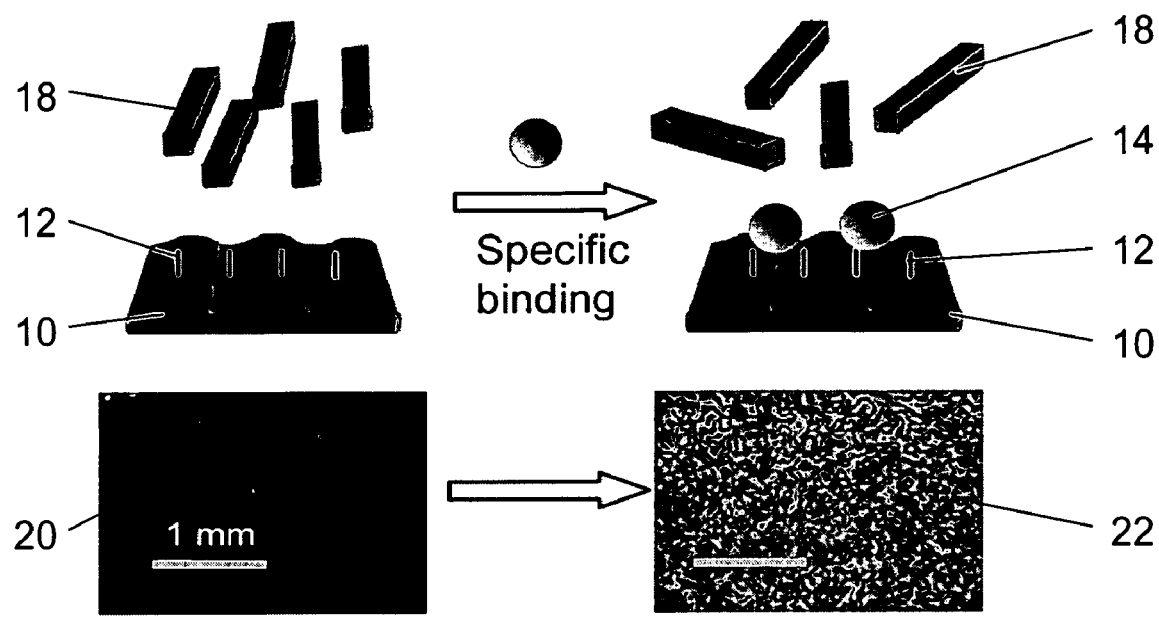
FIG. 1 is a schematic representation of an embodiment of the present invention, showing a substrate coated with a nano-structured gold film 10, surface immobilized peptides 12 and liquid crystal molecules 18, showing a change of orientation of liquid crystal molecules 18 due to specific binding of recognition reagent molecules 14 to immobilized peptide 12. Since liquid crystals are birefringent, the change in orientation of the liquid crystal molecules can be visualized using polarized microscopy, as illustrated by a comparison of images 20 and 22, where the scale bar indicates 1 mm.

FIG. 1 is a schematic representation of an embodiment of the present invention, showing a substrate coated with a nano-structured gold film 10, surface immobilized peptides 12 and liquid crystal molecules 18, showing a change of orientation of liquid crystal molecules 18 due to specific binding of recognition reagent molecules 14 to immobilized peptide 12. Since liquid crystals are birefringent, the change in orientation of the liquid crystal molecules can be visualized using polarized microscopy, as illustrated by a comparison of images 20 and 22, where the scale bar indicates 1 mm.

Figure 2:
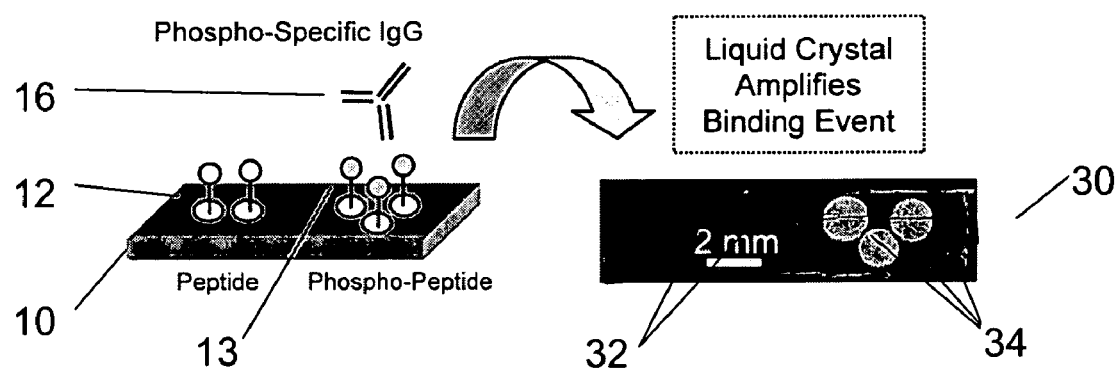
FIG. 2 is a schematic representation of a preferred embodiment of the present invention, showing a substrate coated with a nano-structured gold film 10, discretely localized surface immobilized peptides 12, surface immobilized post-translationally modified (phosphorylated) peptides 13 and where the recognition reagent molecules are phosphorylation-specific antibody molecules 16. An image of an array 30 having discretely localized multiple spots of peptide 32 and phosphorylated peptide 34 showing increased luminosity of the phosphorylated peptide spots 34 due to the change in orientation of the liquid crystal molecules caused by specific binding of the phosphorylation-specific antibody molecules to the surface immobilized phosphorylated peptides. The scale bar indicates 2 mm.

FIG. 2 is a schematic representation of a preferred embodiment of the present invention, showing a substrate coated with a nano-structured gold film 10, discretely localized surface immobilized peptides 12, surface immobilized post-translationally modified (phosphorylated) peptides 13 and where the recognition reagent molecules are phosphorylation-specific antibody molecules 16. An image of an array 30 having discretely localized multiple spots of peptide 32 and phosphorylated peptide 34 showing increased luminosity of the phosphorylated peptide spots 34 due to the change in orientation of the liquid crystal molecules caused by specific binding of the phosphorylation-specific antibody molecules to the surface immobilized phosphorylated peptides. The scale bar indicates 2 mm.

In preferred embodiments, the methods of the present invention can be used to manipulate the areal density of surface-immobilized peptides on nano-structured gold films so as to achieve control over the orientation of liquid crystals on these surfaces. The nanometer-scale topography of these films is introduced using physical vapor deposition of gold at an oblique angle of incidence. These films have been previously shown using AFM to have corrugations with an amplitude of about 3-5 nm and a wavelength of about 30 nm.

In preferred embodiments of the present invention, a peptide sequence that is a known substrate for enzyme is immobilized on a nano-structured gold films. In such preferred embodiments, the peptide is a substrate of an enzyme that is a member of a signalling pathway. In certain preferred embodiments, the peptide is a substrate for the Src protein kinase. The Src protein kinase has broad biological importance, as it is implicated in aggressive forms of colon and breast cancer and plays a role in the focal adhesion contact formation of migrating cells.

Since liquid crystals are sensitive to both the chemical functionality and topography of an interface, care must be taken to control of areal density and site-selectivity of the immobilized peptide. In preferred embodiments, cysteine-terminated peptides and their reactions with surface-immobilized maleimide groups are used. Similarly, the density of presented maleimide groups (leading to controlled densities of immobilized peptides) can be controlled. In preferred embodiments, the presence of specific binding of the protein anti-phosphotyrosine immunoglobulin G (IgG) to the surface-immobilized phosphorylated peptide, p-Src-tide, leads to detectable changes in the ordering of a nematic liquid crystal in contact with these peptide-modified surfaces.

Generally, the invention provides devices and methods for differentiating between post-translationally-modified peptides and peptides on surfaces using liquid crystals. The invention also generally provides methods for preparing liquid crystal devices for differentiating between post-translationally modified peptides and peptides.

The term "peptide" refers to a compound comprising two or more amino acid groups joined together through peptide bonds in which the carboxylic acid group of one amino acid reacts with an amine group of a second amino acid to form the amide peptide bond. For the purposes of this document, the term "peptide" does not include a "post-translationally-modified peptide". A protein is a type of "peptide."

The term "post-translationally modified peptide" refers to a peptide which has been modified following synthesis or to a synthetic peptide which is identical in composition to such a modified peptide. In some cases, "post-translationally modified peptide" refers to a peptide in which an amino acid residue of the peptide has been chemically modified. In other cases, "post-translationally modified peptide" refers to a peptide from which one or more amino acids have been cleaved following synthesis. For purposes of this document, a "post-translationally modified peptide" includes natural and synthetic peptides in which an amino acid residue has been modified such as, but not limited to, by being phosphorylated, acylated (e.g. acetylated, palmitoylated, etc.), glycosylated, adenylated, farnesylated, or alkylated (e.g. methylated) or by being proteolytically cleaved. Examples of phosphorylated peptides include those in which a tyrosine, serine, threonine, or histidine residue has been phosphorylated.

The term "peptide attachment surface" refers to a surface to which post-translationally modified peptides and peptides will be attached when contacted therewith. Further properties of the peptide attachment surface are set forth below.

The term "peptidized surface" refers to a peptide attachment surface of the invention which has been contacted with a post-translationally modified peptide, a peptide, or a mixture thereof such that the post-translationally modified peptide, the peptide, or the mixture of the post-translationally modified peptide and the peptide are attached to the peptide attachment surface.

The term "recognition reagent" refers to a compound that selectively binds to or complexes with a post-translationally modified peptide or a group on the post-translationally modified peptide. Examples of recognition reagents include, but are not limited to, antibodies, antibody fragments, and cationic compounds. Other examples of recognition reagents include, but are not limited to, antibodies, antibody fragments, cationic surfactants, polyelectrolytes, cationic iron compounds, and phosphosensor dyes. In some embodiments, the recognition reagent is an antibody or antibody fragment that selectively binds or forms a complex with a phosphorylated peptide. In some embodiments, the recognition reagent is a cationic iron compound that selectively binds or forms a complex with the phosphate group of a phosphorylated peptide.

The term "about" as used herein in conjunction with a number refers to a range of from 95% to 105% of that number. For example a temperature of about 60° C. refers to a temperature ranging from 57° C. to 63° C.

All ranges recited herein include all combinations and subcombinations included within that range's limits. For example, a percentage range of from about 20% to about 65% includes ranges of from 20% to 60%, of from 25% to 30%, of from 25% to 28%, and of from 20% to 30%, etc. Furthermore, one skilled in the art will recognize that any listed range can be easily recognized as sufficiently describing and enabling the same range being broken down into at least equal halves, thirds, quarters, fifths, tenths, etc. As a non-limiting example, each range discussed herein can be readily broken down into a lower third, middle third, and upper third.

A wide variety of materials may be used as supports to prepare devices for differentiating between post-translationally modified peptides and peptides in the devices and methods of the present invention as will be apparent to those skilled in the art. Preferred supports include polymers and silica-containing materials. Examples of polymeric supports include, but are not limited to, polystyrene, polycarbonates, and polymethyl methacrylate. Other materials suitable for use as supports include metal oxides such as, but not limited to, indium oxide, tin oxide, and magnesium oxide and metals such as, but not limited to, gold, silver, titanium, and platinum. Still other materials that may be used as supports include cellulosic materials such as nitrocellulose, wood, paper, and cardboard, and sol-gel materials. In some embodiments, supports include glass, quartz, and silica or silicon, or more preferably, glass slides, glass plates, and silica or silicon wafers. Preferably, such supports are cleaned prior to use. For example, glass slides and plates are preferably cleaned by treatment in "piranha solution" (70% $H_2SO_4$/30% $H_2O_2$) for 1 hour and then rinsed with deionized water before drying under a stream of nitrogen. "Piranha solution" requires care in handling as it reacts violently with organic compounds and should not be stored in closed containers.

A preferred support in accordance with the present invention possesses a top surface with a layer of a metal overlying it to create a metallized surface. In some embodiments, the metal is obliquely deposited over the surface of the support. Metals that may be used include, but are not limited to, gold, silver, copper, platinum, and palladium. Optionally, an obliquely deposited metal surface such as a gold or silver surface will overlay a surface of titanium or other material that promotes adhesion which has already been deposited on a top surface of the support. The use of such a material provides better adhesion of the obliquely deposited metal such as silver, or more preferably gold in preparing the metallized surface. Chromium and organic adhesion promoters, such as, but not limited to, aminopropyltrialkoxysilanes may also be utilized in accordance with the present invention. The use of titanium or another adhesion-promoting material is not required as suitable surfaces for differentiating between post-translationally modified peptides and peptides may be prepared without the use of such materials. If an adhesion promoting material is used, a layer of varying thickness may be applied to the underlying support. In some embodiments, about 10 Å (1.0 nm) of Ti is deposited on a support such as a glass slide or plate. In other embodiments, the amount of adhesion-promoting material ranges from 5 A (0.5 nm) or about 5 Å (0.5 nm) to 20 A (2.0 nm) or about 20 Å (2.0 nm) while in other embodiments the thickness ranges from 8 Å (0.8 nm) or about 8 Å (0.8 nm) to 15 Å (1.5 nm) or about 15 Å (1.5 nm). In some embodiments, approximately 10 Å (1.0 nm) of aminopropyltrimethoxy-silane is deposited as an adhesion-promoting material. In other embodiments, the thickness of the layer of adhesion promoting material ranges from 5 Å (0.5 nm) or about 5 Å (0.5 nm) to 50 Å (5 nm) or about 50 Å (5 nm). The amount of adhesion-promoting material may be thicker such that in some embodiments, the thickness of the layer of an adhesion-promoting material such as titanium ranges from 5 Å (0.5 nm) or about 5 Å (0.5 nm) to 100 Å (0 nm) or about 100 Å (10 nm).

In some embodiments, a layer of an obliquely deposited metal, preferably gold, is deposited on a cleaned surface of the support by evaporating it at a rate of about 0.2 Å/s (0.02 nm/s) at a pressure of less than or about $5 \times 10^{-6}$ torr without rotation of the sample relative to the incident flux of gold. See Gupta, V. K. et al. *Chemistry of Materials,* 8, 1366 (1996) which is hereby incorporated by reference herein in its entirety and for all purposes as if fully set forth herein. In other embodiments, a metal such as gold is deposited as described above on a top surface of a support that contains an adhesion-promoting material such as titanium. The layer of a metal such as gold on the metallized surface of the support typically ranges from 50 Å (5 mm) or about 50 Å (5 nm) to 300 Å (30 nm) or about 300 Å (30 nm) in thickness. In other embodiments, the layer of a metal such as gold deposited on the surface of the support ranges from 80 Å (8 mm) or about 80 Å (8 nm) to 250 Å (25 nm) or about 250 Å (25 nm) in thickness or from 90 Å (9 nm) or about 90 Å (9 nm) to 200 Å (20 mm) or about 200 Å (20 nm) in thickness. In still other embodiments, the layer of the metal such as gold deposited on the support is from 100 Å (10 nm) or about 100 Å (10 nm) to 200 Å (20 nm) or about 200 Å (20 nm). In some embodiments, a metal such as gold is deposited at an angle of from 30° or about 30° to 60° or about 60°. In other preferred embodiments, a metal such as gold is deposited at an angle of 50° or about 50°. In still other embodiments, the gold is deposited at an angle of from 30° or about 30° to 50° or about 50°. In still other embodiments the gold is deposited at an angle of from 40° or about 400 to 50° or about 50°. In yet other embodiments, the deposition angle is 40° or about 40° or 45° or about 45°. The angle at which the gold is deposited on an underlying support may impact the sensitivity of the surface for detecting phosphorylated peptides. Therefore, different angles of metal deposition may be preferred depending on the particular application as will be apparent to those skilled in the art. The metallized surface obtained after deposition of the metal is generally an anisotropically rough and semi-transparent surface.

A self-assembled monolayer (SAM) in accordance with the invention may be formed on a metallized surface that overlies a support by contacting the metallized surface with a first thiol compound and/or a second thiol compound. The first thiol compound and the second thiol compound both possess —SH groups or equivalents thereof such as a disulfide linkage such that the first and second thiol compounds are adsorbed onto the metallized surface when contacted with a solution that includes these compounds. The molar ratio of the first thiol compound to the second thiol compound may be adjusted to provide SAMs with a desired molar ratio of the first thiol compound to the second thiol compound. In some embodiments, the molar ratio of the first thiol compound to the second thiol compound in such a solution ranges from 0.1:99.9 to 50:50. In other embodiments, the molar ratio of the first thiol compound to the second thiol compound ranges from 0.1:99.9 to 20:80, from 0.1:99.9 to 10:90, from 0.1:99.9 to 5:95, from 0.1:99.9 to 2:98, from 0.1:99.9 to 1:99, from 0.1:99.9 to 0.5:99.5, from 0.2:99.8 to 50:50, from 0.2:99.8 to 20:80, from 0.2:99.8 to 10:90, from 0.2:99.8 to 5:95, from 0.2:99.8 to 2:98, from 0.2:99.8 to 1:99, from 0.2:99.8 to 0.5:99.5, from 0.5:99.5 to 50:50, from 0.5:99.5 to 20:80, from 0.5:99.5 to 10:90, from 0.5:99.5 to 5:95, from 0.5:99.5 to 2:98, from 0.5:99.5 to 1:99, 1:99 to 50:50, from 1:99 to 20:80, from 1:99 to 10:90, from 1:99 to 5:95, or from 1:99 to 2:98. In other preferred embodiments, the molar ratio of the first thiol compound to the second thiol compound is about 1:99, about 5:95, about 10:90, about 25:75, about 50:50 or 100:0.

In some embodiments, the first and second thiol compounds may be adsorbed on the metallized surface from a solution. A metallized surface may be contacted with such an adsorption solution by placing a drop on all or a part of the surface or by immersing the entire metallized surface in the adsorption solution. Solutions with varying or the same molar ratios of the first thiol compound to the second thiol compound may be spotted onto two, three, four, five, six, or a plurality of different portions of a metallized surface to provide a metallized surface in which there are portions with either different or the same molar ratios of the fist thiol compound to the second thiol compounds. Such surfaces may be formed which have a gradient in the molar ratio of the first thiol to the second thiol compound.

The concentration of the first and second thiol compounds in the solution used for adsorption generally range from about 1 micromolar to 10 millimolar. When using 1 micromolar solutions, preferred immersion times range from 10 seconds to 24 or more hours. Particularly preferred immersion times are those ranging from 6 hours to 24 hours, from 12 hours to 24 hours, or for more than 24 hours. Typically, SAMs are prepared by contacting the metallized surface of a support with an alcohol solution including the first and second thiol compounds at a concentration of 0.1 mM for a period of about 12 hours or more. In some embodiments, the alcohol solution is an ethanol or methanol solution. Longer or shorter contact times may be used as long as a densely packed monolayer is obtained as will be apparent to those of skill in the art. Generally, the lower the total concentration of the first and second thiol compounds in the adsorption solution, the longer the metallized surface will be contacted with the adsorption solution. Conversely, the higher the total concentration of the first and second thiol compounds in the adsorption solution, the shorter the metallized surface will be contacted with the first and second thiol compounds.

The first and second thiol compounds are typically adsorbed onto the metallized surface of the support in solutions at temperatures ranging from about 15° C. to about 60° C., from about 20° C. to about 40° C., from about 22° C. to about 40° C., or from about 25° C. to about 37° C. In some embodiments, the temperature range is from about 22° C. to about 28° C., and in other embodiments the temperature is about 25° C. A steady temperature is not necessary, and the temperature may be increased or decreased during the adsorption. Generally, the temperature of the adsorption solution is not critical to the preparation of the formation of the self-assembled monolayer. The first and second thiol compounds are normally contacted with the metallized surface for periods of at least 12 hours, but longer or shorter contact times may be suitable depending on the concentration of the thiol compounds in the solution.

Various first thiol compounds may be used to prepare the SAMS on the metallized surfaces of the support. Those skilled in the art will recognize that disulfides or compounds having a disulfide linkage (an S—S bond) may also be used in place of a compound having a —SH group to prepare such surfaces. Such compounds may be termed the disulfide equivalent of the thiol. A disulfide equivalent of a thiol may be drawn by drawing two of the thiols, removing the H from each of the S atoms and then drawing a bond from one of the S atoms to the other of the different thiols. For example, the disulfide equivalent of a thiol of formula R—S—H is R—S—S—R. In addition to the —SH or disulfide linkage, a first thiol compound for use in the reaction includes a functional group that reacts with a heterobifunctional linker. Examples of such groups include amine or ammonium groups. In some embodiments, the first thiol compound is a compound of formula HS—$(CH_2)_a$—$(OCH_2CH_2)_b$—$NH_2$, an ammonium salt thereof, or is a disulfide equivalent thereof where a is an integer ranging from 1 to 30, or in some embodiments ranging from 4 to 22, and b is an integer ranging from 0 to 10, or in some embodiments ranging from 1 to 5. In some such embodiments, the first thiol compound is a compound of formula HS—$(CH_2)_{11}(OCH_2CH_2)_3NH_2$, an ammonium salt thereof, or a disulfide equivalent thereof.

Various second thiol compounds may be used to prepare the SAMS on the metallized surfaces of the support. Again, those skilled in the art will recognize that disulfides or compounds having a disulfide linkage may also be used in place of a compound having a —SH group to prepare such surfaces. In addition to the —SH or disulfide linkage, a second thiol compound for use in the reaction includes an —OH, an alkoxy group, a $CH_3$, a sugar, a zwitterionic group, or a polar non-ionic group. In some embodiments, the second thiol compound is a compound of formula HS—$(CH_2)_c$—$(OCH_2CH_2)_d$—X, wherein c is an integer ranging from 1 to 30, or in some embodiments ranging from 4 to 22, and d is an integer ranging from 0 to 10, or in some embodiments ranging from 1 to 5, and X is selected from an —OH, an alkoxy group, a $CH_3$, a sugar, a zwitterionic group, or a polar non-ionic group. In some embodiments, the second thiol compound is a compound of formula HS—$(CH_2)_c$—$(OCH_2CH_2)_d$—OH or is a disulfide equivalent thereof where c is an integer ranging from 1 to 30, or in some embodiments ranging from 4 to 22, and d is an integer ranging from 0 to 10, or in some embodiments ranging from 1 to 5. In some such embodiments, the second thiol compound is a compound of formula HS—$(CH_2)_{11}(OCH_2CH_2)_3OH$ or a disulfide equivalent thereof. In other embodiments, the second thiol comprises an —$OCH_3$ group and an —OH group and an —SH group, wherein the —SH group of the second thiol compound is attached to the first portion of the top surface of the metallized surface. In still other embodiments, the second thiol has the formula HS$(CH_2)_{10}$R where R is $CH_3$, $CH_2OH$, or oligo(ethylene oxide) as described in Prime, K. L. and Whitesides, G. M., *J. Am. Chem. Soc.* 115:10714-10721 (1993) which is hereby incorporated by reference in its entirety and for all purposes as if fully set forth herein.

Further chemistries for the covalent attachment of peptides to SAMs are known in the art, and can be used in the practice of the present invention. Such strategies are reviewed in detail in Love, J. C., Self-assembled monolayers of thiolates on metals as a form of nanotechnology, Chem. Rev. 2005, 105: 1103-1169, which is incorporated by reference herein in its entirety. In certain embodiments, the SAMs present terminal functional groups selected from the group consisting of amines, hydroxyls, carboxylic acids, aldehydes and halogens. See Love et al., 2005, pp. 1124-1127. In certain embodiments, the thiols in the SAM present terminal azides that react with peptides bearing a acetylene group ("click" chemistry). In further embodiments, the thiols in the SAM present terminal azides that react with peptides bearing a substituted phosphane group (Staudinger reaction). Alternative reactions are known for covalently linking appropriately modified peptides to thiols having terminal functional groups such as amines, azides, hydroxyls, —CONHR groups, aldehydes and halogens.

Functional groups attached to peptides are chosen to react with the terminal functional groups of the thiols in the SAMs. In preferred embodiments, a functional —SH group is obtained by the presence of a cysteine residue. In further embodiments, the peptide has a functional group selected from the group consisting of disulfide, acrylamide, acyrlic acid, methyl acrylate, acetylene, substituted phosphanes and amines.

After the first and/or second thiol compounds have been adsorbed onto the metallized surface of the support, the surface of the support is typically rinsed with ethanol or some other suitable solvent. The surface may then be rinsed with water or another suitable solvent. After rinsing, the surface is typically dried such as by blowing a stream of $N_2$ or other inert gas over the rinsed surface. Such a surface is then generally contacted with a heterobifunctional linker to provide a peptide attachment surface. The heterobifunctional linker includes a functional group such as, in some embodiments, a maleimide group, that reacts with an —SH group, such as on a cysteine amino acid residue, on a post-translationally modified peptide or peptide to produce a surface to which these may be attached otherwise referred to as a peptide attachment surface.

Various heterobifunctional linkers may be used in accordance with the invention. A heterobifunctional linker possesses one functional group that reacts with a group on the first thiol to form a functionalized thiol. The heterobifunctional linker also possesses a functional group, such as, but not limited to, a maleimide that will react with a —SH group on a post-translationally modified peptide or a peptide. In one embodiment, the heterobifunctional linker is sulfosuccinimidyl-4-(N-maleimidomethyl)cyclohexane-1-carboxylate (SSMCC), a compound having the following formula:

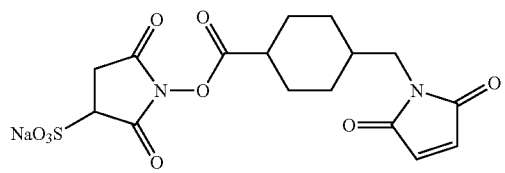

Examples of other suitable heterobifunctional linkers include, but are not limited to, the following, described in Xiao, S-J., et al., *Langmuir* 14: 5507-5516 (1998): N-succinimidyl-6-maleimidylhexanoate (EMCS), N-succinimidyl-3-maleimidylpropionate (SMP), both available from Fluka, Buchs, Switzerland; and N-succinimidyl trans-4-(maleimidylmethyl)cyclohexane-1-carboxylate (SMCC) (Molecular Probe, Netherlands). In some embodiments, the heterobifunctional linker includes a functional group that will react with an amine or ammonium group of a first thiol and the functional group that will react with the post-translationally modified peptide or peptide. Reaction of the heterobifunctional linker with the first thiol compound attached to the metallized surface produces a functionalized thiol compound that will react with post-translationally modified peptides and/or peptides to provide a peptidized surface. For example, a heterobifunctional linker such as SSMCC will react with a first thiol compound of formula HS—$(CH_2)_a$—$(OCH_2CH_2)_b$—$NH_2$, an ammonium salt thereof, or a first thiol compound of formula HS—$(CH_2)_{11}(OCH_2CH_2)_3NH_2$ or an ammonium salt thereof bound to the metal to provide the following functionalized thiol compounds:

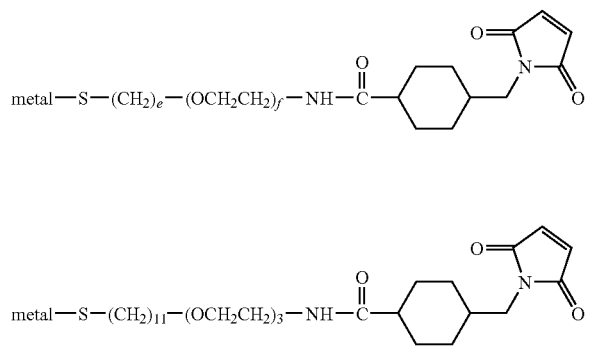

where e is an integer ranging from 1 to 30, or in some embodiments ranging from 4 to 22, and f is an integer ranging from 0 to 10, or in some embodiments ranging from 1 to 5.

Reaction of the heterobifunctional linker with the attached first thiol compound is typically accomplished by contacting the surface having the attached first thiol compound with the heterobifunctional linker. For example, a surface comprising an attached first thiol compound may be immersed in a solution comprising a heterobifunctional linker such as SSMCC or alternatively such as solution may be spotted onto the surface to provide a peptide attachment surface. In one embodiment, a solution of SSMCC in a buffered solution is applied to the self-assembled monolayer and incubated in the dark for 45 minutes resulting in a chemical reaction between the first thiol compound and the heterobifunctional linker. Various solutions and buffers may be used in accordance with the invention. In one embodiment, a 2 mM solution of a heterobifunctional linker is prepared in a 0.1 M triethanolamine buffered solution (pH of 7.0). Other solutions may be used as will be recognized by those of skill in the art.

The use of a second thiol compound is not required in the devices and methods of the present invention. In some embodiments, a metallized surface is reacted with a first thiol compound to produce a surface with terminal amine groups. Reaction of the terminal amine groups with a measured amount of heterobifunctional linker provides a surface with some free amine groups and with some groups with a reactive site for peptide attachment. Control of the amount of heterobifunctional contacted with the surface provides one method for controlling the peptide density on the surface. In another embodiment, the surface is contacted with the heterobifunctional linker such that the majority, if not all, of the terminal amine groups on the surface are reacted with the heterobifunctional linker. The peptide density on such a surface may be controlled by various methods. In one embodiment, a solution of a peptide, a post-translationally modified peptide, or mixture thereof with a calculated quantity of the peptide, post-translationally modified peptide, or mixture thereof is contacted with the peptide attachment surface and then the resulting surface is contacted with a thiol compound such as 2-mercaptoethanol to react with the remaining unreacted maleimide groups. In another embodiment, a solution with a calculated amount of a peptide, post-translationally modified peptide, or mixture thereof and a thiol compound such as 2-mercaptoethanol is contacted with the peptide attachment surface to provide a controlled peptide density on the peptidized surface.

In some embodiments, a glass, silica, silicon, titania, titanium, alumina, or aluminum surface is used. These surfaces are modified to present terminal amines by various methods known to those skilled in the art, including but not limited to methods described in Charles et al., *Langmuir* 19: 1586-91 (2003). For example a surface modifying agent that includes an amine group and a group that reacts with the surface, such as with a hydroxyl group present on a glass surface, may be contacted with a surface to provide a modified surface that present amine groups for further reaction with a heterobifunctional linker of the invention. Surface modifying agents include compounds such as, but not limited to, aminoalkyltrialkoxysilanes such as, but not limited to, 3-aminopropyltriethoxysilane (APES), 3-aminopropyltrimethoxysilane, 4-aminobutyltrimethoxysilane, and 4-butyltriethoxysilane; N-(2-aminoethyl)-3-aminopropyltrimethoxysilane; or m,p-(aminoethyl-aminomethyl) phenethyltrimethoxysilane (*Langmuir* 19: 1586-1591 (2003)), herein incorporated by reference in its entirety. Examples of aminoalkyltrialkoxysilanes include compounds of formula $H_2N$—$(CH_2)_q$—$Si(OR')_3$ where q is an integer having a value of from 2 to 25 such as in some embodiments, 2, 3, 4, 5, 6, 7, 8, 9, 10, 11, 12, 13, 14, 15, 16, 17, 18, 19, 20, 21, or 22 and the three R' groups are independently alkyl groups having from 1 to 6 carbon atoms such as methyl, ethyl, propyl, butyl, pentyl, hexyl, heptyl, or octyl. In some embodiments a halosilane such as a chlorosilane that is equivalent to the aminoalkyltrialkoxysilane is used as the surface modifying agent. The terminal amines on modified surfaces may then be reacted or contacted with a solution of a heterobifunctional linker such as, but not limited to, SSMCC, as described above, to provide a peptide attachment surface followed by contact with peptides, post-translationally modified peptides or mixtures thereof or mixtures of these and a second thiol such as EG-3 or those other second thiol compounds described above to provide a peptidized surface. The peptide density on such a surface may be controlled by various methods. In one embodiment, a solution of a peptide, a post-translationally modified peptide, or mixture thereof with a calculated quantity of the peptide, post-translationally modified peptide, or mixture thereof is contacted with the peptide attachment surface and then the resulting surface is contacted with a thiol compound such as 2-mercaptoethanol to react with the remaining unreacted maleimide groups. In another embodiment, a solution with a calculated amount of a peptide, post-translationally modified peptide, or mixture thereof and a thiol compound such as 2-mercaptoethanol is contacted with the peptide attachment surface to provide a controlled peptide density on the peptidized surface. Such surfaces may then be incubated with a recognition reagent as described above and contacted with a liquid crystal. Alternatively, a peptide on a peptidized surface may be modified and the resulting surface may then be incubated with a recognition reagent and then contacted with a liquid crystal.

A peptidized surface may be prepared by contacting a peptide attachment surface of the invention with a post-translationally modified peptide, a peptide, or a mixture thereof. For example, a solution of peptide, post-translationally modified peptide, or a mixture thereof may be applied to a peptide attachment surface. The concentration of the peptide, post-translationally modified peptide, or mixture thereof may vary considerably as may the temperature of the reaction. In one embodiment, a 250 micromolar solution of the peptide, post-translationally modified peptide, or mixture thereof is applied to a peptide attachment surface that includes a reactive maleimide group and incubated for 3 hours to provide a peptidized surface where the peptide, post-translationally modified peptide, or mixture thereof is bonded to the peptide attachment surface through a reaction of the maleimide group with the —SH group of a cysteine residue. Such solutions may include a buffer as described above such as triethanolamine. After contacting the peptide attachment surface with the peptide, post-translationally modified peptide, or mixture thereof, the peptidized surface is typically rinsed with a suitable solvent or solution and quenched to remove all non-reacted functional groups on the functionalized thiol. For example, a peptidized surface may be rinsed with a triethanolamine solution containing Triton-X 100 one or more times. The resulting rinsed surface may then be treated with a quenching agent such as 2-mercaptoethanol which will react with any unreacted maleimide groups on the peptidized surface. Further rinsing of the quenched surface may be accomplished using a suitable solvent such as water or an alcohol. The surface may then be dried such as by flowing a stream of $N_2$ over or at the surface. As further described herein, in some embodiments, peptides and post-translationally modified peptides may be attached to the peptide attachment surface at different densities using procedures such as, but not limited to, in a density gradient. In other embodiments, the molar ratio of the first thiol compound to the second thiol compound may vary on different portions of a peptide attachment surface. This will allow the amount of peptide, post-translationally modified peptide, or mixture thereof attached to a portion of the surface to be controlled when the peptide attachment surface is contacted with these.

A peptidized surface is generally incubated with a recognition reagent for use in differentiating between post-translationally modified peptides and peptides. As noted below, in some embodiments, this is not accomplished as the orientation of a liquid crystal on a peptidized surface may allow for the direct detection of a post-translationally modified peptide without the need for a recognition reagent. Furthermore, in some embodiments, a peptide on a peptidized surface may be post-translationally modified after attachment to a peptide attachment surface and then incubated with a recognition reagent of the invention as described in Houseman, B. T. et al., *Nature Biotechnology*, 20: 270-274 (2002). Such embodiments allow a user to determine whether a peptide on a peptidized surface has been modified by a particular reagent. Post-translational modification may be accomplished using various methods such as, but not limited to, by contacting a peptide with a kinase, such as, but not limited to, a tyrosine kinase, a serine kinase, a threonine kinase, or a histidine kinase. In some embodiments, a peptidized surface is contacted with a recognition reagent to provide an incubated surface. Suitable recognition reagents are those that selectively bind or form a complex with the post-translationally modified peptide or bind or form a complex with a functional group on the post-translationally modified peptide. Examples of such recognition reagents, include, but are not limited to antibodies, antibody fragments, and cationic compounds. Examples of such recognition reagents, also include, but are not limited to antibodies, antibody fragments, a cationic surfactant, a polyelectrolyte, a cationic iron compound, or a phosphosensor dye that selectively binds or forms a complex with a phosphate group on the phosphorylated peptide. In some embodiments, the post-translationally modified peptide is a phosphorylated peptide and the recognition reagent is an antibody or antibody fragment that selectively binds or forms a complex with the phosphorylated peptide. The ability to detect phosphorylated tyrosine, serine, and threonine residues in post-translationally modified peptides means that the devices and methods of the present invention have important applications in drug-screening and activity assays.

A peptidized surface is generally incubated with the recognition reagent by contacting the peptidized surface with a solution comprising an appropriate recognition reagent depending on the type of possible post-translationally modified peptide. For example, in one embodiment, a peptidized surface is contacted with a solution of an antibody specific for a phosphorylated peptide such as an antibody specific for phospo-tyrosine. The concentration of the recognition reagent and the temperature of such a solution may vary in accordance with the methods of the invention (for example, a peptidized surface may be incubated at temperature ranges including, but not limited to, from 20° C. to 45° C., from 22° C. to 40° C., from 25° C. to 38° C., and in some embodiments at about 36° C. and such a surface may be further incubated at such temperatures after it has been contacted with the liquid crystal) and the solution may be buffered using a variety of buffers or buffering systems. In one embodiment, a peptidized surface is contacted with a phosphate buffered saline (PBS) solution at pH 7 that includes Triton-X and about 10 micrograms per mL of an antibody specific for phospho-tyrosine. While the contact time may vary considerably depending on the type and concentration of recognition reagent, in one embodiment the peptidized surface is incubated with the recognition reagent for 1.5 hours at room temperature. After incubation, the incubated surface may be washed and dried prior to contact with the liquid crystal although this may not be required. In one embodiment, a surface incubated as described above is washed for about 15 seconds with a PBS solution containing Triton-X, rinsed with water, and is then dried under a stream of $N_2$. Kits may include one or more recognition reagent(s) and a peptide attachment surface allowing a user to prepare a peptidized surface according to their own requirements which can then be used with the appropriate recognition reagent. Such kits may also include instructions for preparing a peptidized surface, for selecting an appropriate recognition reagent, and for differentiating between a post-translationally modified peptide and a peptide. Such kits may further include a liquid crystal for use in detecting the post-translationally modified peptide.

After a peptidized surface has been incubated with a suitable recognition reagent, the resulting incubated surface is typically contacted with a liquid crystal and viewed using polarized light such as with a polarized microscope so that the presence of post-translationally modified peptides can be detected. Various liquid crystals may be used in accordance with the invention as described in greater detail below. In some embodiments, the incubated surface is paired with a second surface to form an optical cell, and the second surface uniformly anchors the liquid crystal. In such embodiments, the liquid crystal is typically located on the surface of the incubated surface and between the incubated surface and the second surface of the optical cell. Such a sandwich cell, in some embodiments, may be prepared by placing two identically-functionalized incubated surfaces face to face. The two surfaces may be separated using a spacer, and the cell may then be filled with a liquid crystal such as 5CB. In some embodiments, differentiation between the post-translationally modified peptide and the peptide is accomplished using a non-optical method such as, but not limited to, by measuring a dielectric property, using an evanescent optical method, and/or by measuring the optical absorbance.

Various types of liquid crystals may be used in conjunction with the present invention. Examples of these include both nematic and smectic liquid crystals. Other classes of liquid crystals that may be used in accordance with the invention include, but are not limited to: polymeric liquid crystals, thermotropic liquid crystals, lyotropic liquid crystals, columnar liquid crystals, nematic discotic liquid crystals, calamitic nematic liquid crystals, ferroelectric liquid crystals, discoid liquid crystals, and cholesteric liquid crystals. Examples of just some of the liquid crystals that may be used are shown in Table 1. In some embodiments the liquid crystal is a nematic liquid crystal such as 4-pentyl-4'-cyanobiphenyl (5CB).

TABLE 1

4-pentyl-4'cyanobiphenyl
5CB

Molecular Structure of Mesogens Suitable for use in Differentiating Post-Translationally Modified Peptides from Peptides.

| Mesogen | Structure |
|---|---|
| Anisaldazine | $CH_3-O-\bigcirc-CH=N-N=CH-\bigcirc-O-CH_3$ |
| NCB | $C_nH_{2n+1}-\bigcirc-\bigcirc-CN$ |
| CBOOA | $C_9H_{19}-O-\bigcirc-N=CH-\bigcirc-CN$ |
| Comp A | $C_7H_{15}-\bigcirc-\bigcirc-COO-\bigcirc-NCS$ |
| Comp B | $C_8H_{17}-O-\bigcirc-O-CO-\bigcirc-O-CH_2-\bigcirc-CN$ |
| $DB_7NO_2$ | $C_7H_{15}-\bigcirc-O-CO-\bigcirc-O-CO-\bigcirc-NO_2$ |
| DOBAMBC | $C_{10}H_{21}-O-\bigcirc-CH=N-\bigcirc-CH=CH-COO-CH_2-CH\begin{array}{c}CH_3\\C_2H_5\end{array}$ |
| nOm<br>n = 1, m = 4: MBBA<br>n = 2, m = 4: EBBA | $C_nH_{2n+1}-O-\bigcirc-CH=N-\bigcirc-C_mH_{2m+1}$ |
| nOBA<br>n = 8: OOBA<br>n = 9: NOBA | $C_nH_{2n+1}-O-\bigcirc-COOH$ |
| nmOBC | $C_nH_{2n+1}-O-CO-\bigcirc-\bigcirc-O-C_mH_{2m+1}$ |
| nOCB | $C_nH_{2n+1}-O-\bigcirc-\bigcirc-CN$ |

TABLE 1-continued

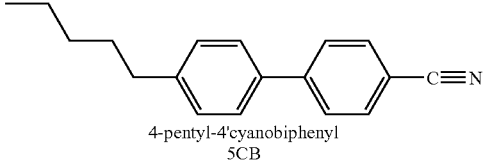

Molecular Structure of Mesogens Suitable for use in Differentiating Post-Translationally Modified Peptides from Peptides.

EXAMPLES

The following materials and methodologies were utilized in the examples discussed in greater detail below.

Materials

Glass microscope slides used in the experiments were marked premium grade and obtained from Fisher Scientific (Pittsburgh, Pa.). Glass slides were cleaned prior to use by sequential treatments with acidic "piranha solution" (70% $H_2SO_4$/30% $H_2O_2$) and basic "piranha solution" (80% KOH, 20% $H_2O_2$). "Piranha solution" should be handled with extreme caution because it reacts violently with organic materials and should not be stored in closed containers. After cleaning for 1 hour at 80° C. in acidic "piranha solution", the slides were rinsed copiously in deionized water and cleaned for 30 minutes at 80° C. in basic "piranha solution". Slides were then rinsed with copious amounts of deionized water, followed by ethanol, then by methanol, and then dried under a stream of nitrogen. Prior to use, the clean substrates were stored in an oven heated at 120° C. for at least 3 hours. The nematic liquid crystal, 4-cyano-4'-pentylbiphenyl, manufactured by BDH was purchased from EM industries (Hawthorne, N.Y.). The nematic liquid crystal MBBA (N-(4-methoxybenzylidene)-4-butylaniline) is available from Aldrich (Milwaukee, Wis., Product No. 158224).

Polarized Light Microscopy

A polarized light microscope (BX60, Olympus, Tokyo, Japan) was used to observe the optical textures formed by light transmitted through the optical cells filled with 5CB. All images were obtained using a 4× objective lens with a 1 mm field of view between crossed-polarizers. Images of the optical appearance of liquid crystal optical cells prepared from the peptidized or incubated surfaces were captured with a digital camera (C-2020 Z, obtained from Olympus America Inc. (Melville, N.Y.)) that was attached to the polarized light microscope. The pictures were obtained using high quality mode (resolution of 1600×1200 pixels) at an aperture of f26 and shutter speed of 1/650 seconds.

Example 1

Covalent Attachment of Peptides to Gold Surfaces

This example illustrates the attachment of peptides and post-translationally modified peptides to peptide attachment surfaces.

Peptides of Structure I and post-translationally modified peptides of Structure II were synthesized. Structures I and II are shown below.

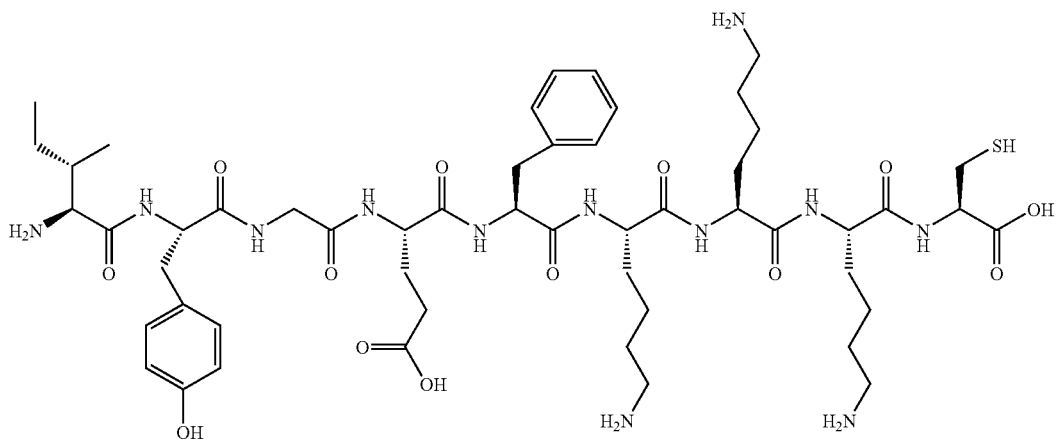

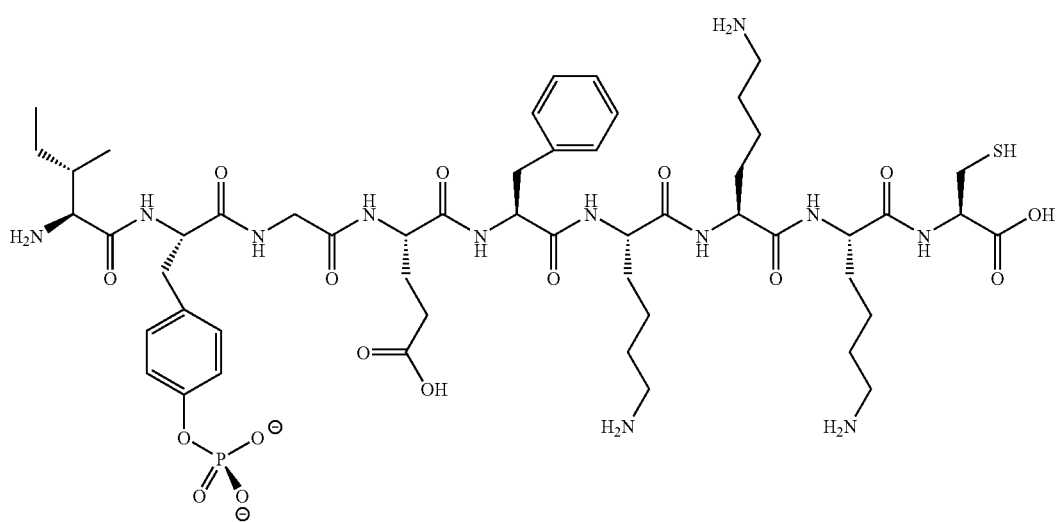

Peptide I, referred to as src-tide, comprises the amino acid sequence IYGEFKKKC (SEQ ID NO: 1) and is a known substrate for the Src protein kinase. See Houseman, B. T., et al., *Langmuir*, 19: 1522-1531 (2003). Post-translationally modified peptide II, referred to as (p) Src-tide, is a synthetic molecule (IpYGEFKKKC (SEQ ID NO: 2)) comprising a phospho-tyrosine (pY) residue that mimics Src protein kinase modification. The sequences of these molecules were confirmed using MALDI-TOF mass spectrometry. Reverse-phase C-18 HPLC analysis demonstrated that each molecule was greater than 98% pure.

The modified gold surfaces to which the peptide of Structure I or the post-translationally modified peptide of Structure II were ultimately attached after being contacted with a first thiol compound and a second thiol compound were prepared essentially as described as set forth above and described in U.S. Pat. No. 6,284,197, U.S. Pat. No. 6,692,699, and U.S. Patent Publication No. 2003/0099993 published on May 29, 2003 (all of which are herein incorporated by reference in their entireties and for all purposes as if specifically set forth herein) and illustrated in FIG. 3A. Briefly, self-assembled monolayers comprised of thiols 1 (EG3 (hydroxy tri(ethylene glycol) terminated undecylthiol) (synthesized according to the procedure set forth by Pale-Grosdemange et al. *J. Am. Chem. Soc.* 113, 12-20 (1991) which is herein incorporated by reference in its entirety and for all purposes as if fully set forth in its entirety) and 2 (EG3–N (amino tri(ethylene glycol) terminated undecylthiol; purchased from ProChimia, Gdansk, Poland) were created by immersion of gold substrates into 0.100 mM ethanolic solutions of the thiols. Each solution contained a different percentage of EG3–N to EG-3. The composition of the solutions was approximately 1%, 5%, 20%, 50% or 100% of EG3–N compared to EG3 providing peptide attachment surfaces with different molar ratios of the first thiol compound to the second thiol compound. The gold substrates were incubated in these solutions for no less than 12 hours. After incubation, the surfaces were rinsed under streams of ethanol and then were rinsed twice with water. The surface was then rinsed again with ethanol and dried under a $N_2$ stream. The angle of gold deposition was set at 45°.

Figure 3A:
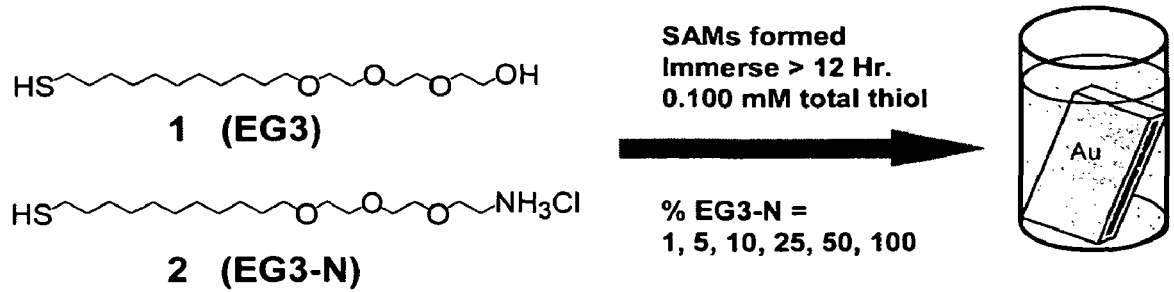
FIG. 3A is a schematic representation showing thiol compounds EG3 and EG3-N used to prepare self-assembled monolayers (SAMs) on a nano-structured gold film for use in detecting post-translationally modified peptides in an embodiment of the present invention.
Figure 3B:
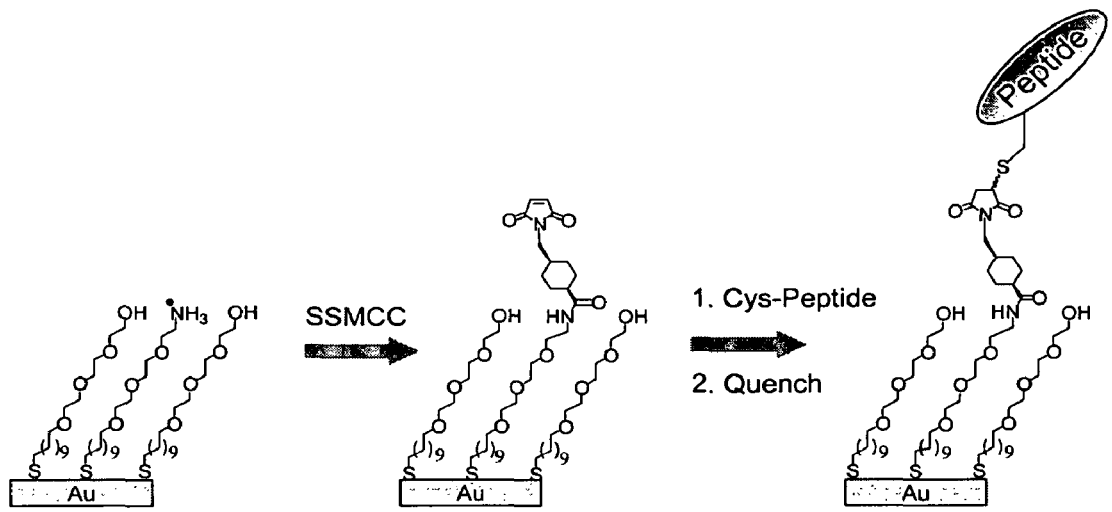
FIG. 3B is a schematic representation showing a method of attaching a peptide or post-translationally modified peptide to a self-assembled monolayer on a nano-structured gold film in an embodiment of the present invention using hetero-bifunctional linker SSMCC and cysteine-terminated peptides.

The peptide and post-translationally modified peptide were covalently attached to the surfaces using the procedure shown in FIG. 3B. In brief, the self assembled monolayers (SAMs) were chemically treated with a heterobifunctional linker, SSMCC (sulfosuccinimidyl-4-(N-maleimidomethyl) cyclohexane-1-carboxylate; catalog no. 22322, Pierce, Rockford, Ill.), to provide a peptide attachment surface. The structure of SSMCC is shown below

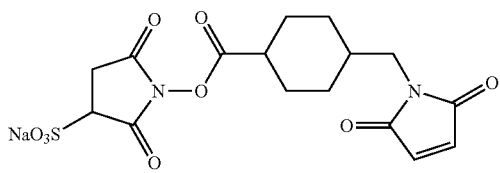

A 2 mM solution of SSMCC was prepared in 0.1M triethanolamine buffer, pH 7.0 (referred to as TEA for the purposes of this document) and applied to the self-assembled monolayer and incubated in the dark for 45 minutes, resulting in an acyl transfer reaction. The acyl transfer, in turn, leads to the formation of a peptide attachment surface with a functional thiol compound that includes a reactive maleimide functionality suitable for further modification. Peptides and post-translationally modified peptides that include cysteine residues (Cys) possess a sulfhydryl group which selectively reacts with the maleimide functionality, via a Michael addition reaction. A solution of peptide or post-translationally modified peptide (250 µM in TEA) was applied to the surface containing the maleimide group and incubated for 3 hours. Unreacted material was rinsed away using 3×1.5 mL of TEA containing 0.1% Triton-X 100. The remaining maleimide groups were quenched with 1×1.5 mL of 2 mM 2-mercaptoethanol. The samples were then rinsed under a stream of water and dried using a stream of $N_2$.

Polarization Modulation—Infrared Reflectance Absorbance Spectroscopy (PM-IRRAS)[44,47] and ellipsometry were used to 1) confirm the attachment of the maleimide group as depicted in Scheme 1B and 2) confirm control over the areal density of peptide presented on surfaces known to be largely resistant to the non-specific adsorption of proteins.

PM-IRRAS is a surface-sensitive analytical technique that can provide information about the quantity, type and orientation of organic functional groups present at an interface.[48] Shown in FIG. 3A are the PM-IRRAS spectra obtained using mixed SAMs formed from thiols EG3 and EG3–N following treatment with SSMCC. Strong absorption bands are observed for the maleimide asymmetric (1707 $cm^{-1}$) and symmetric (1745 $cm^{-1}$) stretching modes. These absorption bands were previously observed by Xiao, Textor and Spencer for peptide-modified titanium surfaces. The reaction of SSMCC with the SAM also generates one amide bond. We observe a band in the 1655 $cm^{-1}$ region, corresponding to the Amide I (C=O) stretching mode.

The magnitudes of the absorbance peaks shown in the PM-IRRAS spectra in FIG. 3A depend on the orientation and the number density of functional groups at the interface. Therefore, to make statements regarding the relative amount of SSMCC at the interface, it is necessary to determine if the orientation of the maleimide changes as a function of monolayer composition. The orientations of organic functional groups have previously been determined using infrared spectroscopy, most notably the C—H bonds present in alkanethiols chemisorbed to gold surfaces. When performing PM-IRRAS on gold films, only stretching modes parallel to the surface normal are observed. As the maleimide functional group has two stretching modes (asymmetric at 1707 $cm^{-1}$ and symmetric at 1745 $cm^{-1}$) which are geometrically orthogonal, the relative strengths of each mode indicate its molecular orientation relative to the surface. A convenient index of the orientation of maleimide groups is the ratio of peak areas (1707 $cm^{-1}$/1745 $cm^{-1}$). To calculate this index for each sample, the peak areas corresponding to each of the maleimide stretching modes were deconvoluted from baseline-corrected data by fitting to multiple Gaussian peaks. The ratio of peak areas for each sample is shown in FIG. 3B. This index was not a strong function of monolayer composition, indicating that the magnitudes of peak areas in can be used to infer the composition of the interface. Shown in FIG. 3C is a plot of the magnitude of the absorbance peaks at 1707 $cm^{-1}$ and 1745 $cm^{-1}$ as a function of monolayer composition. With increasing mole fractions of amine-terminated functionality in the SAM, we observe the areal density of immobilized maleimide group after SSMCC treatment to systematically increase.

We also used ellipsometry to characterize the maleimide-functionalized surfaces. Shown in FIG. 3D is the change in ellipsometric thickness of the SAM caused by SSMCC treatment, as a function of SAM composition. Again, a trend is observed of increasing the amount of immobilized SSMCC as a function of monolayer composition. The maximum optical thickness of 1.27±0.08 nm obtained at a 100% EG3–N monolayer is similar to the known dimensions of the SSMCC spacer of 1.16 nm, and is consistent with monolayer coverage of the maleimide. From this series of studies, we conclude that the maleimide group was incorporated into the interface. We also conclude that the orientation of the maleimide group does not change significantly as a function of areal density, and that the areal density of immobilized SSMCC is a function of changing monolayer composition. These results were supported by ellipsometry. Below, we provide evidence that these interfaces can be used to immobilize defined densities of peptides.

Figure 4:
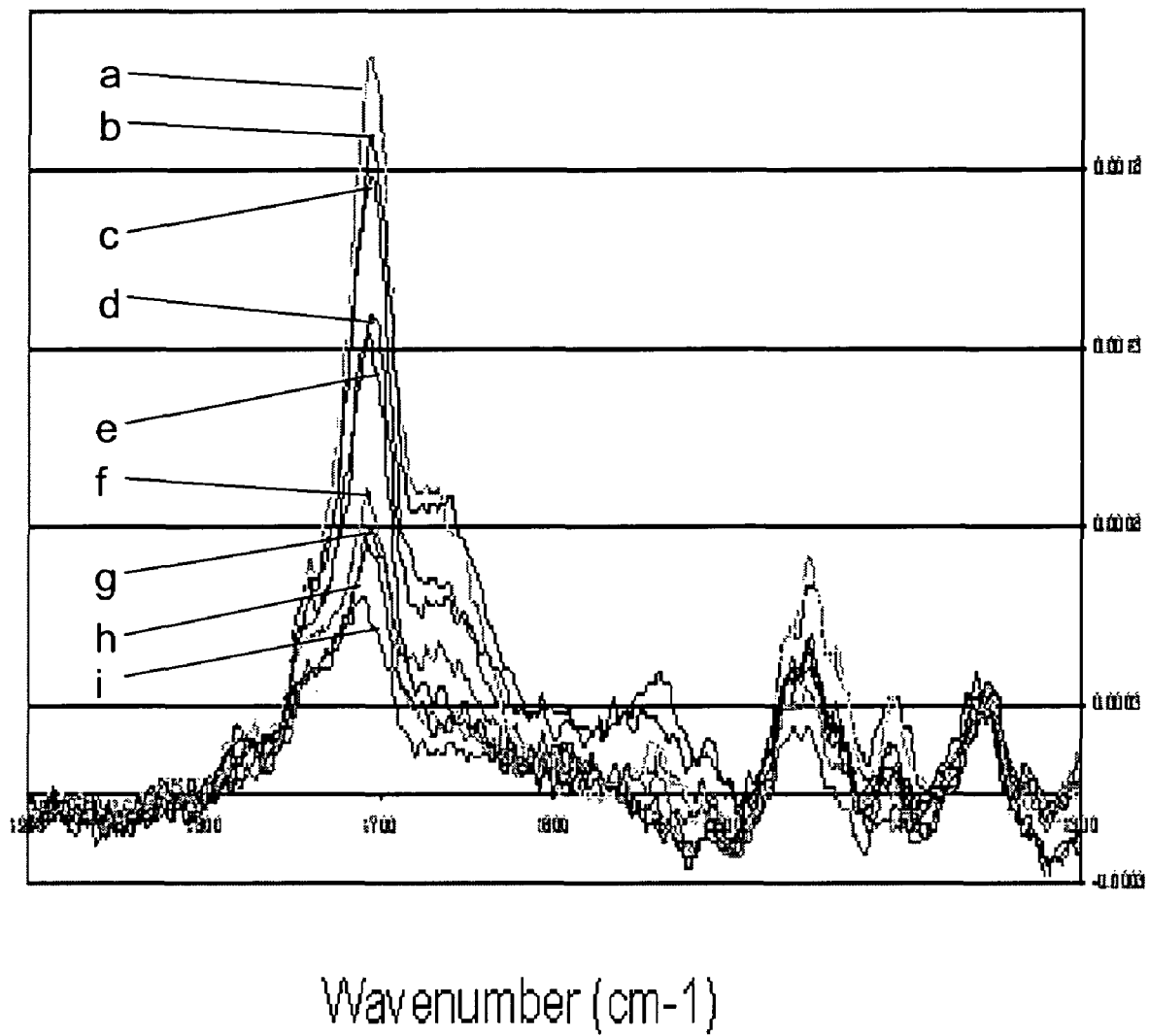
FIG. 4 is a graphical representation of the results of studies of peptides bound to SAMs of an embodiment of the present invention, showing baseline corrected PM-IRRAS spectra of preparations including a, 50% EG3–N and (p)-Src-tide; b, 20% EG3–N and (p)-Src-tide; c, 50% EG3–N and Src-tide; d, 20% EG3-N and Src-tide; e, 50% EG3-N and SSMCC; f, 20% EG3-N and SSMCC; g, 5% EG3-N and (p)-Src-tide; h, 5% EG3-N and Src-tide; and 1,5% EG3-N and SSMCC.
Figures 5A, 5B, 5C, 5D:
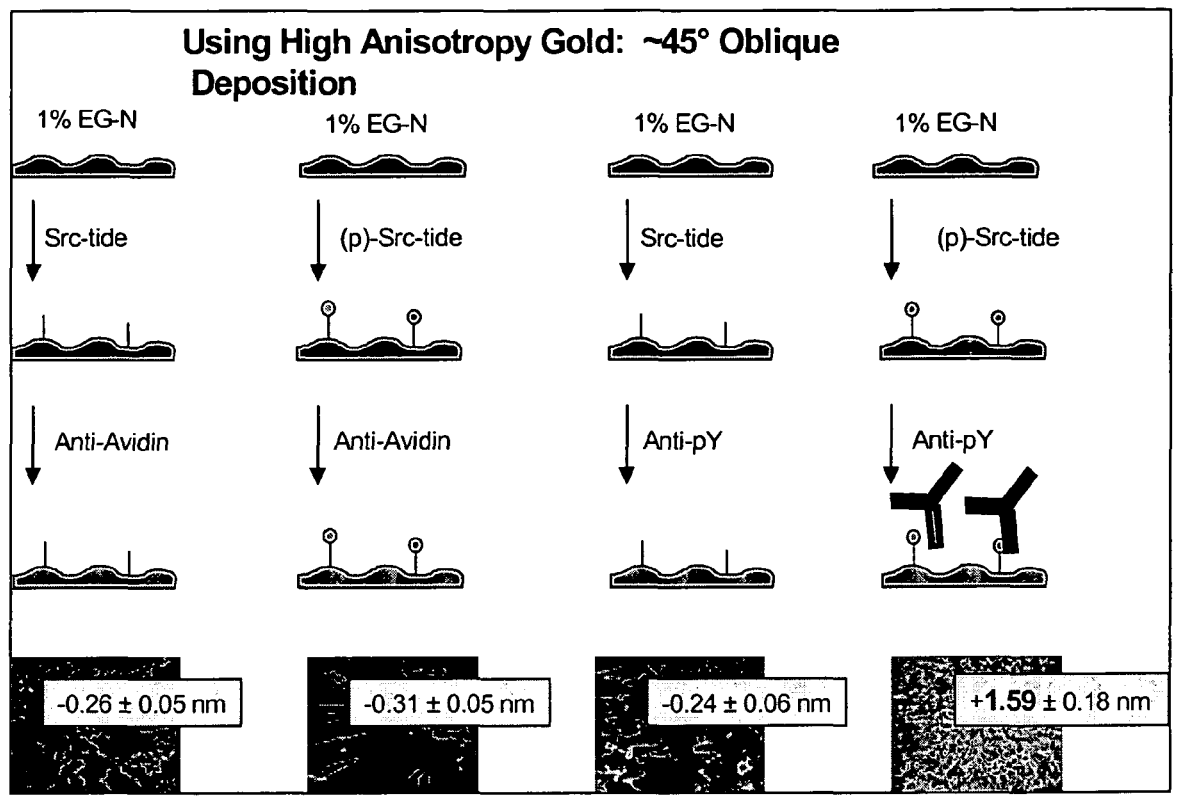
FIG. 5A-FIG. 5D are schematic representations demonstrating the detection of a post-translationally modified peptide ((p)-Src-tide) using antibodies as the recognition reagent in conjunction with the nematic liquid crystal 5CB in an embodiment of the present invention.
Figures 6A, 6B, 6C, 6D:
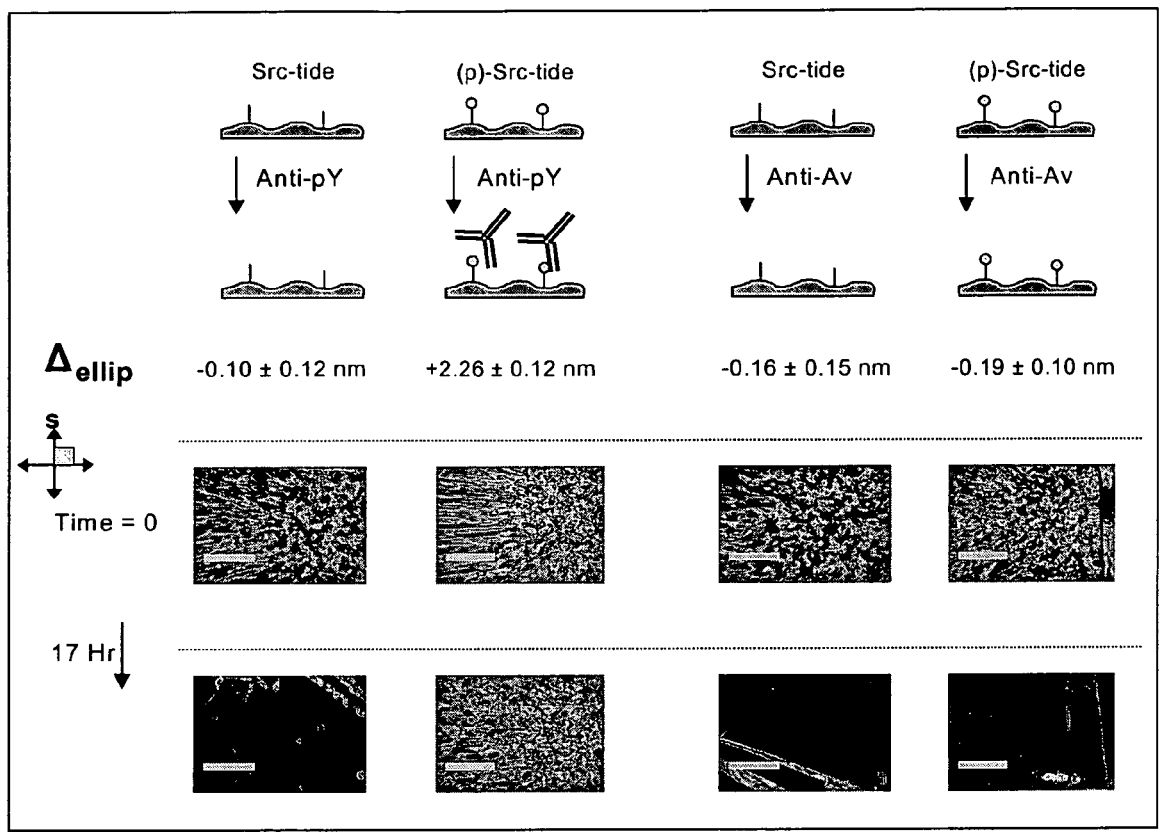
FIG. 6A-FIG. 6D are schematic representations demonstrating the detection of a post-translationally modified peptide ((p)-Src-tide) using antibodies as the recognition reagent at time 0 and 17 hours later.

The peptidized surfaces were analyzed using polarization modulation infrared reflectance absorbance spectroscopy (PMIRRAS) to confirm attachment of the peptide or post-translationally modified peptide to the surfaces. The absorbance band at 1675 $cm^{-1}$ corresponds to the amide functionality present in peptides and post-translationally modified peptides. Peptides and post-translationally modified peptides immobilized on surfaces with 1% EG3–N were of sufficiently low density that the amide absorbance was too small for good observation. However, the control samples prepared using 5%, 20% and 50% EG3–N surfaces gave rise to distinct peaks at 1675 $cm^{-1}$ confirming that the peptide and post-translationally modified peptide were attached to the surfaces (FIG. 4).

Similar manipulations were carried out to attach additional peptides and post-translationally modified peptides to peptide attachment surfaces formed from a metallized surface comprising gold. Some such peptides and post-translationally modified peptides containing serine or threonine residues subject to phosphorylation by serine and threonine protein kinases, respectively (described in Cohen, P. *Nat. Rev. Drug Discov.* 2002 April; 1(4):309-15) were used. In the case of such peptides and post-translationally modified peptides containing serine residues subject to phosphorylation, the following peptides, often referred to as Kemptide were covalently attached: CGGALRRASLG (SEQ ID NO: 3) and CGGAL-RRApSLG (SEQ ID NO: 4).

In the case of such peptides and post-translationally modified peptides containing threonine residues subject to phosphorylation, the following are exemplary peptides that may be covalently attached. In each case, the unphosphorylated and phosphorylated mimic molecules are attached as described above: KRTIRR (SEQ ID NO: 5) and KRTpIRR (SEQ ID NO:6), described in Mahoney, C. W. et al., *Analytical Biochemistry* 268: 371-376 (1999) which is hereby incorporated by reference in its entirety and for all purposes as if fully set forth herein. Because this motif lacks a cysteine residue, such a residue may be added during synthesis at either terminus such that the peptide would react when contacted with the SSMCC or other heterobifunctional linker, as described in Houseman et al., supra).

In some cases, peptides and post-translationally modified peptides may be attached to the peptide attachment surface at different densities such as, but not limited to, in a density gradient. Previous work has used diffusion to control the gradient (Liedberg, B., et al., *Langmuir,* 13: 5329-5334 (1997)), microfluidic devices to present solutions/surfaces having gradients (Jeon, N. L., et al., *Langmuir,* 16: 8311-8316 (2000)), and an approach using current passing through a thin gold film (Terrill, R. H., et al., *J. Am. Chem. Soc.* 122: 988-989 (2000)). The last approach noted above has been used to fabricate gradients of the peptide RGD on surfaces (Wang, Q. et al., *Anal. Chem.* 76: 1-8 (2004)). Additionally, the molar ratio of the first thiol compound to the second thiol compound may be varied across a peptide attachment surface to control how much peptide or post-translationally modified peptide is attached to the peptide attachment surface when contacted with these. Each of the articles cited above are herein incorporated by reference in their entireties and for all purposes as if fully set forth herein.

Example 2

Detection of Phosphorylated Proteins

This example illustrates the suitability of liquid crystals for distinguishing between phosphorylated and unphosphorylated peptides and peptide fragments.

In some embodiments, antibodies specific for phosphotyrosine residues were used to aid in discrimination of phosphorylated vs. unphosphorylated protein fragments. In other embodiments, an intermediary molecule is used to augment the distinction between phosphorylated vs. unphosphorylated protein fragments. In yet other embodiments, direct detection of phosphorylated residues are used.

A. Antibody-Mediated Recognition of Phosphorylated Tyrosine

Both unphosphorylated (src-tide) and phosphorylated ((p) src-tide) peptide fragments were covalently bound to modified gold surfaces as described in Example 1. These surfaces were then exposed to solutions of phosphate buffered saline (PBS), pH 7.0+1% Triton-X containing either 10 μg/ml of antibody to avidin (control) (Sigma Aldrich, St. Louis, Mo., Cat. No. F 1269) or 10 μg/ml antibody specific for phosphotyrosine (Sigma Aldrich, Cat. No. F 1345). The surfaces were incubated with the antibody solution for 1.5 hours at room temperature and then were quickly washed (15 seconds in PBS+0.05% Triton-X), rinsed with water, and then dried under a stream of $N_2$. Finally, the peptides and post-translationally modified peptides (phosphorylated peptides) on these surfaces were imaged using the nematic liquid crystal 5CB. So-called sandwich cells were prepared by placing two identically functionalized incubated surfaces face-to-face. These two surfaces were separated using 12 μm plastic spacers, and this cell was filled with 5CB warmed to its isotropic phase. The cells were cooled slowly to room temperature and visualized under a polarizing microscope set to cross polarizers. The images obtained in this manner are shown in FIG. 5A-FIG. 5D. The anti-phosphotyrosine (anti-pY) has a strong affinity only for the phosphorylated (p)-Src-tide. This protein binding event was monitored using ellipsometry (grey insert boxes) as well as by signal transduction to the liquid crystal (compare the number of defects in the minus and plus antibody images) due to the loss of surface anchoring from the obliquely deposited gold substrate. FIG. 6A-FIG. 6D show the results of similar experiments in which peptides and phosphorylated peptides were bound at a density of greater than 1%. In this case, a highly reproducible transition in the liquid crystal was observed over the course of 17 hours.

Figures 7A, 7B, 7C:
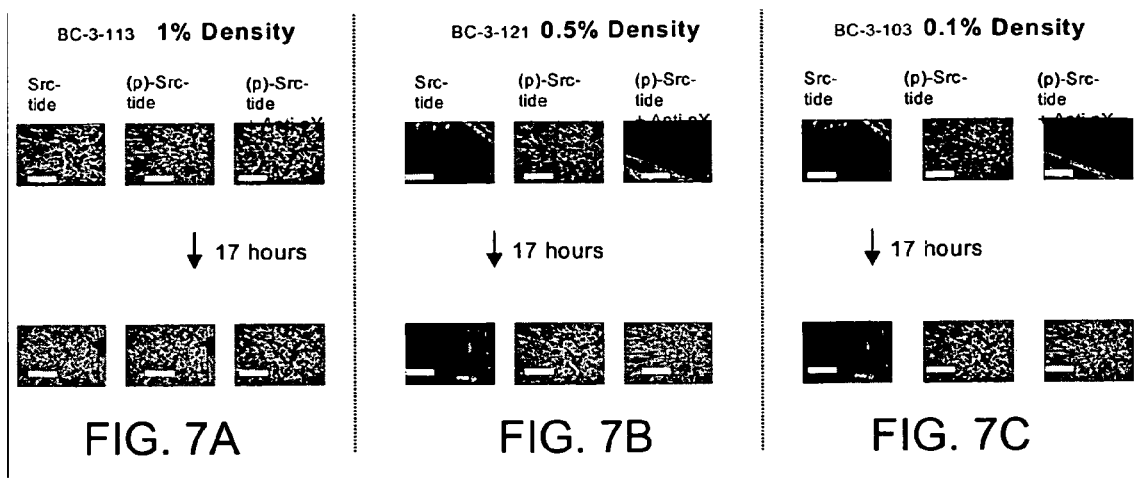
FIG. 7A-FIG. 7C are graphical representations of the results of studies showing detection of a phosphorylated peptide at peptide areal densities of 1% (FIG. 7A), 0.5% (FIG. 7B) and 0.1% (FIG. 7C) using nematic liquid crystal 5CB and an anti-phosphotyrosine antibody as recognition reagent.
Figures 8A, 8B, 8C, 8D:
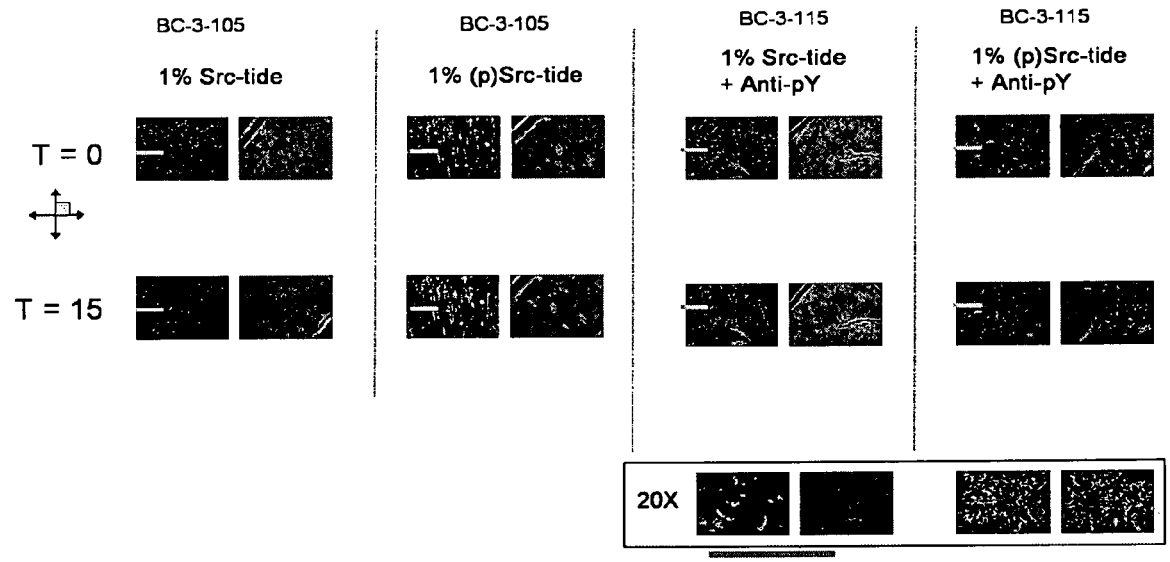

FIG. 7A-FIG. 7C show the results of experiments in which the density of protein binding was varied from 1% to 0.5% to 0.1%. Samples were prepared as described above, except that serial dilutions of EG3-N were made to accurately control the composition of the monolayer. At the lowest threshold limit tested (righthand panel), the density of the peptide or post-translationally modified peptide was too low to elicit a liquid crystal response.

FIG. 8A-FIG. 8D show the results of using an alternative nematic liquid crystal, MBBA (N-(4-methoxybenzylidene)-4-butylaniline) (available from Aldrich, Product No. 158224), to detect binding of anti-pY to immobilized peptides or post-translationally modified peptides. The structure of MBBA is shown below.

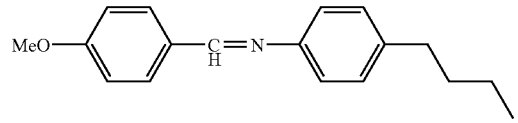

MBBA exhibits negative dielectric anisotropy, as opposed to 5CB, used in experiments presented in FIG. 5A-FIG. 5D and FIG. 6A-FIG. 6D, which exhibits positive dielectric anisotropy. In these experiments, samples were prepared using 1% areal density of protein binding to EG3-N. All samples were prepared as described for the experiment in FIG. 5A-FIG. 5D and FIG. 6A-FIG. 6D prior to the addition of the liquid crystal. Examination of the images in FIG. 7A-FIG. 7C indicates that differences in light scattering were apparent immediately upon addition of the liquid crystal to the samples containing phosphorylated protein bound to anti-phosphotyrosine (anti-pY).

B. Intermediary Reagent Other than Antibody

The phosphate group on a phosphorylated amino acid such as tyrosine, caries a net negative charge. Thus, cationic reagents that both recognize the phosphate moiety and perturb the orientations of the mesogens at the interface of the optical cell may serve as an alternative to antibodies in facilitating the detection of phosphorylated peptides by liquid crystals. In particular, iron-based cationic reagents capable of selective binding to phosphate groups, such as IQ™ (Pierce, Rockford, Ill., Cat. No. 62120) or the fluorescent Pro-Q Diamond phosphosensor dye (Molecular Probes, Eugene, Oreg., described in Martin, K. et al., *Proteomics,* 3: 1244-1255 (2003)) may be suitable intermediate compounds for use in differentiating between phosphorylated peptides and peptides. In other cases, cationic surfactants such as CTAB (cetyltrimethylammonium bromide), and polyelectrolytes, such as polylysine or polyethylimine (PEI) may also be used.

Peptide attachment surfaces are prepared and peptides, post-translationally modified peptides, or mixtures thereof are attached to the surfaces as described in Example 1. Both the peptide of Structure I and the phosphorylated peptide of Structure II are covalently bound to the peptide attachment surface as described in Example I to provide peptidized surfaces. The intermediary reagent recognition reagent is applied as described for antibody incubation above. Titrations are carried out on both positive and negative control peptide and post-translationally modified peptides attached to the peptidized surfaces at a range of concentrations to determine the optimal amount of reagent to add, the number and types of washes to carry out, etc. as for antibody-mediated recognition. Solutions and conditions for blocking and for washing surfaces are well known to those skilled in the art. Exemplary blocking and washing reagents and solutions are described, for example, in Sambrook, J., Fritsch, E. F., and Maniatis, T. (1989) in: MOLECULAR CLONING: A LABORATORY MANUAL, COLD SPRINGS HARBOR LABORATORY. The peptides and post-translationally modified peptides on the surfaces are then imaged as described above in Example 2A and visualized under a polarizing microscope set to cross polarizers. Differences are observed between the incubated surfaces that include the peptide and those that include the phosphorylated peptide.

C. Direct Detection of Phosphorylated Peptides

In some cases, phosphorylated peptides may be differentiated from peptides without the need for additional molecules to facilitate the generation of an optical signal in the presence of liquid crystals. In this example, both peptides and phosphorylated peptides were bound to peptide attachment surfaces comprising a metallized gold coated surfaces prepared as described in Example 1. The peptide had the sequence CGGALRRASLG (SEQ ID NO: 3) and the phosphorylated peptide had the sequence CGGALRRApSLG (SEQ ID NO: 4), respectively. Sandwich cells were prepared as described in Example 2A, and the cells were filled with 5CB liquid crystal solution warmed to its isotropic phase. The areal density of EG3–N was 5%, and the angle of oblique gold deposition was 40°. The cells were cooled slowly to room temperature and visualized under a polarizing microscope set to crossed polarizers. The results are presented in FIG. 9A-FIG. 9C. Comparison of the images in the SSMCC only column and the SSMCC and peptide to those of the SSMCC and phosphorylated peptide indicate that in 2 of the 3 replicates, the 5CB detection of the phosphorylated peptide yielded color changes indicative of protein binding, suggesting that in some cases, liquid crystals may be used to directly differentiate between peptides and post-translationally modified peptides without the use of an antibody or other detection compound. In some embodiments, it may be desirable to monitor the time dependence of the loss of surface anchoring such that phosphorylated peptides cause accelerated loss of surface anchoring relative to peptides.

Example 3

Quantification of the Ratio of Phosphorylated to Unphosphorylated Peptide

This example illustrates the suitability of liquid crystal devices for quantifying the ratio of phosphorylated to unphosphorylated peptide.

Peptide attachment surfaces with gold metallized surfaces were prepared as described in Example 1. Both src-tide and (p) src-tide were covalently bound to the surfaces as described in Example 1 to provide peptidized surfaces except that the peptides and phosphorylated peptides were immobilized in spots at relatively low density, i.e. 0.5% EG3–N. Mixtures comprising the peptide and phosphorylated peptide were prepared as shown in the following Table 2.

TABLE 2

| Mixtures Comprising The Peptide And Phosphorylated Peptide | |
|---|---|
| % Src-tide | % (p)src-tide |
| 0 | 100 |
| 5 | 95 |
| 25 | 75 |
| 50 | 50 |
| 100 | 0 |

Figure 10:
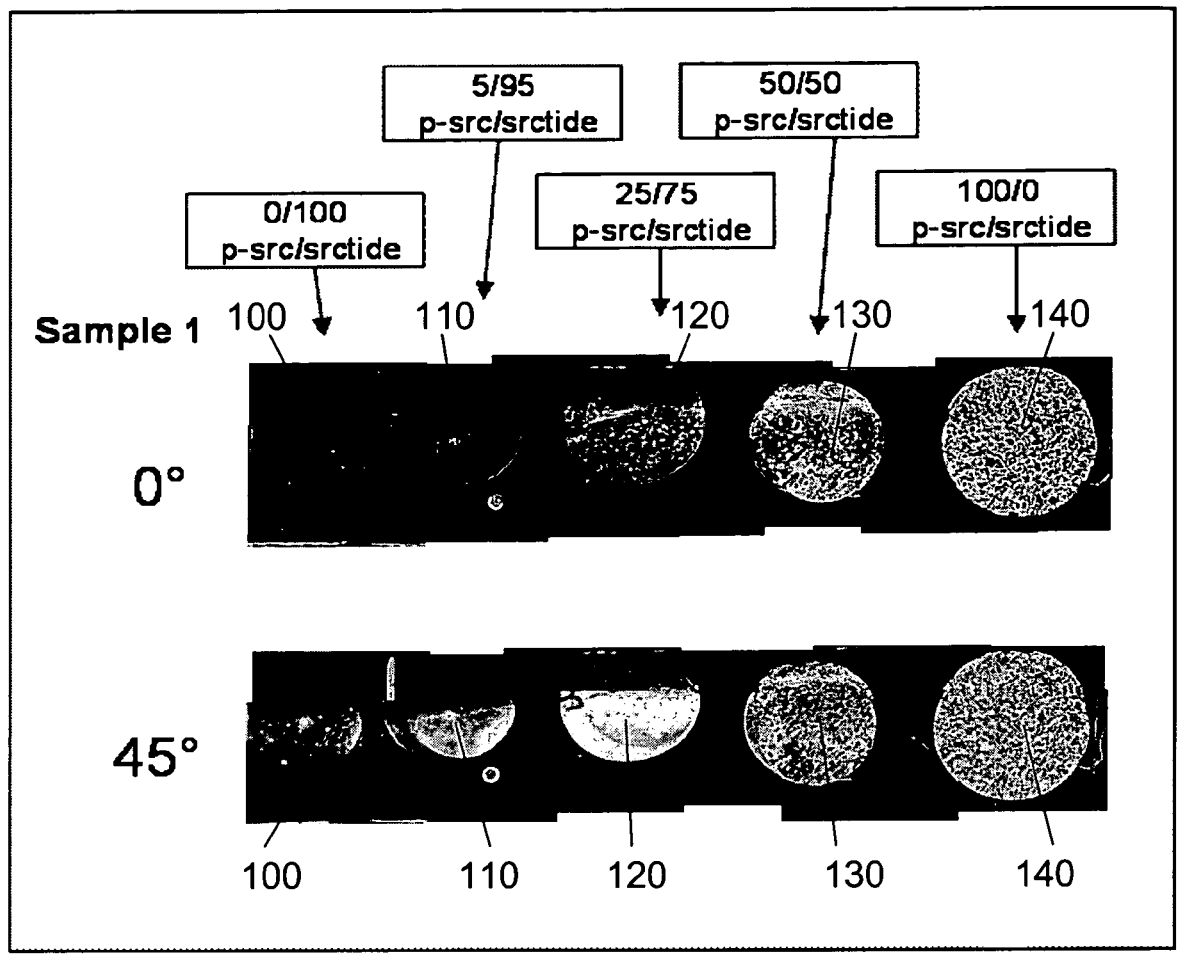
FIG. 10 is a scanned image showing the detection phosphorylated peptide at different ratios phosphorylated peptide to non-phosphorylated peptide on an array with spots of src-tide alone (SEQ ID NO: 1) 100, p-src-tide alone (SEQ ID NO: 2) 140, and spots (110, 120, 130) in which p-src-tide is 5%, 25% or 50% of the peptide mixture, respectively. The density of attachment is 0.5% for all spots. The arrayed spots containing higher levels of p-src-tide produce stronger optical signals from the liquid crystal than those with lower levels. The interference colors and number of disclination lines for each spot can be used as indices for quantification. Note that the number of defect lines is maximal at the pure p-src-tide spot 140.

Sandwich cells were prepared as described in Example 2A, and cells were filled with 5CB solution warmed to its isotropic phase. The cells were cooled slowly to room temperature and visualized under a polarizing microscope set to crossed polarizers. The results are presented in FIG. 10 and demonstrate that the increasing ratio of (p) src-tide to src-tide are clearly distinguishable, with as little as 5% being detectable.

Example 4

Liquid Crystal Imaging of Phosphorylation on a 2-Dimensional Peptide Array

Arrays comprising peptides and post-translationally modified peptides were constructed in a manner similar to that described in Example 1. However, regions of peptide and post-translationally modified peptides were defined by spotting. The entire surface was treated with a 2 mM solution of SSMCC in TEA. Next, ~2.5 µL of a 250 µM solution of peptide in TEA were applied to this surface as spots (having lateral dimensions of ~1 mm). After 3 hr, the entire surface was rinsed 2×1.5 mL×5 min TEA+0.1% TX. The remaining maleimide groups were quenched by treatment of the entire surface with a 2 mM solution of 2-mercaptoethanol in PBS for 10 min. Finally these samples were rinsed and dried.

Figures 11A, 11B:
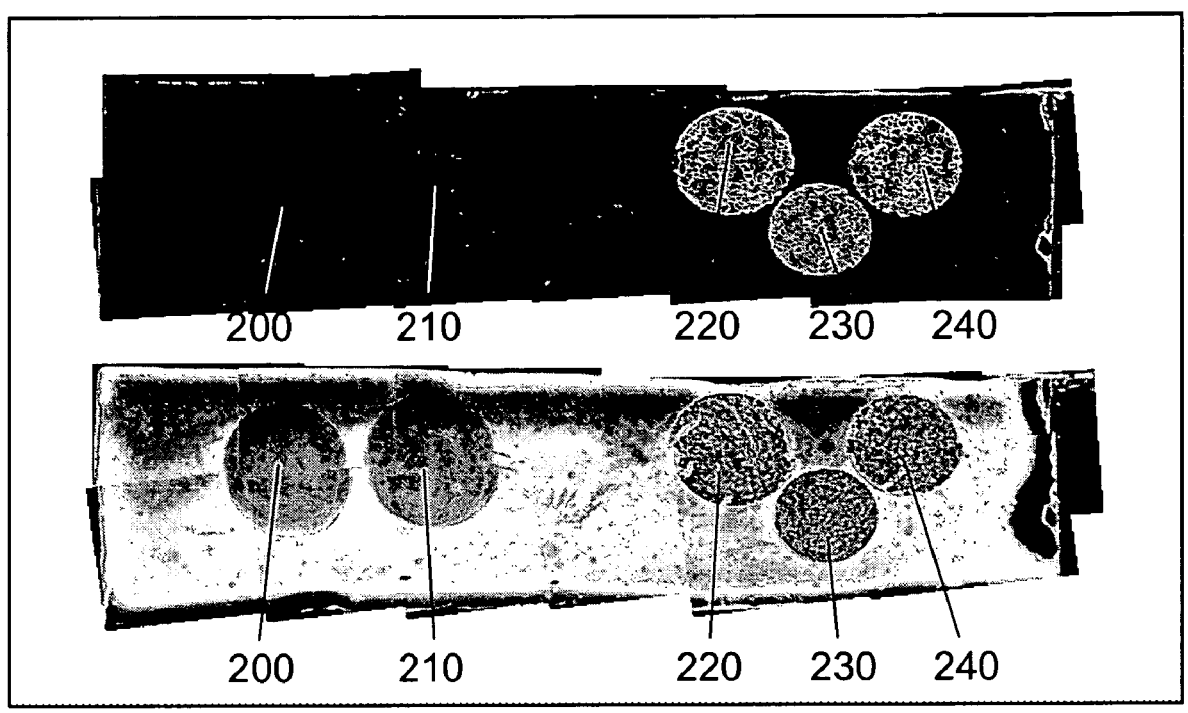
FIG. 11A and FIG. 11B are scanned images showing a liquid crystal imaging of a two-dimensional peptide array showing spots 200, 210 of a peptide and spots 220, 230, 240 of a post-translationally modified peptide.

In this example, the percentage of EG-3N (in a background of EG-3) was 0.5%, such that there were defined regions of peptide (100%) and phosphorylated peptide (100%). The peptide and post-translationally modified peptide used were the same as those in Example 2A, as were the conditions and anti-pY solutions and reagents used, including nematic liquid crystal 5CB. The results are presented in FIG. 11A and FIG. 11B and indicate that phosphorylation state can be detected by liquid crystals on 2-dimensional arrays.

Example 5

Attachment of Peptides to Surfaces Other than Gold

In some cases, it may be desirable to employ surfaces other than gold coated slides for attachment of peptides and analysis using liquid crystals. Surfaces including, but not limited to, glass, silica or silicon, titania or titanium, and alumina or aluminum are all amenable to modification to introduce functional groups such as amines and thiols. In particular, Charles et al. describe attachment of oligonucleotides to glass surfaces and silicon wafers modified with common aminosilanes, 3-aminopropyltriethoxysilane (APES), N-(2-aminoethyl)-3-aminopropyltrimethoxysilane, or m,p-(aminoethylaminomethyl) phenethyltrimethoxysilane (*Langmuir* 19: 1586-1591 (2003)), herein incorporated by reference in its entirety. These surface modifying agents serve to introduce terminal amines to the surface, thereby providing a functionalized surface to allow subsequent attachment of various molecules. These terminal amines are in turn reacted with an appropriate heterobifunctional linker such as SSMCC as described in example 1. Lastly, a mixture of peptide and compound such as a second thiol of the invention, for example, EG-3, is injected to permit peptide attachment at the desired molar ratio. For example, for a 1% peptide binding density, a solution of 1% peptide to 99% EG-3 (or other inert thiol) is injected. Similarly, various alternative methods are described for attachment of peptides to modified titanium surfaces (Xiao, S-J. et al., supra).

Example 6

Preparation and Characterization of Maleimide-Modified Surfaces

A series of two-component SAMs on gold were prepared using thiols EG3 and EG3–N The solution compositions of thiol EG3–N used in these studies were 1, 5, 10, 25, 50 and 100 mol %. The SAM surfaces are conveniently designated by the composition of the ethanolic solutions used to form each SAM, i.e. a 5% EG3–N SAM was formed from an ethanolic solution comprised of 5 mol % EG3–N and 95 mol % EG3 thiols. Coadsorption of thiols having similar structure and length is unlikely to lead to segregation of species within the mixed SAM. These surfaces were then treated with the hetero-bifunctional linker SSMCC (see Methods). Polarization Modulation—Infrared Reflectance Absorbance Spectroscopy (PM-IRRAS) and ellipsometry were used to 1) confirm the attachment of the maleimide group and 2) confirm control over the areal density of peptide presented on surfaces known to be largely resistant to the non-specific adsorption of proteins.

PM-IRRAS is a surface-sensitive analytical technique that can provide information about the quantity, type and orientation of organic functional groups present at an interface.48 PM-IRRAS. IR spectra of SAMs supported on gold films (thickness of 2000 Å) were obtained using a Nicolet Magna-IR 860 FT-IR spectrometer with photoelastic modulator (PEM-90, Hinds Instruments, Hillsboro, Oreg.), synchronous sampling demodulator (SSD-100, GWC Technologies, Madison, Wis.) and a liquid $N_2$-cooled mercury cadmium telluride (MCT) detector. All spectra were taken at an incident angle of 83° with the modulation centered at 1800 $cm^{-1}$. For each sample, 500 scans were taken at a resolution of 4 $cm^{-1}$. Data was collected as differential reflectance vs. wavenumber and spectra were normalized and converted to absorbance units via the method outlined in Frey, B. L.; Robert, M. C.; Weibel, S. C. Polarization-Modulation Approaches to Reflection-Absorption Spectroscopy. In *Handbook of Vibrational Spectroscopy*; Griffiths, P. R., Ed.; John Wiley & Sons: New York, 2002; Vol. 2; pp 1042. For quantitative analysis, spectra were fit to multiple Gaussian peaks using Igor Pro 4. Residuals were minimized, and the areas of each peak were determined.

Figure 12A:
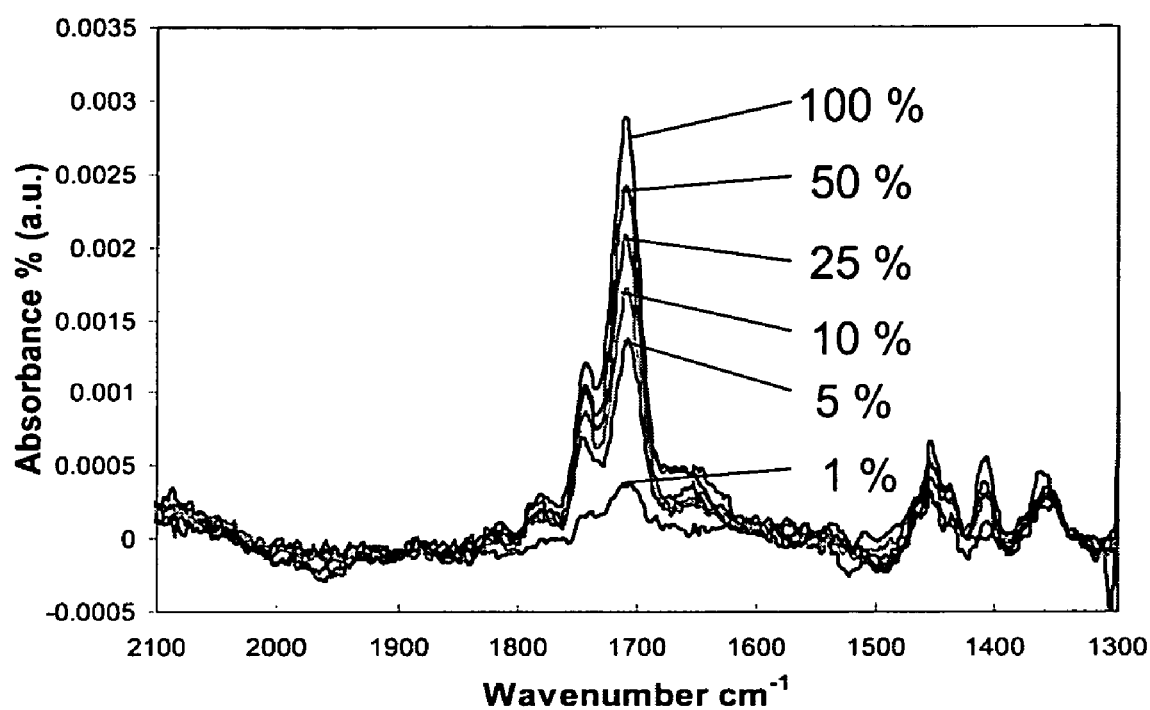
FIG. 12A is a graphical representation of the results of studies characterizing SAMs of an embodiment of the present invention, showing baseline corrected PM-IRRAS spectra of SAMs formed from ethanolic solutions of a mixture of EG3-N and EG3 thiols, labeled by the percent of EG3-N in the thiol mixture.

Shown in FIG. 12A are the PM-RRAS spectra obtained using mixed SAMs formed from thiols EG3 and EG3–N following treatment with SSMCC. Strong absorption bands are observed for the maleimide asymmetric (1707 $cm^{-1}$) and symmetric (1745 $cm^{-1}$) stretching modes. These absorption bands were previously observed by Xiao, S.-J.; Textor, M.; Spencer, N. D. *Langmuir* 1998, 14, 5507 for peptide-modified titanium surfaces. The reaction of SSMCC with the SAM also generates one amide bond. A band in the 1655 $cm^{-1}$ region is observed, corresponding to the Amide I (C=O) stretching mode.

Figure 12B:
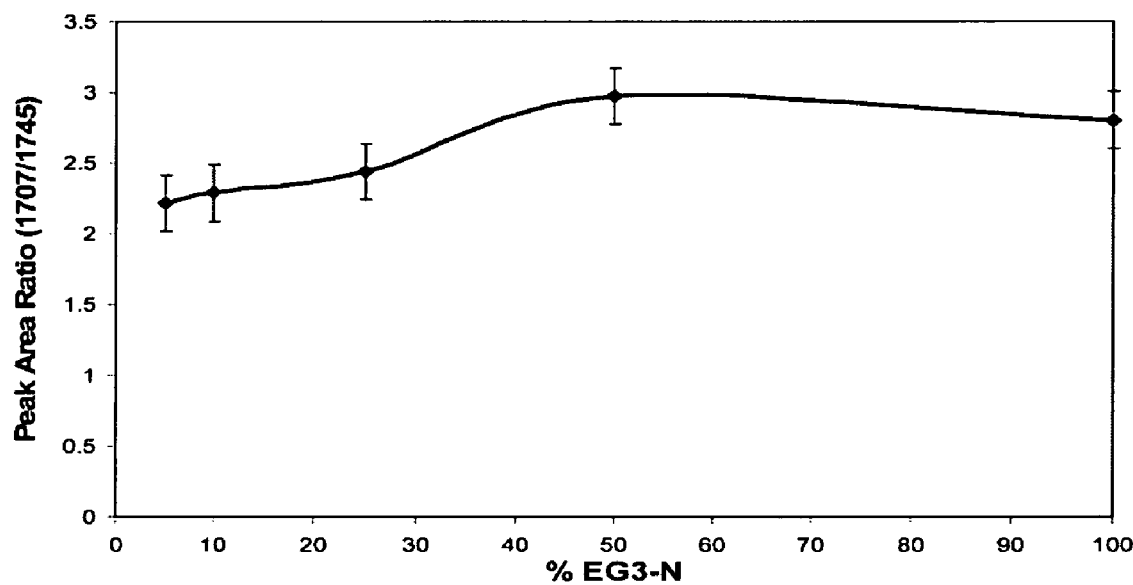
FIG. 12B is a graphical representation of the calculated ratio of the peak areas at 1707 cm-1 and 1745 cm-1 of the spectra of FIG. 4A as a function of the percent of EG3-N in the thiol mixture.
Figure 12C:
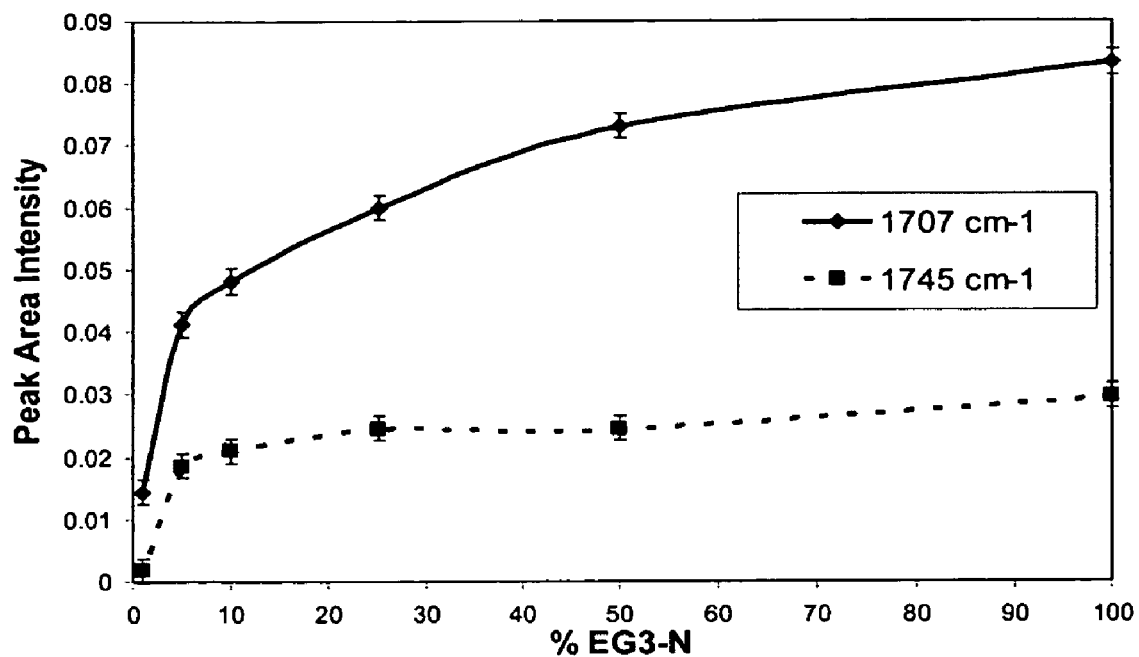
FIG. 12C is a graphical representation of the peak area intensities for the maleimide symmetric and asymmetric stretching modes as a function of the percent of EG3-N in the thiol mixture.

The magnitudes of the absorbance peaks shown in the PM-IRRAS spectra in FIG. 12A depend on the orientation and the number density of functional groups at the interface. Therefore, to make statements regarding the relative amount of SSMCC at the interface, it is necessary to determine if the orientation of the maleimide changes as a function of monolayer composition. The orientations of organic functional groups have previously been determined using infrared spectroscopy, most notably the C—H bonds present in alkanethiols chemisorbed to gold surfaces. Nuzzo, R. G.; Dubois, L. H.; Allara, D. L. *J. Am. Chem. Soc.* 1990, 112, 558. When performing PM-IRRAS on gold films, only stretching modes parallel to the surface normal are observed.47 As the maleimide functional group has two stretching modes (asymmetric at 1707 $cm^{-1}$ and symmetric at 1745 $cm^{-1}$) which are geometrically orthogonal, the relative strengths of each mode indicate its molecular orientation relative to the surface. A convenient index of the orientation of maleimide groups is the ratio of peak areas (1707 $cm^{-1}$/1745 $cm^{-1}$). To calculate this index for each sample, the peak areas corresponding to each of the maleimide stretching modes were deconvoluted from baseline-corrected data by fitting to multiple Gaussian peaks. The ratio of peak areas for each sample is shown in FIG. 12B. As this index was not a strong function of monolayer composition, we conclude that magnitudes of peak areas in FIG. 12A can be used to infer the composition of the interface. Shown in FIG. 12C is a plot of the magnitude of the absorbance peaks at 1707 $cm^{-1}$ and 1745 $cm^{-1}$ as a function of monolayer composition. With increasing mole fractions of amine-terminated functionality in the SAM, we observe the areal density of immobilized maleimide group after SSMCC treatment to systematically increase.

Figure 12D:
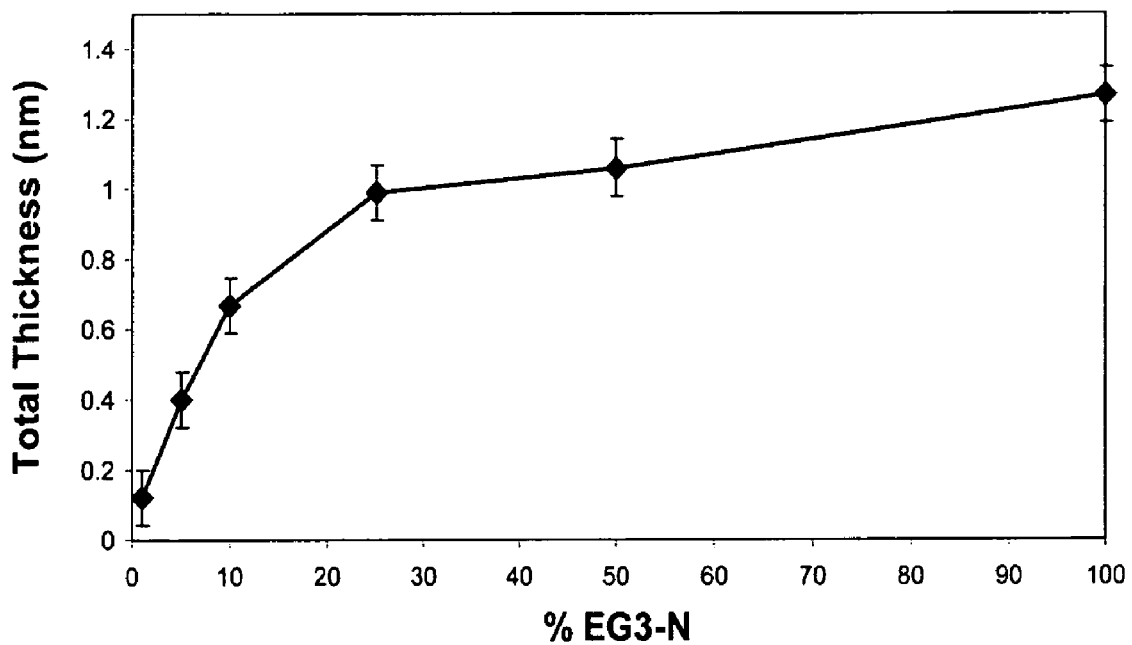
FIG. 12D is a graphical representation of the optical thickness of the maleimide-modified SAMs as a function of the percent of EG3-N in the thiol mixture.

Ellipsometry was used to characterize the maleimide-functionalized surfaces. Shown in FIG. 12D is the change in ellipsometric thickness of the SAM caused by SSMCC treatment, as a function of SAM composition. Again, a trend is observed of increasing the amount of immobilized SSMCC as a function of monolayer composition. The maximum optical thickness of 1.27±0.08 nm obtained at a 100% EG3–N monolayer is similar to the known dimensions of the SSMCC spacer of 1.16 nm, and is consistent with monolayer coverage of the maleimide.

This series of studies indicates that the maleimide group was incorporated into the interface. Further, the orientation of the maleimide group does not change significantly as a function of areal density, and that the areal density of immobilized SSMCC is a function of changing monolayer composition. These results were supported by ellipsometry.

Example 7

Preparation and Characterization of Peptide-Modified Interfaces

An identical series of maleimide-modified surfaces, as characterized above, were prepared for subsequent reaction with the cysteine-containing peptides. Two parallel sets of experiments were performed, again using the 1, 5, 10, 25, 50, and 100 mol % EG3–N SAMs. One set was treated with a 250 µM solution of Src-tide, and the other was treated with a 250 µM solution of the phosphorylated peptide, or p-Src-tide (chemical structures I and II, SEQ ID NO:1 and SEQ ID NO:2). A three hour reaction time was chosen based on previously published results. Xiao, S.-J.; Textor, M.; Spencer, N. D. *Langmuir* 1998, 14, 5507. Cysteine-terminated peptides were used to react site-specifically with surface-immobilized maleimide groups. Unreacted maleimide groups on the surface were quenched with 2-mercaptoethanol. The surfaces were characterized by PM-IRRAS and ellipsometry.

Shown in FIG. 13A and FIG. 13B are the baseline corrected PM-IRRAS spectra of Src-tide and p-Src-tide surfaces, respectively. The incorporation of peptide functionality at these interfaces is apparent, as both Amide 1 (1655 cm$^{-1}$) and Amide II (1539 cm$^{-1}$) bands are present in each series. To extract the contribution of each peptide from the measured absorbance spectra, the corresponding maleimide absorbance spectra were subtracted from each peptide (baseline-corrected) data set (FIG. 13C and FIG. 13D). The difference spectra so-obtained highlights not only the increased magnitude of the Amide I and Amide II absorbance peaks as a function of monolayer composition, but also clearly shows a loss of intensity at 1745 cm$^{-1}$ (maleimide symmetric stretching mode) after peptide immobilization. Tis loss in intensity of the symmetric stretching mode may be due to a breaking of molecular symmetry upon formation of the covalent adduct.

Figure 14A:
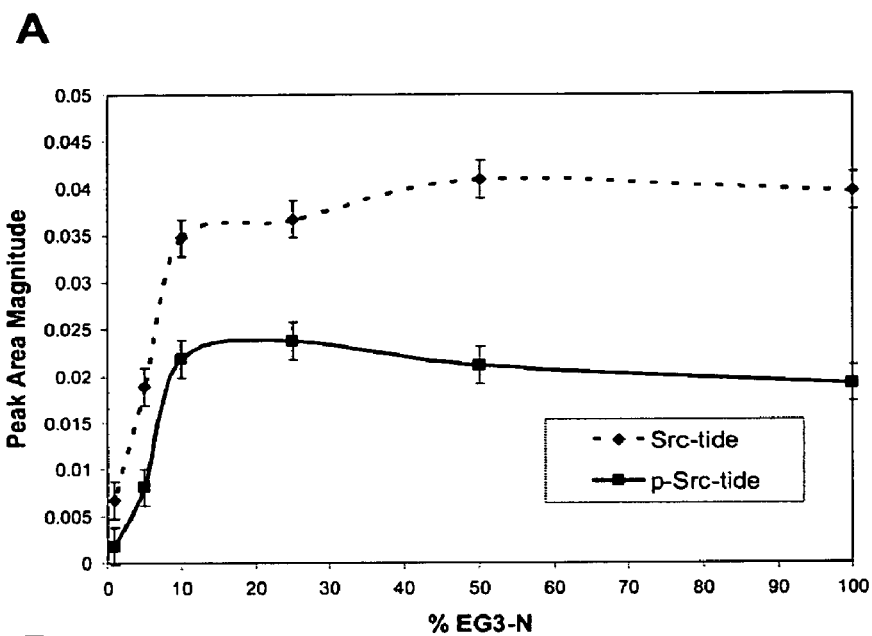
FIG. 14A is a graphical representation of the results of studies characterizing peptide-modified SAMs of an embodiment of the present invention, showing plots of Amide I peak areas for Src-tide and (p)-Src-tide immobilized peptides as a function of the percent of EG3-N in the thiol mixture.

As overlapping peaks in the baseline-corrected spectra (FIG. 13A and FIG. 13B) prevented the direct analysis of peak areas, each data set was fit to multiple Gaussian peaks. The Amide I peak areas were corrected by subtracting from this the initial Amide I intensity obtained from the maleimide-modified surfaces and plotted as a function of monolayer composition (FIG. 14A). This correction assumes that the orientation of the amide bond formed after reaction with SSMCC does not change after peptide immobilization. It appears that full surface coverage of each peptide is achieved at a SAM composition near 10% EG3–N. A 9-residue peptide is larger than the SSMCC linker, and it is likely that fewer peptide molecules per unit area correspond to full surface coverage. Furthermore, the magnitude of the Src-tide Amide I absorption is greater than the corresponding p-Src-tide series and that this difference in magnitude is greatest when using SAMs rich in EG3–N (10-100%).

Figure 14B:
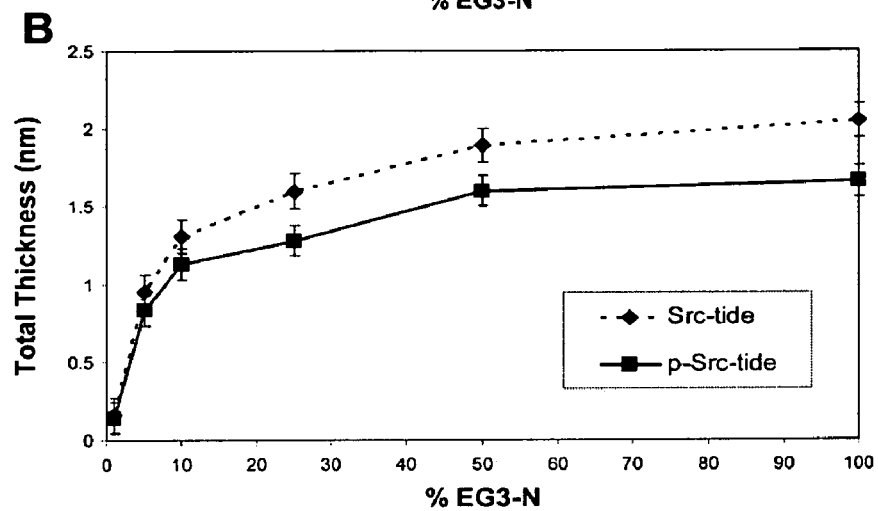
FIG. 14B is a graphical representation of the ellipsometric thicknesses of the peptide-modified SAMs samples of FIG. 14A as a function of the percent of EG3-N in the thiol mixture.

Ellipsometric measurements of the peptide-modified surfaces showed changes in optical thicknesses of the SAMs after both SSMCC treatment and peptide immobilization as shown in FIG. 14B. A Rudolph AutoEL ellipsometer (wavelength of 632 mm, 70° angle of incidence) was used to determine the optical thickness of the SAMs, peptides and proteins on the surfaces of 2000 Å thick gold films. Ellipsometric constants were determined at five locations on each sample. A simple slab model was then used to interpret these constants. The slab (SAM, peptide and protein) was assumed to have an index of refraction of 1.46.

Again, the amount of immobilized peptide is observed to be a function of monolayer composition, and there exists a difference in the total amounts of Src-tide and p-Src-tide present at the interface. The maximum contribution of each peptide to the total optical thickness was calculated to be 0.78 nm (Src-tide) and 0.39 nm (p-Src-tide). Although these increments are smaller than what was observed for the addition of the SSMCC linker (1.27 nm), it is not an unphysical optical thickness for a 9-residue peptide. Others have reported the optical thickness of a larger, 17-residue peptide chemisorbed directly onto a gold surface to range from 1.10 nm to 2.82 nm (Petoral, R. M.; Herland, A.; Broo, K.; Uvdal, K. *Langmuir* 2003, 19, 10304).

Figure 14C:
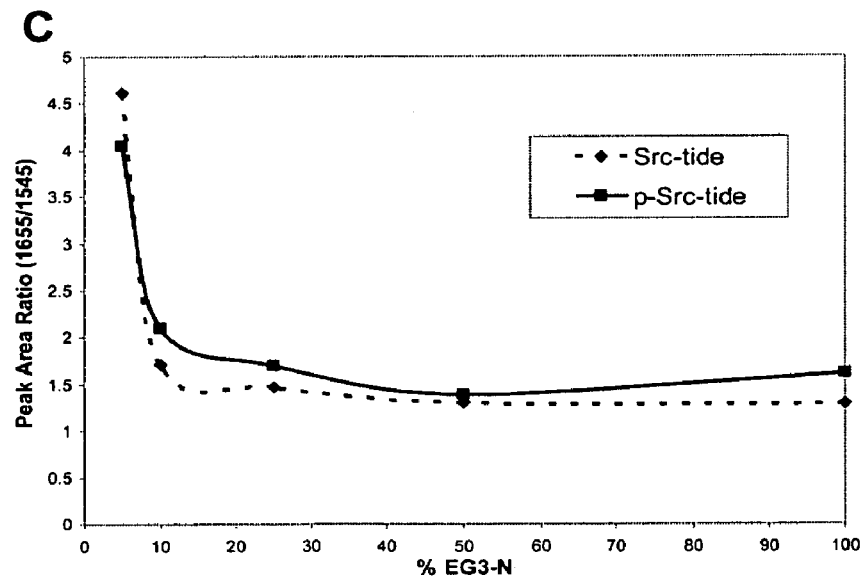
FIG. 14C is a graphical representation of the ratio of the peak areas at 1655 cm-1 and 1539 cm-1 of the peptide-modified SAMs samples of FIG. 14A as a function of the percent of EG3-N in the thiol mixture.

Since it has been observed that the solution conformation of a short peptide can change upon phosphorylation, whether the two peptides in the present system were immobilized at different densities due to orientational or conformational differences was studied. Indices used to characterize protein structures at interfaces by infrared spectroscopic methods are 1) the ratio of Amide I/Amide II peak intensities (to monitor orientation), and the peak position of the Amide I absorbance (to monitor secondary structure). These two peptide sequences were characterized using these two indices. First, inspection of the peak positions for the Amide I absorption for Src-tide and p-Src-tide occurs at 1655 cm$^{-1}$, leading to the conclusion that both peptides adopt a similar conformation and that each possesses some alpha helical character. Second, Amide I/Amide II peak area ratios were calculated for each peptide series and plotted these values as a function of the composition of the solution used to form the monolayer. FIG. 14C shows that changes in the orientations of peptides do occur as a function of areal density of peptide at the interface and that at maximum packing of peptides (50 and 100%) both Src-tide and p-Src-tide have similar orientations (ratio values). These results indicate that at maximum packing densities, each peptide has a similar orientation. These differences in maximum packing densities appear to reflect factors other than the orientations of the peptide. Long-range forces such as electrostatic interactions may be the origin of the differences in maximum packing densities. At a neutral pH in bulk solution, the charge states of Src-tide and p-Src-tide are +2 and 0, respectively.

The results indicate that a two-component SAM can be used to tune the areal density of both maleimide functional groups and immobilized peptides at an interface. These methods can be used to prepare samples for the study of liquid crystals in contact with surfaces presenting different areal densities of immobilized peptides.

Example 8

Orientations of Liquid Crystals in Contact with Peptide-Functionalized Surfaces

The orientations of the nematic liquid crystal 5CB in contact with the peptide-modified surfaces described above were studied. Semi-transparent films of obliquely deposited gold films were prepared as described in Example 1, were then treated so that each peptide was immobilized on SAMs prepared from solutions having compositions of 1, 5, 10, 25, 50 and 100% EG3–N. These samples present a wide range in peptide immobilization density and therefore could show the impact of peptide density on the orientational ordering of the liquid crystal. As a control, one-component SAMs comprised of only EG3 were prepared, such that these surfaces presented no peptide. To view the optical textures of liquid crystals in contact with these surfaces, optical cells were created using two identical surfaces placed face-to-face and separated by 12 μm. Cells were filled with the nematic liquid crystal 5CB and viewed using a polarized light microscope.

Optical cells for use in combination with polarized light microscopy were prepared in order to determine the orientations of liquid crystals in contact with the peptide-modified surfaces. The optical cell was fabricated by spacing two identically treated surfaces approximately 12 μm apart using thin strips of Saran wrap. To image the peptide arrays, hybrid cells were prepared using a surface on which peptides were patterned and a second surface that was OTS-treated glass. Preparation of octyltrichlorosilane (OTS)-treated glass slides was as follows. Piranha cleaned glass slides were immersed in a 10 mM solution of OTS in anhydrous n-heptane. After 30 minutes, each slide was rinsed with dichloromethane and dried under a stream of $N_2$. For all samples, the surfaces were held together at each end using bulldog clips, and warmed to approximately 40° C. 5CB, heated to its isotropic phase (~35° C.), was spontaneously drawn into each optical cell by capillary action. The optical cell was cooled to room temperature. During the cooling process, 5CB changed from its isotropic state to its nematic state. The optical appearance of the sample was observed in transmission mode using a polarized light microscope.

Images of the optical appearance of the liquid crystals were captured with a digital camera mounted on a polarized light microscope (BX60, Olympus). Consistent settings of both the microscope light source (aperture set at ½ maximum, and lamp intensity also set at ½ maximum) and the digital camera (2.8 f-stop, 1/650 shutter speed) allowed for the direct comparison of images taken of different samples. To quantify the luminosity of the liquid crystal in contact with the peptide arrays, each composite image was converted to a greyscale image. The average pixel brightness of a region was calculated, assigning a completely black pixel the value of 0 and a completely white pixel the value of 255.

Figures 15A, 15B:
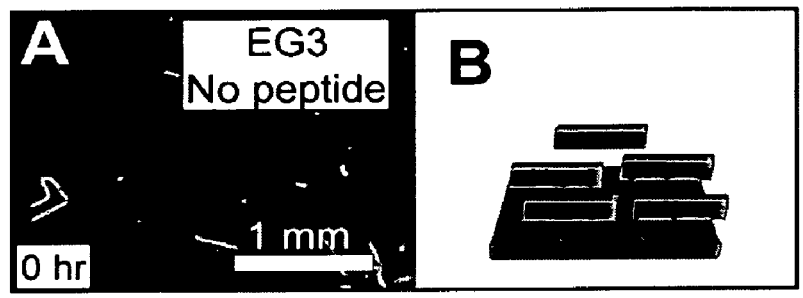
FIG. 15A is an optical polarization microscopy image of the nematic liquid crystal 5CB in contact with surfaces presenting a SAM from the EG3 thiol.
FIG. 15B is a schematic diagram of the molecular organization of 5CB molecules near the interface with the SAM as confirmed using optical methods.

An image of the optical appearance of the liquid crystal in contact with the 100% EG3 SAM is shown in FIG. 15A and FIG. 15B. The sample appears uniformly dark when observed using polarized light microscopy (crossed polarizers), as the liquid crystal is uniformly aligned by the surface. The average orientations of mesogens in the sample are parallel to one polarizer, causing the extinction of transmitted light. The changes in interference colors observed after inserting a quarter-wave plate into the path of transmitted light was used to characterize the orientation of 5CB with respect to the anisotropic topography of the underlying gold film. This study shows that 5CB in contact with 100% EG3 SAMs is uniformly aligned in the direction of maximum roughness of the gold film (FIG. 15B). The chemical structure of this interface, including the orientation of the terminal functional groups presented by the SAM, and interactions between 5CB and the SAM dictate the preferred orientations of 5CB on these surfaces.

Figure 16:
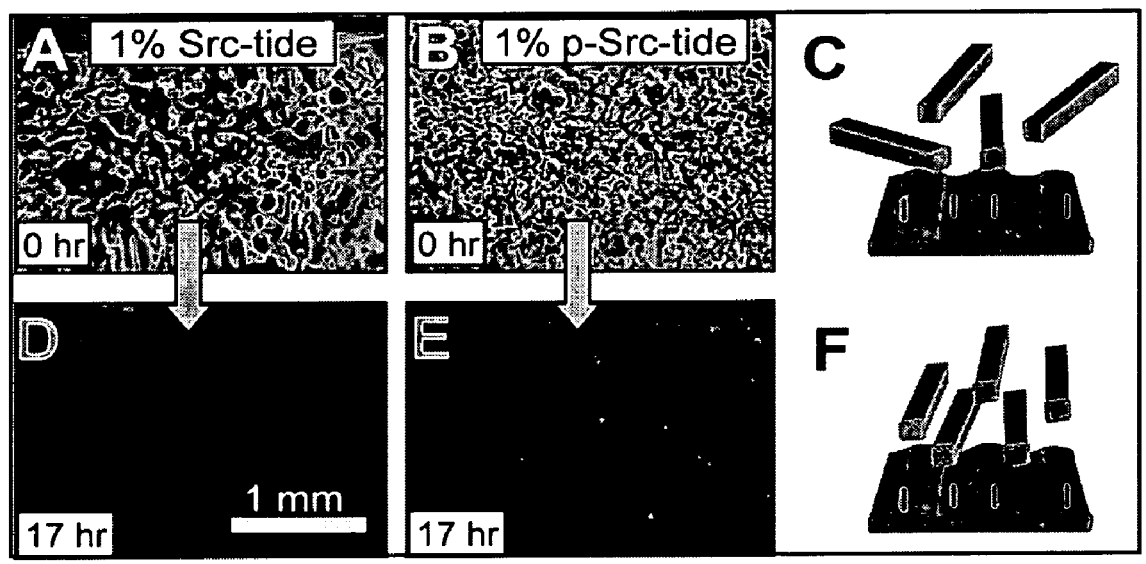
FIG. 16A and FIG. 16B are optical polarization microscopy images of the nematic liquid crystal 5CB in contact with surfaces presenting peptide-modified SAMs having 1% areal densities of Src-tide and p-Src-tide peptides, respectively, immediately after preparation.
FIG. 16D and FIG. 16E are an optical polarization microscopy images of the same preparations 17 hours later.
FIG. 16C and FIG. 16F are schematic diagrams of the molecular organization of 5CB molecules near the interface with the SAM immediately after preparation and 17 hours later.

The orientations of 5CB in contact with surfaces presenting low areal densities of immobilized peptides were studied. Samples of 5CB in contact with Src-tide or p-Src-tide modified SAMs formed from 1% EG3–N solutions were studied. When viewed immediately after preparation, the optical textures of 5CB in contact with these surfaces were non-uniform and possessed many line defects (FIG. 16A and FIG. 16B, illustrated schematically in FIG. 16C). Whether the liquid crystal in contact with surfaces having low areal densities of peptides was at an equilibrium state was studied. These same samples were annealed in a 36° C. oven for 17 hours. Once cooled, images were captured for each sample, and shown in FIG. 16D and FIG. 16E. After this annealing period, line defects were largely eliminated and the samples appeared uniformly dark when viewed under polarized light microscopy. Although bulk 5CB at 36° C. exists as an isotropic phase, past studies have established that the interfacial order of a thermotropic liquid crystal can persist at temperatures higher than the temperature at which the bulk phase becomes isotropic. Upon cooling, the interfacial order of the liquid crystal plays a central role in determining the orientation of the bulk liquid crystal. In these studies, the influence of thermal annealing above the bulk nematic-to-isotropic transition temperature was attributed to changes in the interfacial order of 5CB. If the samples were not heated to 36° C. (i.e. kept at ~25° C.), the annealing process was slowed to an extent that we saw no measurable change in the defect densities over the course of days. In contrast to the EG3 SAMs, the orientation of the 5CB in contact with these peptide-decorated interfaces was parallel to the direction of minimum roughness of the underlying gold film (illustrated schematically in FIG. 16F). That is, upon reaching equilibrium, the preferred orientation of 5CB in contact with these surfaces is orthogonal to what is observed with the EG3 SAM system. These results suggest that the molecular-level organization which defined the interactions between the liquid crystal and the EG3 SAM have been perturbed by the peptide immobilization. The presence of the peptide also appears to increase the time required for this system to equilibrate and exhibit long-range ordering.

Figure 17:
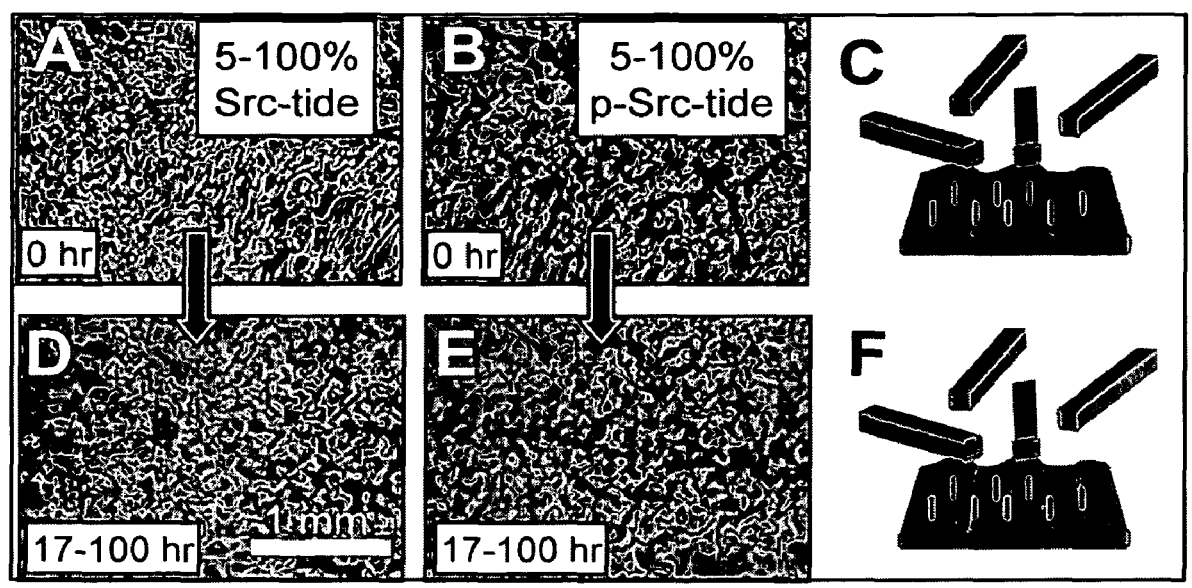
FIG. 17A and FIG. 17B are optical polarization microscopy images of the nematic liquid crystal 5CB in contact with surfaces presenting peptide-modified SAMs having 5-100% areal densities of Src-tide and p-Src-tide peptides, respectively, immediately after preparation.
FIG. 17D and FIG. 17E are an optical polarization microscopy images of the same preparations 17 hours later.
FIG. 17C and FIG. 17F are schematic diagrams of the molecular organization of 5CB molecules near the interface with the SAM immediately after preparation and 17 hours later.

The samples of 5CB in contact with either Src-tide or p-Src-tide at higher areal densities (5-100% EG3–N) immediately after preparation were also highly non-uniform (FIG. 17A and FIG. 17B, illustrated schematically in FIG. 17C). In contrast, these samples did not undergo a time-dependent annealing of defects upon heated to 36° C. for up to 100 hours (FIG. 17D and FIG. 17E, illustrated schematically in FIG. 17F). Recent simulations have predicted that particles adsorbed at interfaces can dramatically slow the dynamics of alignment of liquid crystals by surfaces.58 The simulations are used to establish a relationship between the number density of adsorbed particles and the time required to achieve equilibrium where the liquid crystal exhibits uniform ordering near the interface. Another conclusion drawn from the simulations is that above a critical areal density of adsorbed particles, the time required to achieve this state approaches infinity. The experimental evidence lends support to this model, as higher areal densities of immobilized peptides lead to exceedingly long times required to achieve the equilibrium state with long-range ordering of 5CB. These results, when combined, suggest a correlation between the areal density of immobilized peptides and the dynamic reorganization of 5CB. The measurement of relaxation times and defect densities offers the basis of new approaches to quantify the density of peptides at the interface.

The introduction of peptides at interfaces can thus perturb the initial alignment of liquid crystals in contact with self-assembled monolayers supported on obliquely deposited gold substrates. Such samples are not in an equilibrium state immediately after preparation, and the time required to achieve equilibrium is related to the number density of immobilized peptides at the interface. Thus, using surfaces having low areal densities of peptides reduces the time required to reach equilibrium.

Example 9

Using Liquid Crystals to Detect Peptide-Protein Binding Events

Past work has demonstrated that protein binding events at nanostructured gold interfaces can induce the presence of defects in liquid crystals in contact with those surfaces. The results of Example 8 indicate that surfaces which present low areal densities of peptide permit 5CB to relax over time to a defect-free structure, suggesting the hypothesis that surfaces presenting bound protein may prevent the relaxation of defects within the liquid crystal because the specific binding of proteins to surface-immobilized peptides increases both the effective number and size of biomolecules at the interface. To test this hypothesis, the orientations of nematic liquid crystal 5CB in contact with peptide-laden interfaces were measured both before and after treatment with a phospho-specific antibody. The resistance of these peptide-modified SAMs to the nonspecific adsorption of proteins was also studied. Ellipsometric thickness measurements were recorded and used to independently confirm the presence or absence of bound protein.

Surfaces having a low areal density of surface-immobilized peptides by using 1% EG3–N SAMs were prepared. FIG. 18A depicts the experimental design. Each peptide surface, one presenting Src-tide and the other presenting the phosphorylated sequence p-Src-tide, was treated with a 10 µg/mL solution of monoclonal anti-phosphotyrosine IgG for 1.5 hours. As a control, an identical set of peptide surfaces was treated with a 10 µg/mL solution of anti-avidin IgG, an antibody having no affinity for either peptide sequence, also for 1.5 hours. Prior to measuring the orientation of 5CB on these surfaces, independent confirmation of bound IgG was obtained using ellipsometry.

An increase in optical thickness of 2.3±0.1 nm was observed after placing the surface presenting p-Src-tide in contact with an aqueous solution of the monoclonal anti-phosphotyrosine IgG. This peptide sequence contains a phosphotyrosine residue, thus permitting binding between this peptide and the phosphotyrosine-specific antibody. A small negative change in optical thickness (−0.1±0.1 nm), within the error of measurement, was observed for the Src-tide-modified surface after treatment with the monoclonal anti-phosphotyrosine IgG. The lack of protein binding to the immobilized Src-tide confirms the selective binding between the phospho-specific antibody and the phosphorylated peptide sequence. Similar small changes (~0.2±0.1 nm) in optical thickness were observed when placing surfaces presenting these two peptides in contact with the anti-avidin IgG protein. These results are consistent with previous reports of ethylene glycol-containing SAMs resisting the non-specific adsorption of proteins to interfaces.

Optical images of the liquid crystal in contact with the surfaces described above, when viewed immediately after preparation under polarized microscopy, are shown in FIG. 18B. As expected, each of these samples had non-uniform optical textures. However, after a 17 hour annealing period at 36° C., samples of 5CB in contact with the control surfaces presenting no bound antiphosphotyrosine IgG (confirmed by ellipsometry) relaxed to a uniform, defect-free structure (FIG. 18C). In addition, samples of liquid crystal in contact with peptide surfaces exposed to solutions of anti-avidin IgG annealed to a defect-free state over the course of 17 hours. This is consistent with the ellipsometric thickness measurements confirming no non-specifically adsorbed protein at these interfaces. Interference studies using quarter-wave plate measurements again confirmed that the orientation of 5CB was defined by the underlying surface topography. In contrast, after annealing, 5CB in contact with the p-Src-tide surface presenting bound monoclonal anti-phosphotyrosine IgG remained non-uniformly oriented, even after many weeks of annealing. These results support the hypothesis that the specific binding of an antibody to a surface-immobilized peptide increases the effective number (and size) of adsorbed particles at the interface, and thus slows the dynamic reorganization of mesogens near the interface such that the time required for this system to reach equilibrium extends beyond the experimentally accessed time-scale. This label-free detection method of protein (antibody)-peptide binding events has potential application in the design of medical diagnostics and in the study of enzymatic activity. Prior work has demonstrated that it is possible to quantify the optical response of a liquid crystal in contact with surfaces presenting increasing amounts of antibody bound to an immobilized antigen. Skaife, J. J.; Abbott, N. L. *Langmuir* 2000, 16, 3529. In that report, a correlation is drawn between the number of line defects per unit area and the quantity of bound protein.

Example 10

Imaging of Spatially-Resolved Peptide Arrays Using Liquid Crystals

Surface-based assays are highly amenable for high-throughput screening (HTS), as many thousands of spatially-resolved chemical or biomolecular species can be simultaneously tested for a given function. Liquid crystals can conceivably image such highly dense arrays, as previous work has demonstrated that a nematic liquid crystal can be used to resolve surfaces patterned with feature sizes having lateral dimensions of <10 microns.

The peptide arrays were prepared as follows. SAMs composed of EG3–N and EG3 thiols were formed on films of obliquely deposited gold films as described above. The entire surface was then treated with a 2 mM solution of SSMCC in TEA. Next, ~2.5 µL of a 250 µM solution of peptide in TEA were applied to this surface as spots (having lateral dimensions of ~1 mm). After 3 hr, the entire surface was rinsed 2×1.5 mL×5 min TEA+0.1% TX. The remaining maleimide groups were quenched by treatment of the entire surface with a 2 mM solution of 2-mercaptoethanol in PBS for 10 min. Finally these samples were rinsed and dried. Monoclonal anti-phosphotyrosine IgG was applied to the peptide surfaces for 1.5 hr as a 10 µg/mL solution in PBS+0.05% TX (approximately 67 nM when assuming MW of antibody ~150,000 g/mol). Control samples were prepared by treating similar peptide surfaces with a 10 µg/mL solution of monoclonal anti-avidin IgG (~67 nM) in PBS+0.05% TX for an equal length of time. All samples were rinsed for 15 s in PBS+ 0.05% Triton-X 100, then with water, and finally dried under a stream of $N_2$.

These simple arrays were generated on SAMs composed of 1% EG3–N. The entire interface was first treated with male-imide-containing linker, SSMCC. Next, defined regions of peptides Src-tide and p-Src-tide were created by applying 0.5 µL of a 250 µM solution of each peptide (spot lateral dimension ~1-2 mm) onto the maleimide-modified surface. The entire surface was then quenched with 2-mercaptoethanol to passivate any remaining maleimide groups in background regions. The resultant surface is shown in FIG. 19A. Finally, the entire surface was treated with the monoclonal anti-phosphotyrosine IgG, rinsed and then dried. The optical cell used to study liquid crystal orientations was assembled using this patterned surface and an opposing surface comprised of octyltrichlorosilane (OTS) treated glass. OTS-treated glass is known to orient 5CB perpendicular to the surface plane (homeotropic anchoring). With the liquid crystal fixed in a known orientation at one surface confining the liquid crystal (OTS-treated glass), it is possible to spatially probe the orientation of the liquid crystal at the opposite face (the array). This strategy has been previously used to image spatially-defined domains of proteins and lipids at an aqueous-liquid crystal interface.

The optical image of SCB in contact with this peptide array, upon reaching equilibrium (17 hour annealing period), is shown in FIG. 19B. As the size of the sample exceeded the viewing frame of the microscope, composite images were constructed from several separate images. SCB in contact with regions of the chip not presenting bound protein assumes a relatively uniform texture, where the alignment of the liquid crystal is defined by the underlying topography of the gold film. In contrast, 5CB in contact with regions of the surface presenting monoclonal anti-phosphotyrosine IgG bound to p-Src-tide has a non-uniform optical texture and appears as bright, defect-containing spots under polarized light microscopy. FIG. 19C presents the luminosity of light transmitted through 5CB in contact with each region of the sample; using gray-scale conversion and image analysis described above. Some noise and variability in the amount of light transmitted through 5CB contacting regions of the chip which present only Src-tide were observed, suggesting that liquid crystals constrained in hybrid cells are somewhat more sensitive to the presence of peptides than the cells constructed of two identical peptide surfaces.

A modified apparatus was constructed using methods identical to the experiment described above to reduce this noise and optimize the detection of this protein binding event, except that a 0.5% EG3-N SAM was used. The surface pattern, optical images of the liquid crystal upon reaching equilibrium, and results obtained by image analysis are shown in FIG. 19A, FIG. 19B, and FIG. 19C. In contrast to the experiment using a 1% EG3-N SAM, a lower and more reproducible background noise level was observed, without diminishing the response of the liquid crystal in contact with regions presenting bound monoclonal anti-phosphotyrosine IgG (remaining at luminosity index ~170). These results further highlight the effect of peptide areal density on the orientations of liquid crystals. These results, when combined, demonstrate that it is possible to rationally optimize this system by tuning the areal densities of peptides presented on SAMs formed on gold substrates.

Example 11

Rapid Detection of Phosphorylated Peptides

Figure 21A:
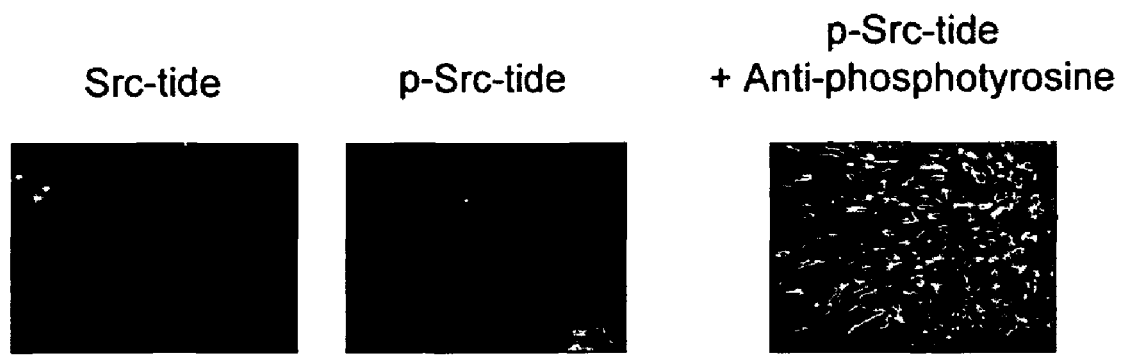
FIG. 21A shows the images of surfaces that present the peptide sequences Src-tide and p-Src-tide were prepared using SAMs formed from solutions of 1% EG4–N/(EG3+EG3–N). An additional surface presenting the p-Src-tide was prepared and exposed to anti-phosphotyrosine IgG. The array is shown diagrammatically in FIG. 21B.

This example demonstrates a method for the detection of phosphorylated peptide at surfaces at short timescales using liquid crystals. Surfaces that present the peptide sequences Src-tide and p-Src-tide were prepared using SAMs formed from solutions 99:1 EG4/EG3-N. An additional surface presenting the p-Src-tide was prepared and exposed to anti-phosphotyrosine IgG. These samples were placed in contact with liquid crystals and viewed using polarized microscopy as shown in FIG. 21A. The orientations of liquid crystal on the surfaces presenting peptide only, when viewed within 5 minutes after sample preparation, are uniform in texture. In contrast, the orientations of the the liquid crystal in contact with p-Src-tide bound to anti-phosphotyrosine IgG are non-uniform in texture. This difference in optical appearance serves as a basis for detecting the presence of the phosphorylated peptide and specifically bound IgG.

Figure 21B:
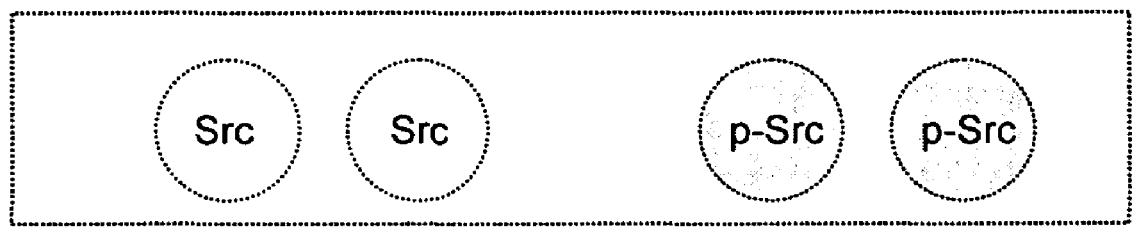
FIG. 21C are images of the liquid crystal in contact with the surfaces within 5 minutes of contact.

Additionally, a peptide array was prepared (schematic shown in FIG. 21B) that presented spatially-defined regions of Src-tide and p-Src-tide. The entire sample was placed in contact with a solution of anti-phosphotyrosine antibody.

Figure 21C:
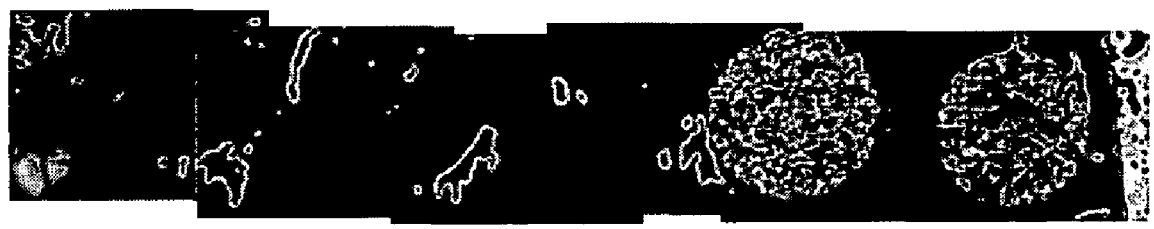

Gold substrates were prepared by physical vapor deposition at an oblique angle of 45°. The gold substrates were then immersed in an ethanolic solution of EG4 and EG3-N (99: 1, total thiol concentration 0.1 mM) for no less than 12 hours. These substrates were then modified with peptides as previously described (sequential treatments of SSMCC and then cysteine-containing peptides Src-tide and p-Src-tide). When appropriate, surfaces were placed in contact with solutions of anti-phosphotyrosine IgG (67 nM in phosphate buffered saline, pH 7.4+0.05% triton-X). For the experimental results shown in FIG. 21A, optical cells were created by placing identically treated substrates face-to-face, separated by 12 micrometer spacers. The optical cell was filled with liquid crystal 5CB by capillarity and viewed using polarized microscopy. For the experimental results shown in FIG. 21C, the optical cell comprised of a peptide array was formed by placing the array face-to-face with a glass surface treated with octyltrichlorosilane, separated by 12 micrometer spacers. This cell was filled with 5CB and viewed under polarized microscopy The orientations of the liquid crystal, when viewed within 5 minutes after sample preparation, are uniform at regions of the substrate that present Src-tide, and are non-uniform at regions of the substrate that present p-Src-tide. The differences in optical textures can be used to detect the presence of phosphorylated peptides at interfaces.

Example 12

Detection of Cells Adherent to Peptide-Modified Surfaces

This example demonstrates that liquid crystals can be used to report the presence of cells adhered to peptide-modified surfaces. Surfaces were modified with the cysteine-terminated peptide CGGRGDS (SEQ ID NO: 7). In this experiment, a one-component SAM formed from EG3-N was used. This peptide sequence is known to influence cell adhesion at interfaces. The CGGRGDS (SEQ ID NO: 7)-modified surfaces were placed in contact with solutions of 3T3 fibroblasts in serum (concentration of 50,000 cells/mL). The cells were stained with Calcein-AM (fluorescent dye that is specific for living cells). These surfaces were rinsed and then used to prepare optical cells. This surface was placed face-to-face with an octyltrichlorosilane-treated glass surface, separated by 12 micrometer spacers. The optical cell was filled with the liquid crystal TL205 (E. Merck, Darmstadt, Germany) and viewed using both fluorescence microscopy and polarized microscopy.

Figure 22A:
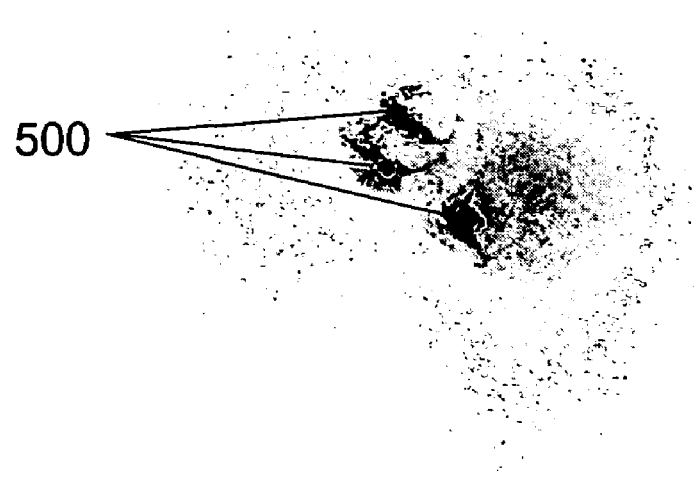
FIG. 22A is an optical image of a region of the sample when viewed under fluorescence microscopy. Regions 500 correspond to cells that were stained by the Calcein-AM are visible, here dark instead of bright in this/reversed-contrast image. Without moving the sample, the microscope was converted to its polarizing light function, and viewed using crossed polarizers, shown in FIG. 22B. The textures of the liquid crystal TL205 in contact with regions of the surface that do not present cells are uniform and bright.
Figure 22B:
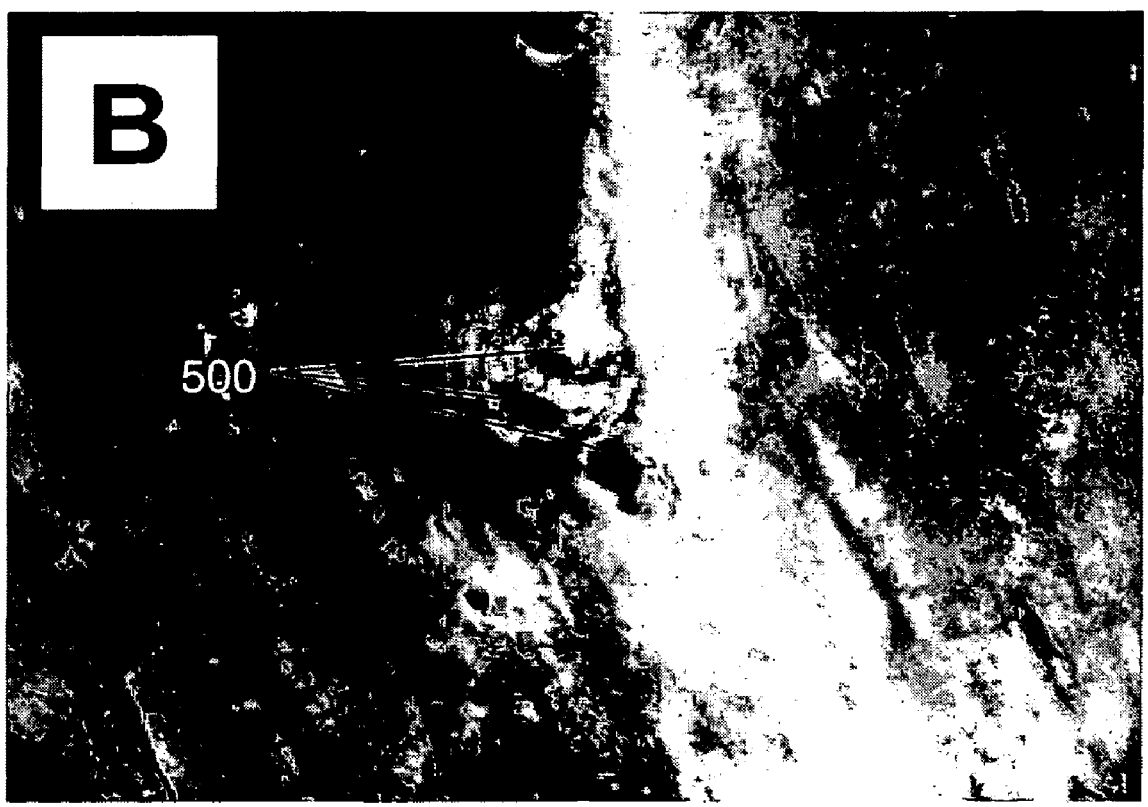
FIG. 22 shows images of cells Surfaces were modified with the cysteine-terminated peptide CGGRGDS (SEQ ID NO: 7). In this experiment, a one-component SAM formed from EG3–N was used. This peptide sequence is known to influence cell adhesion at interfaces. The CGGRGDS (SEQ ID NO: 7)-modified surfaces were placed in contact with solutions of 3T3 fibroblasts in serum (concentration of 50,000 cells/mL). The cells were stained with Calcein-AM (fluorescent dye that is specific for living cells). These surfaces were rinsed and then used to prepare optical cells. This surface was placed face-to-face with an octyltrichlorosilane-treated glass surface, separated by 12 micrometer spacers. The optical cell was filled with the liquid crystal TL205 (a mixture of halogenated bi- and triphenyls with aliphatic tail lengths of two to five carbons, E. Merck, Darmstadt, Germany) and viewed using both fluorescence microscopy and polarized microscopy.

FIG. 22A is an optical image of a region of the sample when viewed under fluorescence microscopy. Regions 500 correspond to cells that were stained by the Calcein-AM are visible, here dark instead of bright in this/reversed-contrast image. Without moving the sample, the microscope was converted to its polarizing light function, and viewed using crossed polarizers, shown in FIG. 22B. The textures of the liquid crystal TL205 in contact with regions of the surface that do not present cells are uniform and bright. In contrast, the textures of the liquid crystal TL205 in contact with regions of the sample known to have adhered cells is dark. This difference in optical texture can be used to determine the presence or absence of cells attached to the surface.

All references cited herein are hereby incorporated by reference in their entirety and for all purposes as if fully set forth herein.

It is understood that the invention is not limited to the embodiments set forth herein for illustration, but embraces all such forms thereof as come within the scope of the following claims.

The invention claimed is:

1. A device for differentiating between a post-translationally modified peptide and a peptide, comprising:
   (a) a support having a top surface;
   (b) metal overlying the top surface of the support providing a metallized surface;
   (c) a functionalized thiol compound comprising the reaction product of a first thiol compound comprising a —S-Metal linkage formed when a thiol compound comprising an —SH group is attached to the top of the metallized surface and further comprising an amine or ammonium group or an ammonium salt thereof linked to a heterobifunctional linker comprising a functional group that is capable of reacting with an —SH group on a post-translationally modified peptide or a peptide; and
   (d) a liquid crystal in contact with the functionalized thiol compound of (c) above,
   wherein the post-translationally modified peptide, and the peptide are bound to the functionalized thiol compound of (c) and wherein the orientation of the liquid crystal in contact with the post-translationally modified peptide is different than the orientation of the liquid crystal in contact with the peptide, thereby differentiating between the post-translationally modified peptide and the peptide.

2. The device of claim 1, further comprising:
   (e) a second thiol compound comprising an —S-Metal linkage formed when a thiol compound comprising an —SH group is attached to the top of the metallized surface, wherein the second thiol compound is a compound having the formula Metal-S—$(CH_2)_c$—$(OCH_2CH_2)_d$—X, wherein c is an integer ranging from 1 to 30, and d is an integer ranging from 0 to 10, and X is selected from an —OH, an alkoxy group, a $CH_3$, a sugar, a zwitterionic group, or a polar non-ionic group.

3. The device of claim 1, wherein the metallized surface comprises a top layer of gold and wherein the top layer of gold overlies a layer of titanium that promotes adhesion of the gold to the support.

4. A kit, comprising the device of claim 1 and a recognition reagent, wherein the recognition reagent is an antibody, and antibody fragment, or a cationic compound.

5. A kit, comprising the device of claim 1, and a recognition reagent, wherein the recognition reagent is an antibody, an antibody fragment, a cationic surfactant, a polyelectrolyte, a cationic iron compound, or a phosphosensor dye.

6. The device of claim 1, wherein the recognition reagent is an antibody or an antibody fragment that selectively binds or forms a complex with a post-translationally modified peptide.

7. The device of claim 2 wherein the molar ratio of the functionalized thiol compound of (c) to the second thiol compound attached to the top surface of the support ranges from 0.1:99.9 to 50:50.

8. The device of claim 1 wherein the functionalized thiol compound of (c) has the formula:

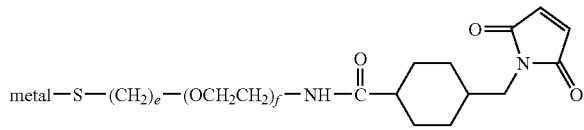

wherein e is an integer ranging from 1 to 30 and f is an integer ranging from 0 to 10.

* * * * *

UNITED STATES PATENT AND TRADEMARK OFFICE
CERTIFICATE OF CORRECTION

PATENT NO. : 7,795,007 B2  Page 1 of 1
APPLICATION NO. : 11/156911
DATED : September 14, 2010
INVENTOR(S) : Nicholas L. Abbott, Brian H. Clare and Paul J. Bertics It is certified that error appears in the above-identified patent and that said Letters Patent is hereby corrected as shown below:

Column 11, Line 3 "1,5%" should be -- i, 5% --

Signed and Sealed this

Sixteenth Day of November, 2010

David J. Kappos
*Director of the United States Patent and Trademark Office*

SEQUENCE LISTING

```
<160> NUMBER OF SEQ ID NOS: 7

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide
```

-continued

```
<400> SEQUENCE: 1

Ile Tyr Gly Glu Phe Lys Lys Lys Cys
1               5

<210> SEQ ID NO 2
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: PHOSPHORYLATION

<400> SEQUENCE: 2

Ile Tyr Gly Glu Phe Lys Lys Lys Cys
1               5

<210> SEQ ID NO 3
<211> LENGTH: 11
<212> TYPE: PRT
<213> ORGANISM: Artificial sequence
<220> FEATURE:
<223> OTHER INFORMATION: Synthetic peptide

<400> SEQUENCE: 3

Cys Gly Gly Ala Leu Arg Arg Ala Ser Leu Gly
1               5                   10

<210> SEQ ID NO 4
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: PHOSPHORYLATION

<400> SEQUENCE: 4

Cys Gly Gly Ala Leu Arg Arg Ala Ser Leu Gly
1               5                   10

<210> SEQ ID NO 5
<211> LENGTH: 6
<212> TYPE: PRT
<213> ORGANISM: Artificial sequence
<220> FEATURE:
<223> OTHER INFORMATION: Synthetic peptide

<400> SEQUENCE: 5

Lys Arg Thr Ile Arg Arg
1               5

<210> SEQ ID NO 6
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: PHOSPHORYLATION
```

```
-continued

<400> SEQUENCE: 6

Lys Arg Thr Ile Arg Arg
1               5

<210> SEQ ID NO 7
<211> LENGTH: 7
<212> TYPE: PRT
<213> ORGANISM: Artificial sequence
<220> FEATURE:
<223> OTHER INFORMATION: Synthetic peptide

<400> SEQUENCE: 7

Cys Gly Gly Arg Gly Asp Ser
1               5
```